US012665048B2

(12) United States Patent
Chen et al.

(10) Patent No.: US 12,665,048 B2
(45) Date of Patent: Jun. 23, 2026

(54) SYNTHON EMBEDDINGS FOR MODELING DNA-ENCODED LIBRARIES

(71) Applicant: Insitro, Inc., South San Francisco, CA (US)

(72) Inventors: Benson Chen, Palo Alto, CA (US); Mohammad Muneeb Sultan, San Francisco, CA (US); Theofanis Karaletsos, San Francisco, CA (US)

(73) Assignee: Insitro, Inc., South San Francisco, CA (US)

( * ) Notice: Subject to any disclaimer, the term of this patent is extended or adjusted under 35 U.S.C. 154(b) by 0 days.

(21) Appl. No.: 19/000,940

(22) Filed: Dec. 24, 2024

(65) Prior Publication Data

US 2025/0131979 A1     Apr. 24, 2025

Related U.S. Application Data

(63) Continuation of application No. PCT/US2024/048716, filed on Sep. 26, 2024.

(60) Provisional application No. 63/540,425, filed on Sep. 26, 2023.

(51) Int. Cl.
| | |
|---|---|
| *G01N 33/48* | (2006.01) |
| *G01N 33/50* | (2006.01) |
| *G06N 20/00* | (2019.01) |
| *G16B 15/30* | (2019.01) |
| *G16C 20/10* | (2019.01) |

(52) U.S. Cl.
CPC ............. *G16B 15/30* (2019.02); *G06N 20/00* (2019.01); *G16C 20/10* (2019.02)

(58) Field of Classification Search
CPC ......... G16B 15/30; G06N 20/00; G16C 20/10
See application file for complete search history.

(56) References Cited

U.S. PATENT DOCUMENTS

2023/0130619 A1* 4/2023 Ma ........................ G06F 18/27
                                                                      702/19

FOREIGN PATENT DOCUMENTS

KR          102237189 B1 * 4/2021 ............. G06N 20/00

OTHER PUBLICATIONS

Kundu et al. A machine learning approach towards the prediction of protein-ligand binding affinity based on fundamental molecular properties. RSC Advances, vol. 8, pp. 12127-12137. (Year: 2018).*
Deng et al. DeepMHADTA: Prediction of drug-target binding affinity using multi-head self attention and convolution neural network. Current Issues in Molecular Biology, vol. 44, May 19, 2022, pp. 2287-2299. (Year: 2022).*
English machine translation of KR-102237189-B1. (Year: 2025).*
International Search Report and Written Opinion for PCT/US2024/048716, mailed Dec. 16, 2024, 13 pages.
Chen, B., et al., "Compositional Deep Probabilistic Models of DNA-Encoded Libraries", Journal of Chemical Information and Modeling, vol. 64, No. 4, Feb. 9, 2024, pp. 1123-1133.
Bui-Thi, D., et al., "Predicting compound-protein interaction using hierachical graph convolutional networks", PLOS ONE, vol. 17, No. 7, Jul. 21, 2022, 19 pages.
Lim, K., et al., "Machine learning on DNA-encoded library count data using an uncertainty-aware probabilistic loss function", arxiv.org, Cornell University Library, 201 Olin Library Cornell University Ithaca, NY 14853, Aug. 27, 2021.
Mccloskey, K., et al., "Machine Learning on DNA-Encoded Lirbaries: A New Paradigm for Hit Finding", Journal of Medicinal Chemistry, vol. 63, No. 16, Jun. 11, 2020, pp. 8857-8866.
Li, Z., et al., "Deep learning methods for molecular representation and property prediction", Drug Discovery Today, vol. 27, No. 12, Sep. 24, 2022, 13 pages.
Gerry, C., et al., "DNA barcoding a complete matrix of stereoisomeric small molecules", J Am Chem Soc. Jul. 3, 2019; 141(26): 10225-10235.
Lim, K., et al., "Machine learning on DNA-encoded library count data using an uncertainty-aware probabilistic loss function", arxiv.org, Cornell University Library, 201 Olin Library Cornell University Ithaca, NY 12471, Apr. 27, 2022.

* cited by examiner

*Primary Examiner* — Russell S Negin
(74) *Attorney, Agent, or Firm* — Goodwin Procter LLP

(57)          ABSTRACT

Embodiments of the disclosure involve modeling DEL data using factorized molecular representations (e.g., hierarchical mono-synthon and di-synthon building blocks), which capitalizes on the inherent hierarchical structure of these molecules. Using the factorized molecular representations, machine learning models are trained to learn latent binding affinity of compounds for targets and one or more covariates (e.g., load/replicate noise). This leads to improved predictions by the machine learning models in the form of higher enrichment scores, which are well-correlated with compound-target binding affinity.

15 Claims, 31 Drawing Sheets

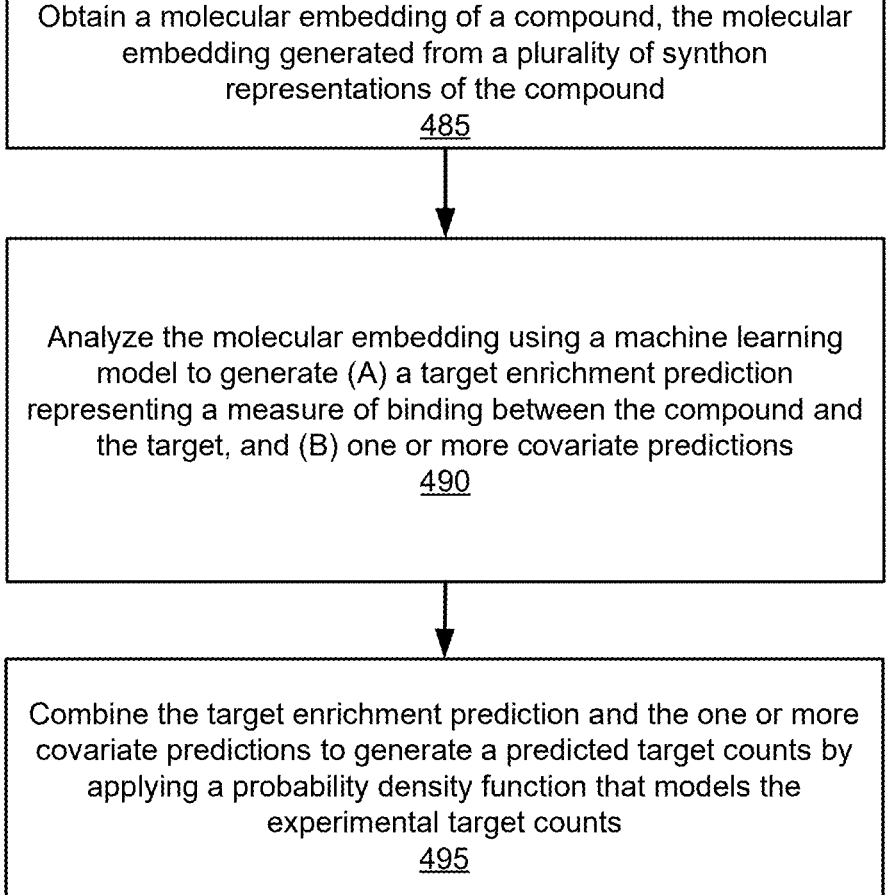

Obtain a molecular embedding of a compound, the molecular embedding generated from a plurality of synthon representations of the compound
485

Analyze the molecular embedding using a machine learning model to generate (A) a target enrichment prediction representing a measure of binding between the compound and the target, and (B) one or more covariate predictions
490

Combine the target enrichment prediction and the one or more covariate predictions to generate a predicted target counts by applying a probability density function that models the experimental target counts
495

FIG. 4C

Training

725

750

SYNTHON EMBEDDINGS FOR MODELING DNA-ENCODED LIBRARIES

CROSS-REFERENCE TO RELATED APPLICATIONS

This application is a continuation of PCT/US24/48716, filed Sep. 26, 2024, which claims the benefit of and priority to U.S. Provisional Patent Application No. 63/540,425 filed Sep. 26, 2023, the entire disclosure of which is hereby incorporated by reference in its entirety for all purposes.

BACKGROUND OF THE INVENTION

DNA-Encoded Libraries (DELs) have demonstrated their potency as a robust method for conducting efficient exploration across a vast chemical landscape. These small molecule libraries are synthesized combinatorically by combining diverse building blocks with compatible chemistries. A DNA barcode, which is covalently attached to the molecule, specifies the unique combination of building blocks for each molecule. These small molecule libraries are then used in selection experiments for a protein of interest, wherein multiple rounds of washing and elution are performed before identification of the surviving library molecules. While proven to be a highly efficient process of exploring chemical space at scale, these selection experiments are often highly noisy and requires computation methods with the correct inductive biases to extract useful signals for downstream applications such as hit discovery and lead optimization. Thus, there is a need for improved methodologies for handling DEL experimental outputs to build improved machine learning models for exploring chemical spaces.

SUMMARY

Disclosed herein are methods, non-transitory computer readable media, and systems involving an approach to model DEL data by factorizing molecular representations into their hierarchical mono-synthon and di-synthon building blocks, which capitalizes on the inherent hierarchical structure of these molecules. The disclosed methods explicitly factorize molecular representations in a motivated manner. Specifically, individual synthon representations, including corresponding di-synthon, tri-synthon, and additional combinations of synthons, are learned from their respective factorized representations. This avoids the necessity of numerating full-molecule structures, which is often a tedious process prone to errors.

Additionally, covariate factors are integrated in the modeling to more effectively account for data noise. For example, models trained herein consider different experimental biases, including two prominent sources of noise inherent in DEL data stemming from pre-selection and replicate-level biases. Since DEL molecules are synthesized using a split-and-pool method, the relative abundance of each library member is uncertain in the final mixture. While the library itself is sequenced to obtain a rough estimate of the molecule distribution, this count data is also prone to potential synthesis and sequencing biases. Across different replicates, different experimental or sequencing noise are also expected. Our model tries to ameliorate the effects of these factors in order to better model the observed count data and learn useful latent enrichments of DEL molecules. The disclosed machine learning models demonstrate strong performance compared to count baselines, enriches the correct pharmacophores, and offers valuable insights via its intrinsic interpretable structure, thereby providing a robust tool for the analysis of DEL data.

Altogether, machine learned models disclosed herein are useful for various applications including conducting virtual compound screens, performing hit selection and analyses, and identifying common binding motifs. Conducting a virtual compound screen enables identifying compounds from a library (e.g., virtual library) that are likely to bind to a target, such as a protein target. Performing a hit selection enables identification of compounds that likely exhibit a desired activity. For example, a hit can be a compound that binds to a target (e.g., a protein target) and therefore, exhibits a desired effect by binding to the target. Predicting binding affinity between compounds and targets can result in the identification of compounds that exhibit a desired binding affinity. For example, binding affinity values can be continuous values and therefore, can be indicative of different types of binders (e.g., strong binder or weak binder). This enables the identification and categorization of compounds that exhibit different binding affinities to targets. Identifying common binding motifs can be useful for understanding the mechanism between binders of a target. An understanding of binding motifs can be useful for developing additional new small molecule compounds e.g., during medicinal chemistry campaigns. In various embodiments, the predicted binding affinity is correlated with the activity of a compound. For example, a compound with a higher predicted binding affinity can be correlated with higher activity. In various embodiments, the predicted binding affinity may not be directly correlated with the activity of a compound. For example, in some scenarios, a compound with a higher predicted binding affinity may exhibit lower activity in comparison to a second compound with a lower predicted binding affinity.

Disclosed herein is a method for performing molecular screening of a compound for binding to a target, the method comprising: obtaining a plurality of synthons forming the compound; transforming the plurality of synthons into a plurality of synthon representations; combining the plurality of synthon representations into a molecular embedding; using a machine learning model, analyzing the molecular embedding to generate at least a target enrichment prediction representing a measure of binding between the compound and the target. In various embodiments, the method additionally features performing probabilistic modeling using at least the target enrichment prediction by applying a probability density function that models experimental target counts. In various embodiments, the probability density function is represented by any one of a Poisson distribution, Binomial distribution, Gamma distribution, Binomial-Poisson distribution, or negative binomial distribution. In various embodiments, the Poisson distribution is a zero-inflated Poisson distribution.

In various embodiments, using the machine learning model to analyze the molecular embedding further generates an covariate prediction. In various embodiments, the method does not comprise a step of enumerating the compound from the plurality of synthons. In various embodiments, transforming the plurality of synthons into a plurality of synthon representations comprises generating one or more monosynthon representations from the plurality of synthons. In various embodiments, generating one or more monosynthon representations from the plurality of synthons comprises analyzing the plurality of synthons using a learned representation model, optionally wherein the learned representation model is a multilayer perceptron. In various embodiments, transforming the plurality of synthons into a plurality of synthon representations further comprises generating one or more disynthon representations from the one or more monosynthon representations. In various embodiments, generating one or more disynthon representations from the one or more monosynthon representations comprises analyzing the one or more monosynthon representations using a learned representation model, optionally wherein the learned representation model is a multilayer perceptron. In various embodiments, transforming the plurality of synthons into a plurality of synthon representations further comprises generating one or more trisynthon representations from the one or more disynthon representations. In various embodiments, generating one or more trisynthon representations from the one or more disynthon representations comprises analyzing the one or more disynthon representations using a learned representation model, optionally wherein the learned representation model is a multilayer perceptron.

In various embodiments, the plurality of synthon representations comprise one or more monosynthon representations. In various embodiments, the plurality of synthon representations comprise one or more disynthon representations. In various embodiments, the plurality of synthon representations comprise one or more trisynthon representations. In various embodiments, the plurality of synthon representations comprise one or more tetrasynthon representations. In various embodiments, the plurality of synthon representations comprise one or more monosynthon representations, one or more disynthon representations, and one or more trisynthon representations. In various embodiments, the plurality of synthon representations comprise three monosynthon representations, three disynthon representations, and one trisynthon representation.

In various embodiments, the machine learning model comprises a neural network. In various embodiments, the neural network comprises a feedforward artificial neural network. In various embodiments, the neural network comprises a multilayer perceptron (MLP). In various embodiments, the machine learning model comprises one or more parameters learned through supervised training techniques. In various embodiments, methods disclosed herein further comprise determining a binding affinity value between the compound and the target using the target enrichment prediction. In various embodiments, methods disclosed herein further comprise ranking the compound according to at least the target enrichment prediction.

In various embodiments, combining the plurality of synthon representations into a molecular embedding comprises implementing a multi-head attention mechanism across the plurality of synthon representations. In various embodiments, implementing the multi-head attention mechanism comprises using one or more learned attention weights of the plurality of synthon representations. In various embodiments, methods disclosed herein further comprise using the one or more learned attention weights to rank the plurality of synthons for their ability to bind to the target. In various embodiments, the covariate prediction arises from one or more covariates comprising any of non-specific binding or noise. In various embodiments, non-specific binding comprise one or more of binding to beads, binding to matrix, binding to streptavidin of the beads, binding to biotin, binding to gels, binding to DEL container surfaces, or binding to tags. In various embodiments, the noise comprise one or more of load bias, replicate bias, enrichment in other negative control pans, enrichment in other target pans, promiscuity, compound synthesis yield, reaction type, starting tag imbalance, initial load populations, experimental conditions, chemical reaction yields, side and truncated products, errors from the library synthesis, DNA affinity to target, sequencing depth, and sequencing noise.

In various embodiments, the covariate prediction arises from load noise. In various embodiments, the covariate prediction arises from replicate noise. In various embodiments, using the machine learning model to analyze the molecular embedding further generates a second covariate prediction. In various embodiments, the covariate prediction and the second covariate prediction are each, independently, selected from non-specific binding or noise. In various embodiments, the covariate prediction arises from load noise, and the second covariate prediction arises from replicate noise. In various embodiments, transforming the plurality of synthons into the plurality of synthon representations comprises applying one or more trained learned representation models. In various embodiments, the machine learning model is trained using one or more training compounds with corresponding DNA-encoded library (DEL) outputs. In various embodiments, the corresponding DNA-encoded library (DEL) outputs for a training compound comprises: experimental control counts determined through a first panning experiment; and experimental target counts determined through a second panning experiment. In various embodiments, for one of the training compounds, the machine learning model is trained by: generating, by the machine learning model, a target enrichment prediction and an covariate prediction from a molecular embedding generated by combining a plurality of synthon representations transformed from a plurality of synthons forming the training compound; combining the target enrichment prediction and the covariate prediction to generate a predicted target counts; and determining, according to a loss function, a loss value based on at least the predicted target counts and the experimental target counts. In various embodiments, training the machine learning model according to the determined loss value. In various embodiments, methods disclosed herein further comprise jointly training the machine learning model with one or more learned representation models according to the determined loss value. In various embodiments, the loss value is further determined based on the covariate predictions and the experimental control counts. In various embodiments, the loss function is any one of a negative log-likelihood loss, binary cross entropy loss, focal loss, arc loss, cosface loss, cosine based loss, or loss function based on a BEDROC metric.

In various embodiments, combining the target enrichment prediction and the covariate prediction to generate a predicted target counts comprises applying a probability density function that models the experimental target counts. In various embodiments, the probability density function is represented by any one of a Poisson distribution, Binomial distribution, Gamma distribution, Binomial-Poisson distribution, or negative binomial distribution. In various embodiments, the Poisson distribution is a zero-inflated Poisson distribution. In various embodiments, the machine learning model is further trained by: generating a predicted control count from the covariate prediction by applying a probability density function that models the experimental control counts. In various embodiments, the probability density function that models the experimental control counts is represented by any one of a Poisson distribution, Binomial distribution, Gamma distribution, Binomial-Poisson distribution, or negative binomial distribution. In various embodiments, the Poisson distribution is a zero-inflated Poisson distribution. In various embodiments, the measure of binding is any one of a binding affinity, DEL counts, DEL reads, or DEL indices.

In various embodiments, the molecular screen is a virtual molecular screen. In various embodiments, the compound is from a virtual library of compounds. In various embodiments, the target comprises a protein target. In various embodiments, the protein target is a human carbonic anhydrase IX (CAIX) protein target, a horseradish peroxidase (HRP) protein target, a discoidin domain receptor tyrosine kinase 1 (DDR1) protein target, or mitogen-activated protein kinase 14 (MAPK14) protein target. In various embodiments, methods disclosed herein further comprise: identifying a common binding motif across a subset of the one or more compounds, wherein the compounds in the subset have predicted measures of binding above a threshold binding value.

Additionally disclosed herein is a method for generating a molecular embedding of a compound, the method comprising: obtaining a plurality of synthons forming the compound; transforming the plurality of synthons into a plurality of synthon representations, wherein the transformation comprises: generating one or more monosynthon representations by analyzing the plurality of synthons using a first learned representation model; generating one or more disynthon representations by analyzing the one or more monosynthon representations using a second learned representation model; generating one or more trisynthon representations by analyzing the one or more disynthon representations using a third learned representation model; and combining the plurality of synthon representations into a molecular embedding. In various embodiments, combining the plurality of synthon representations into a molecular embedding comprises implementing a multi-head attention mechanism across the plurality of synthon representations. In various embodiments, transforming the plurality of synthons into a plurality of synthon representations further comprises generating one or more N-synthon representations, wherein N is 4, 5, 6, 7, 8, 9, 10, 11, 12, 13, 14, 15, 16, 17, 18, 19, or 20. In various embodiments, the first learned representation model comprises a multilayer perceptron. In various embodiments, the second learned representation model comprises a multilayer perceptron. In various embodiments, the third learned representation model comprises a multilayer perceptron. In various embodiments, the plurality of synthon representations comprise one or more monosynthon representations, one or more disynthon representations, one or more trisynthon representations, or one or more tetrasynthon representations. In various embodiments, the plurality of synthon representations comprise one or more monosynthon representations, one or more disynthon representations, and one or more trisynthon representations. In various embodiments, the plurality of synthon representations comprise three monosynthon representations, three disynthon representations, and one trisynthon representation.

Additionally disclosed herein is a method for predicting experimental counts of a DNA-encoded library (DEL), the method comprising: obtaining a molecular embedding of a compound, the molecular embedding generated from a plurality of synthon representations of the compound; using a machine learning model, analyzing the molecular embedding to generate (A) a target enrichment prediction representing a measure of binding between the compound and the target, and (B) one or more covariate predictions; and combining the target enrichment prediction and the one or more covariate predictions to generate a predicted target counts by applying a probability density function that models the experimental target counts. In various embodiments, the probability density function is represented by any one of a Poisson distribution, Binomial distribution, Gamma distribution, Binomial-Poisson distribution, or negative binomial distribution. In various embodiments, the Poisson distribution is a zero-inflated Poisson distribution. In various embodiments, the one or more covariate predictions arise from one or more covariates comprising any of non-specific binding or noise. In various embodiments, non-specific binding comprise one or more of binding to beads, binding to matrix, binding to streptavidin of the beads, binding to biotin, binding to gels, binding to DEL container surfaces, or binding to tags. In various embodiments, the noise comprise one or more of load bias, replicate bias, enrichment in other negative control pans, enrichment in other target pans, promiscuity, compound synthesis yield, reaction type, starting tag imbalance, initial load populations, experimental conditions, chemical reaction yields, side and truncated products, errors from the library synthesis, DNA affinity to target, sequencing depth, and sequencing noise. In various embodiments, at least one of the one or more covariate predictions arises from load noise. In various embodiments, at least one of the one or more covariate predictions arises from replicate noise. In various embodiments, a first covariate prediction arises from load noise, and a second covariate prediction arises from replicate noise. In various embodiments, the one or more covariate predictions comprise two, three, four, five, six, seven, eight, nine, ten, eleven, twelve, thirteen, fourteen, fifteen, sixteen, seventeen, eighteen, nineteen, or twenty covariate predictions.

Additionally disclosed herein is a method for predicting experimental counts of a DNA-encoded library (DEL), the method comprising: obtaining a target enrichment prediction representing a measure of binding between a compound and a target and performing a probabilistic modeling using at least the target enrichment prediction by applying a probability density function to model experimental target counts of the DEL.

In various embodiments, the probabilistic modeling comprises implementing any one of a Poisson distribution, Binomial distribution, Gamma distribution, Binomial-Poisson distribution, or negative binomial distribution. In various embodiments, the Poisson distribution is a zero-inflated Poisson distribution.

In various embodiments, the method further comprises obtaining a covariate prediction, and wherein performing the probabilistic modeling further uses the covariate prediction. In various embodiments, the covariate prediction arises from one or more covariates comprises any of non-specific binding or noise. In various embodiments, the non-specific binding comprise one or more of binding to beads, binding to matrix, binding to streptavidin of the beads, binding to biotin, binding to gels, binding to DEL container surfaces, or binding to tags. In various embodiments, wherein the noise comprise one or more of load bias, replicate bias, enrichment in other negative control pans, enrichment in other target pans, promiscuity, compound synthesis yield, reaction type, starting tag imbalance, initial load populations, experimental conditions, chemical reaction yields, side and truncated products, errors from the library synthesis, DNA affinity to target, sequencing depth, and sequencing noise. In various embodiments, the covariate prediction arises from load noise. In various embodiments, the covariate prediction arises from replicate noise.

In various embodiments, the target enrichment prediction is generated by a machine learning model trained using one or more training compounds with corresponding DNA-encoded library (DEL) outputs. In various embodiments, the machine learning model comprises a neural network. In various embodiments, the neural network comprises a feed-forward artificial neural network. In various embodiments, the neural network comprises a multilayer perceptron (MLP). In various embodiments, the machine learning model comprises one or more parameters learned through supervised training techniques.

In various embodiments, the machine learning model generates the target enrichment prediction by: analyzing a molecular embedding to generate at least the target enrichment prediction representing a measure of binding between the compound and the target. In various embodiments, the corresponding DNA-encoded library (DEL) outputs for a training compound comprises: experimental control counts determined through a first panning experiment and experimental target counts determined through a second panning experiment. In various embodiments, wherein for one of the training compounds, the machine learning model is trained by: generating, by the machine learning model, a target enrichment prediction and an covariate prediction from a molecular embedding generated by combining a plurality of synthon representations transformed from a plurality of synthons forming the training compound, combining the target enrichment prediction and the covariate prediction to generate a predicted target counts, and determining, according to a loss function, a loss value based on at least the predicted target counts and the experimental target counts. In various embodiments, the machine learning model is trained according to the determined loss value.

In various embodiments, the machine learning model further comprising jointly training the machine learning model with one or more learned representation models according to the determined loss value. In various embodiments, the loss value is further determined based on the covariate predictions and the experimental control counts. In various embodiments, the loss function is any one of a negative log-likelihood loss, binary cross entropy loss, focal loss, arc loss, cosface loss, cosine based loss, or loss function based on a BEDROC metric. In various embodiments, wherein combining the target enrichment prediction and the covariate prediction to generate a predicted target counts comprises applying a probability density function that models the experimental target counts. In various embodiments, the probability density function is represented by any one of a Poisson distribution, Binomial distribution, Gamma distribution, Binomial-Poisson distribution, or negative binomial distribution. In various embodiments, the Poisson distribution is a zero-inflated Poisson distribution.

In various embodiments, wherein the machine learning model is further trained by: generating a predicted control count from the covariate prediction by applying a probability density function that models the experimental control counts. In various embodiments, the probability density function that models the experimental control counts is represented by any one of a Poisson distribution, Binomial distribution, Gamma distribution, Binomial-Poisson distribution, or negative binomial distribution. In various embodiments, the Poisson distribution is a zero-inflated Poisson distribution. In various embodiments, the measure of binding is any one of a binding affinity, DEL counts, DEL reads, or DEL indices. In various embodiments, the target comprises a protein target.

In various embodiments, the protein target is a human carbonic anhydrase IX (CAIX) protein target, a mitogen-activated protein kinase 14 (MAPK14) protein target, a discoidin domain receptor tyrosine kinase 1 (DDR1) protein target, or a horseradish peroxidase (HRP) protein target.

Additionally disclosed herein is a non-transitory computer readable medium comprising instructions that, when executed by a processor, cause the processor to perform any of the methods disclosed herein. Additionally disclosed herein is a system comprising: a processor; and a non-transitory computer readable medium comprising instructions that, when executed by the processor, cause the processor to perform any of the methods disclosed herein.

BRIEF DESCRIPTION OF THE DRAWINGS

These and other features, aspects, and advantages of the present invention will become better understood with regard to the following description and accompanying drawings. It is noted that, wherever practicable, similar or like reference numbers may be used in the figures and may indicate similar or like functionality. For example, a letter after a reference numeral, such as "DEL experiment 115A," indicates that the text refers specifically to the element having that particular reference numeral. A reference numeral in the text without a following letter, such as "DEL experiment 115," refers to any or all of the elements in the figures bearing that reference numeral (e.g., "DEL experiment 115" in the text refers to reference numerals "DEL experiment 115A" and/or "DEL experiment 115B" in the figures). As another example, "synthon 310" refers to any or all of the elements of "synthon 310A", "synthon 310B", and "synthon 310C".

FIG. 4C depicts an example flow process for predicting experimental counts for a DEL, in accordance with an embodiment.

DETAILED DESCRIPTION OF THE INVENTION

Definitions

Figure 1A:
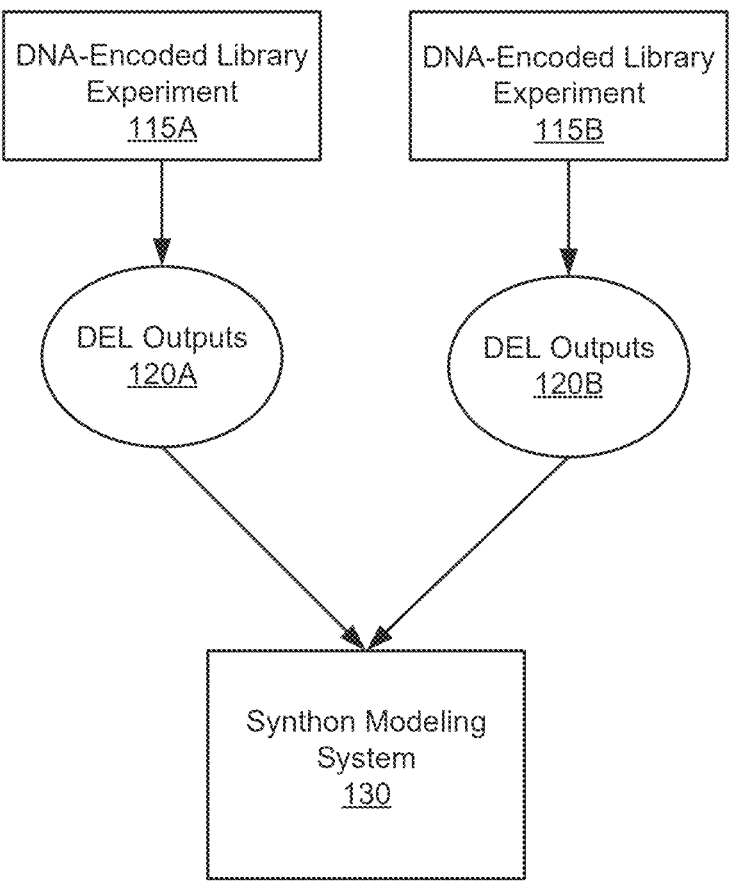
FIG. 1A depicts an example system environment involving a synthon modeling system, in accordance with an embodiment.

Terms used in the claims and specification are defined as set forth below unless otherwise specified.

The phrase "obtaining a plurality of synthons forming a compound" comprises generating a plurality of synthons of a compound or obtaining a plurality of synthons of the compound e.g., from a third party that generated the plurality of synthons of the compound.

The phrase "synthon" represents a molecular building block of a compound. In various embodiments, a synthon represents a starting agent in the synthesis of the compound. A compound may be composed of a plurality of synthons. In various embodiments, a compound is composed of two synthons. In various embodiments, a compound is composed of three synthons. In various embodiments, a compound is composed of four synthons. In various embodiments, a compound is composed of five synthons, six synthons, seven synthons, eight synthons, nine synthons, ten synthons, eleven synthons, twelve synthons, thirteen synthons, fourteen synthons, fifteen synthons, sixteen synthons, seventeen synthons, eighteen synthons, nineteen synthons, or twenty synthons. In various embodiments, a compound is composed of more than twenty synthons.

The phrase "synthon representation" refers to a representation of a synthon, such as a transformation of a synthon into a representation space. First, a synthon may be expressed in a particular structure format, including any of a simplified molecular-input line-entry system (SMILES) string, MDL Molfile (MDL MOL), Structure Data File (SDF), Protein Data Bank (PDB), Molecule specification file (xyz), International Union of Pure and Applied Chemistry (IUPAC) International Chemical Identifier (InChI), and Tripos Mol2 file (mol2) format. In various embodiments, a synthon can be represented as an encoding, such as a fingerprint or a graph of the synthon. A representation of the synthon may be a transformation of the synthon in a particular structure format. In various embodiments, a representation of a synthon can be either continuous or discrete. An example synthon representation can be an embedding of a synthon, which is a numerical representation of the synthon. In various embodiments, the embedding of a synthon is generated via one of a neural network, a graph neural network, a transformer, or a multi-layer perceptron.

The phrase "target enrichment prediction" refers to a prediction learned by a machine learning model informative for a measure of binding between a compound and a target. In various embodiments, the target enrichment prediction is a value or a score. Generally, the target enrichment prediction is informative (e.g., correlated) for a measure of binding between a compound and a target, and a prediction that is denoised to account for a covariate prediction (e.g., absent influence from covariates and other sources of noise). In various embodiments, the target enrichment prediction is learned by attempting to predict the experimental DEL counts (which includes counts arising from sources of noise and covariates).

The phrase "covariate prediction" refers to a prediction learned by a machine learning model that arises from a covariate. In various embodiments, the covariate prediction is a value or a score. Example covariates can include sources of noise (e.g., sources of noise in DEL experiments), and non-specific binding (e.g., binding to beads, binding to matrix, binding to streptavidin of the beads, binding to biotin, binding to gels, binding to DEL container surfaces, binding to tags e.g., DNA tags or protein tags). Example sources of noises include biases (e.g., pre-selection counts bias or replicate bias), enrichment in other negative control pans, enrichment in other target pans, promiscuity, compound synthesis yield, reaction type, starting tag imbalance, initial load populations, experimental conditions, chemical reaction yields, side and truncated products, errors from the library synthesis, DNA affinity to target, sequencing depth, and sequencing noise such as PCR bias. In particular embodiments, the covariate prediction is a prediction of non-specific binding (e.g., binding to matrix). In particular embodiments, the covariate prediction is a prediction of pre-selection counts bias. In particular embodiments, the covariate prediction is a prediction of load bias.

The phrases "pre-selection counts bias" and "load bias" are used interchangeably and generally refer to the bias in the true signal arising from a difference in starting populations in DEL panning experiments. For example, certain molecules can be present in different quantities in comparison to other molecules (e.g., some molecules may be present at a 10-1000+ fold higher quantity than other molecules). The difference in starting populations can lead to load bias due to that molecular series surviving by chance alone.

The phrase "replicate bias" refers to a bias in the true signal that arises from sequencing or experimental issues across technical experiments. Example issues can include poor protein constructs and/or imprecise volume transfer in wells/replicates. In various embodiments, replicate bias can also be caused by differing sequencing depth across replicates. Altogether, these issues can lead to significantly attenuated signals that are not a true reflection of the DEL experiment.

The phrase "MAPK14" refers to mitogen-activated protein kinase 14. The phrase "DDR1" refers to discoidin domain receptor tyrosine kinase 1. The phrase "CAIX" refers to carbonic anhydrase IX. The phrase "HRP" refers to horseradish peroxidase.

It must be noted that, as used in the specification and the appended claims, the singular forms "a," "an" and "the" include plural referents unless the context clearly dictates otherwise.

Overview of System Environment

FIG. 1A depicts an example system environment involving a synthon modeling system 130, in accordance with an embodiment. In particular, FIG. 1A introduces DNA-encoded library (DEL) experiment 115A and DNA-encoded library (DEL) experiment 115B for generating DEL outputs (e.g., DEL output 120A and DEL output 120B) that are provided to the synthon modeling system 130 for training and deploying machine learning models. In particular embodiments, machine learning models are useful for generating target enrichment predictions which can be correlated to a measure of binding between compounds and targets e.g., for performing a virtual compound screen or for selecting and analyzing hits.

DEL experiments may involve DNA barcode-labeled pooled compound collections that are incubated with an immobilized protein target in a process referred to as panning. The mixture is then washed to remove non-binders, and the remaining bound compounds are eluted. In various embodiments, the remaining bound compounds can undergo one or more additional rounds of incubation, wash, and elution. For example, the remaining bound compounds can undergo two, three, four, five, six, seven, eight, nine, or ten additional rounds of incubation, wash, and elution. The remaining bound compounds are amplified, and sequenced to identify putative binders. DELs provide a quantitative readout for numerous (e.g., up to billions of) compounds.

As shown in FIG. 1A, two DEL experiments 115A and 115B may be conducted. However, in various embodiments, fewer or additional DEL experiments can be conducted. In various embodiments, different DEL experiments 115A and 115B shown in FIG. 1A can refer to different replicates of similar/same experimental conditions. In various embodiments, the example system environment involves at least three DEL experiments, at least four DEL experiments, at least five DEL experiments, at least six DEL experiments, at least seven DEL experiments, at least eight DEL experiments, at least nine DEL experiments, at least ten DEL experiments, at least fifteen DEL experiments, at least twenty DEL experiments, at least thirty DEL experiments, at least forty DEL experiments, at least fifty DEL experiments, at least sixty DEL experiments, at least seventy DEL experiments, at least eighty DEL experiments, at least ninety DEL experiments, or at least a hundred DEL experiments. The output (e.g., DEL output) of one or more of the DEL experiments can be provided to the synthon modeling system 130 for training and deploying machine learning models.

In various embodiments, a DEL experiment involves screening small molecule compounds of a DEL library against targets. In some embodiments, a DEL experiment involves screening multiple DEL libraries (e.g., in a single pool or across multiple pools). Generally, the DEL experiments (e.g., DEL experiments 115A or 115B) involve building small molecule compounds using chemical building blocks, also referred to as synthons. In various embodiments, small molecule compounds can be generated using two chemical building blocks, which are referred to di-synthons. In various embodiments, small molecule compounds can be generated using three chemical building blocks, which are referred to as tri-synthons. In various embodiments, small molecule compounds can be generated using four or more, five or more, six or more, seven or more, eight or more, nine or more, ten or more, fifteen or more, twenty or more, thirty or more, forty or more, or fifty or more chemical building blocks. In various embodiments, a DNA-encoded library (DEL) for a DEL experiment can include at least $10^3$ unique small molecule compounds. In various embodiments, a DNA-encoded library (DEL) for a DEL experiment can include at least $10^4$ unique small molecule compounds. In various embodiments, a DNA-encoded library (DEL) for a DEL experiment can include at least $10^5$ unique small molecule compounds. In various embodiments, a DNA-encoded library (DEL) for a DEL experiment can include at least $10^6$ unique small molecule compounds. In various embodiments, a DNA-encoded library (DEL) for a DEL experiment can include at least $10^7$ unique small molecule compounds. In various embodiments, a DNA-encoded library (DEL) for a DEL experiment can include at least $10^8$ unique small molecule compounds. In various embodiments, a DNA-encoded library (DEL) for a DEL experiment can include at least $10^9$ unique small molecule compounds. In various embodiments, a DNA-encoded library (DEL) for a DEL experiment can include at least $10^{10}$ unique small molecule compounds. In various embodiments, a DNA-encoded library (DEL) for a DEL experiment can include at least $10^{11}$ unique small molecule compounds. In various embodiments, a DNA-encoded library (DEL) for a DEL experiment can include at least $10^{12}$ unique small molecule compounds.

Generally, small molecule compounds in the DEL are each made up of chemical building blocks, also referred to herein as synthons. In various embodiments, the synthons may be individually labeled with tags. In various embodiments, a synthon may be individually labeled with tag via a linker. Therefore, a small molecule compound may be labeled with multiple tags corresponding to the synthons that make up the small molecule compound. In various embodiments, the small molecule compound can be covalently linked to a unique tag. In various embodiments, the tags include nucleic acid sequences. In various embodiments, the tags include DNA nucleic acid sequences.

In various embodiments, for a DEL experiment (e.g., DEL experiment 115A or 115B), small molecule compounds that are labeled with tags are incubated with immobilized targets. In various embodiments, targets are nucleic acid targets, such as DNA targets or RNA targets. In various embodiments, targets are protein targets. In particular embodiments, protein targets are immobilized on beads. The mixture is washed to remove small molecule compounds that did not bind with the targets. The small molecule compounds that are bound to the targets are eluted and can undergo one or more additional rounds of incubation, wash, and elution. The corresponding tag sequences of remaining compounds are amplified. In various embodiments, the tag sequences are amplified through one or more rounds of polymerase chain reaction (PCR) amplification. In various embodiments, the tag sequences are amplified using an isothermal amplification method, such as loop-mediated isothermal amplification (LAMP). The amplified sequences are sequenced to determine a quantitative readout for the number of putative small molecule compounds that were bound to the target. Further details of the methodology of building small molecule compounds of DNA-encoded libraries and methods for identifying putative binders of a DEL target are described in McCloskey, et al. "Machine Learning on DNA-Encoded Libraries: A New Paradigm for Hit Finding."*J. Med. Chem.* 2020, 63, 16, 8857-8866, and Lim, K. et al "Machine learning on DNA-encoded library count data using an uncertainty-aware probabilistic loss function." arXiv: 2108.12471, each of which is hereby incorporated by reference in its entirety.

Figure 1B:
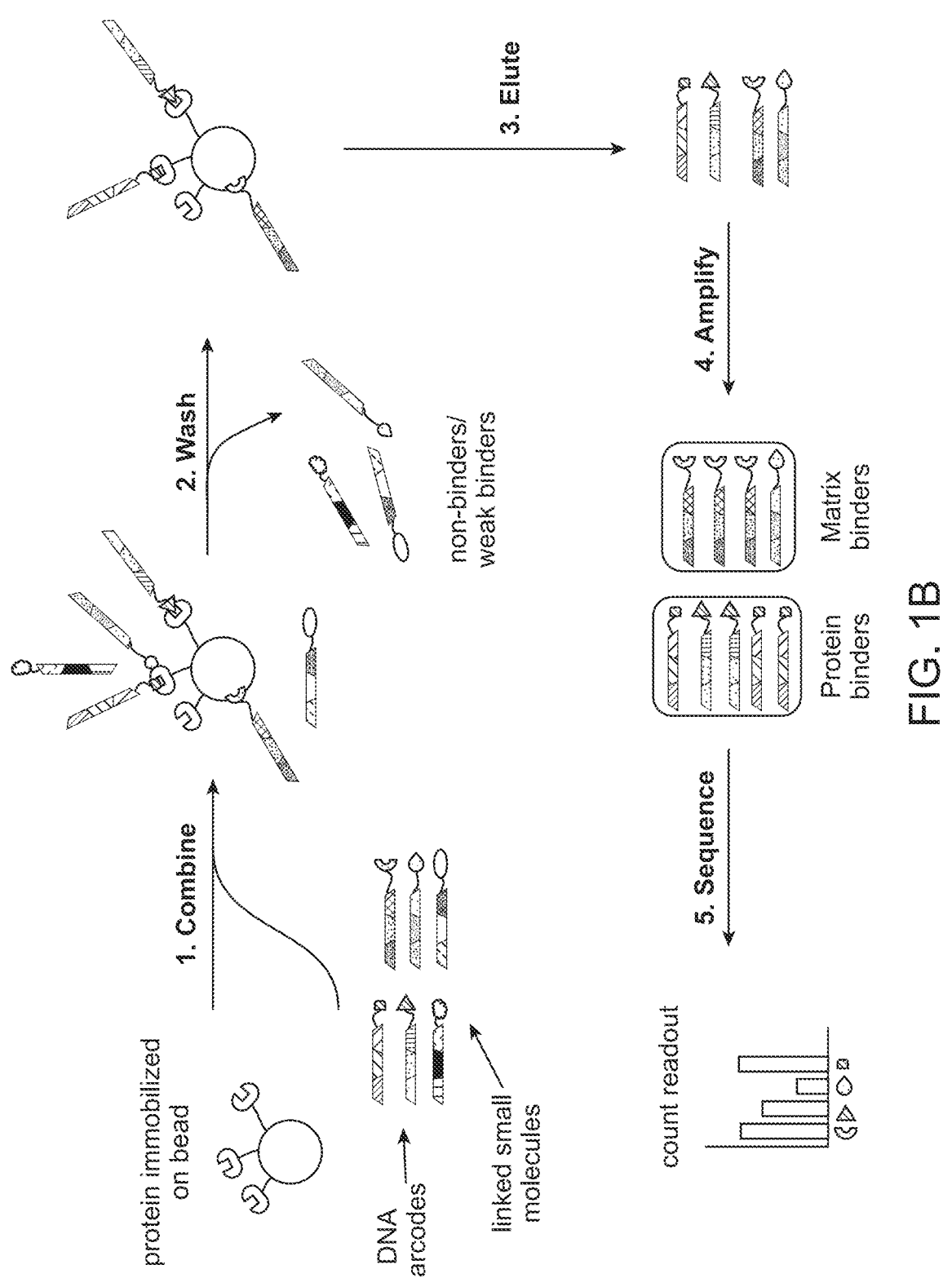
FIG. 1B depicts an example DNA-Encoded Library (DEL) panning experiment, in accordance with an embodiment.

Reference is made to FIG. 1B, which depicts an example DNA-Encoded Library (DEL) panning experiment, in accordance with an embodiment. DNA-encoded libraries (DELs) may be constructed by sequentially assembling molecular building blocks, aka synthons, into molecules tagged with unique DNA-barcode identifiers. These are shown in FIG. 1B as "linked small molecules" with DNA barcodes. Once synthesized, the library is tested for affinity against a target of interest (e.g., a protein target of interest) through a series of selection experiments. For example, as shown in FIG. 1B, the target of interest may be a protein immobilized on a bead.

An experiment, also referred to herein as panning, involves combining the DEL molecule into a solution of the immobilized target of interest (e.g., step 1 shown in FIG. 1B). Step 2 shown in FIG. 1B involves washing the resulting mixture for multiple rounds. Non-binders and weak binders are removed due to the wash. This procedure leaves members of the DEL that remain bound (e.g., bound to the target of interest or bound to other elements, such as the matrix). Step 3 involves eluting the DEL molecules that remain bound. The eluted DEL molecules then undergo amplification at step 4. Of note, there may be some DEL molecules that were bound to the matrix (shown in FIG. 1B as "Matrix binders") and therefore, did not wash away during the step 2 wash. These matrix binders may represent covariates and/or noise and are not actually binders to the target of interest. In contrast, the actual DEL molecules that are bound to the target of interest (shown in FIG. 1B as "Protein binders") are also obtained.

At step 5, presence of the DEL molecules is subsequently identified using next-generation DNA sequencing. The resulting data after bioinformatics processing can include reads of the DNA and the corresponding molecules. Thus, the relative abundance (e.g., number of DEL counts) of the identified members of the DEL is, in theory, a reasonable proxy for their binding affinities.

In various embodiments, for a DEL experiment (e.g., DEL experiment 115A or 115B), small molecule compounds are screened against targets using solid state media that house the targets. Here, in contrast to panning-based systems which used immobilized targets on beads, targets are incorporated into the solid-state media. For example, this screen can involve running small molecule compounds of the DEL using electrophoresis through a solid-state medium such as a gel that includes the target. The gel is then sliced to obtain tags that were used to label small molecule compounds. The presence of a tag suggests that the small molecule compound is a putative binder to the target that was incorporated in the gel. The tags are amplified (e.g., through PCR or an isothermal amplification process such as LAMP) and then sequenced. Further details for gel electrophoresis methodology for identifying putative binders is described in International Patent Application No. PCT/US2020/022662, entitled "Methods and Systems for Processing or Analyzing Oligonucleotide Encoded Molecules," which was filed Mar. 13, 2020 and is hereby incorporated by reference in its entirety.

In various embodiments, one or more of the DNA-encoded library experiments 115 are performed to model one or more covariates (e.g., off-target covariates or covariate predictions). Generally, a covariate refers to an experimental influence that impacts a DEL output (e.g., DEL counts) of a DEL experiment, and therefore serves as a confounding factor in determining the actual binding between a small molecule compound and a target. Example covariates can include sources of noise (e.g., sources of noise in DEL experiments), and non-specific binding (e.g., binding to beads, binding to matrix, binding to streptavidin of the beads, binding to biotin, binding to gels, binding to DEL container surfaces, binding to tags e.g., DNA tags or protein tags). Example sources of noises include biases (e.g., pre-selection counts bias or replicate bias), enrichment in other negative control pans, enrichment in other target pans, promiscuity, compound synthesis yield, reaction type, starting tag imbalance, initial load populations, experimental conditions, chemical reaction yields, side and truncated products, errors from the library synthesis, DNA affinity to target, sequencing depth, and sequencing noise such as PCR bias. In particular embodiments, a covariate is pre-selection counts bias. In particular embodiments, a covariate is load bias. In particular embodiments, a first covariate is pre-selection counts bias and a second covariate is load bias. Thus, different DEL experiments can be performed to model the pre-selection counts bias and the load bias.

To provide an example, a DEL experiment 115 may be designed to model the covariate of small molecule compound binding to beads. Here, if a small molecule compound binds to a bead instead of or in addition to the immobilized target on the bead, the subsequent washing and eluting step may result in the detection and identification of the small molecule compound as a putative binder, even though the small molecule compound does not bind specifically to the target. Thus, a DEL experiment 115 for modeling the covariate of non-specific binding to beads may involve incubating small molecule compounds with beads without the presence of immobilized targets on the bead. The mixture of the small molecule compound and the beads is washed to remove non-binding compounds that did not bind with the beads. The small molecule compounds bound to beads are eluted and the corresponding tag sequences are amplified (e.g., amplified through PCR or isothermal amplification such as LAMP). The amplified sequences are sequenced to determine a quantitative readout for the number of small molecule compounds that were bound to the bead. Thus, this quantitative readout can be a DEL output (e.g., DEL output 120) from a DEL experiment (e.g., DEL experiment 115) that is then provided to the synthon modeling system 130.

As another example, a DEL experiment 115 may be designed to model the covariate of small molecule compound binding to streptavidin linkers on beads. Here, the streptavidin linker on a bead is used to attach the target (e.g., target protein) to a bead. If a small molecule compound binds to the streptavidin linker instead of or in addition to the immobilized target on the bead, the subsequent washing and eluting step may result in the detection and identification of the small molecule compound as a putative binder, even though the small molecule compound does not bind specifically to the target. Thus, a DEL experiment 115 for modeling the covariate of non-specific binding to beads may involve incubating small molecule compounds with streptavidin linkers on beads without the presence of immobilized targets on the bead. The mixture of the small molecule compound and the streptavidin linker on beads is washed to remove non-binding compounds. The small molecule compounds bound to streptavidin linker on beads are eluted and the corresponding tag sequences are amplified (e.g., amplified through PCR or isothermal amplification such as LAMP). The amplified sequences are sequenced to determine a quantitative readout for the number of small molecule compounds that were bound to the streptavidin linkers on beads. Thus, this quantitative readout can be a DEL output (e.g., DEL output 120) from a DEL experiment (e.g., DEL experiment 115) that is then provided to the synthon modeling system 130.

As another example, a DEL experiment 115 may be designed to model the covariate of small molecule compound binding to a gel, which arises when implementing the nDexer methodology. Here, if a small molecule compound binds to the gel during electrophoresis instead of or in addition to the immobilized target on the bead, the subsequent washing and eluting step may result in the detection and identification of the small molecule compound as a putative binder, even though the small molecule compound does not bind to the target. Thus, the DEL experiment 115 may involve incubating small molecule compounds with control gels that do not incorporate the target. The small molecule compounds bound or immobilized within the gel are eluted and the corresponding tag sequences are amplified (e.g., amplified through PCR or isothermal amplification such as LAMP). The amplified sequences are sequenced to determine a quantitative readout for the number of small molecule compounds that were bound or immobilized in the gel. Thus, this quantitative readout can be a DEL output (e.g., DEL output 120) from a DEL experiment (e.g., DEL experiment 115) that is then provided to the synthon modeling system 130.

In various embodiments, at least two of the DEL experiments 115 are performed to model one covariate. For example, a first DEL experiment is performed for the target whereas a second DEL experiment is performed to model the covariate. In various embodiments, at least two of the DEL experiments 115 are performed to model at least two covariates. In various embodiments, at least three DEL experiments 115 are performed to model at least three covariates. In various embodiments, at least four DEL experiments 115 are performed to model at least four covariates. In various embodiments, at least five DEL experiments 115 are performed to model at least five covariates. In various embodiments, at least six DEL experiments 115 are performed to model at least six covariates. In various embodiments, at least seven DEL experiments 115 are performed to model at least seven covariates. In various embodiments, at least eight DEL experiments 115 are performed to model at least eight covariates. In various embodiments, at least nine DEL experiments 115 are performed to model at least nine covariates. In various embodiments, at least ten DEL experiments 115 are performed to model at least ten covariates. The DEL outputs from each of the DEL experiments can be provided to the synthon modeling system 130. In various embodiments, the DEL experiments 115 for modeling covariates can be performed more than once. For example, technical replicates of the DEL experiments 115 for modeling covariates can be performed. In particular embodiments, at least three replicates of the DEL experiments 115 for modeling covariates can be performed.

The DEL outputs (e.g., DEL output 120A and/or DEL output 120B) from each of the DEL experiments can include DEL readouts for the small molecule compounds of the DEL experiment. In various embodiments, a DEL output can be a DEL count for the small molecule compounds of the DEL experiment. Thus, small molecule compounds that are putative binders of a target would have higher DEL counts in comparison to small molecule compounds that are not putative binders of the target. As an example, a DEL count can be a unique molecular index (UMI) count determined through sequencing. As an example, a DEL count may be the number of counts observed in a particular index of a solid-state media (e.g., a gel). In various embodiments, a DEL output can be DEL reads corresponding to the small molecule compounds. For example, a DEL read can be a sequence read derived from the tag that labeled a corresponding small molecule compound. In various embodiments, a DEL output can be a DEL index. For example, a DEL index can refer to a slice number of a solid-state media (e.g., a gel) which indicates how far a DEL member traveled down the solid state media.

Generally, the synthon modeling system 130 generates molecular embeddings from a plurality of synthons that are transformed from factorized synthons and further trains and/or deploys machine learning models. Such machine learning models are trained to learn latent binding affinity of compounds for targets and one or more covariates (e.g., load/replicate bias). This leads to improved predictions by the machine learning models in the form of higher enrichment scores, which are well-correlated with compound-target binding affinity. Thus, such machine learning models trained and/or deployed by the synthon modeling system 130 are useful for predicting anticipated target binding in virtual compound screening campaigns.

Figure 2:
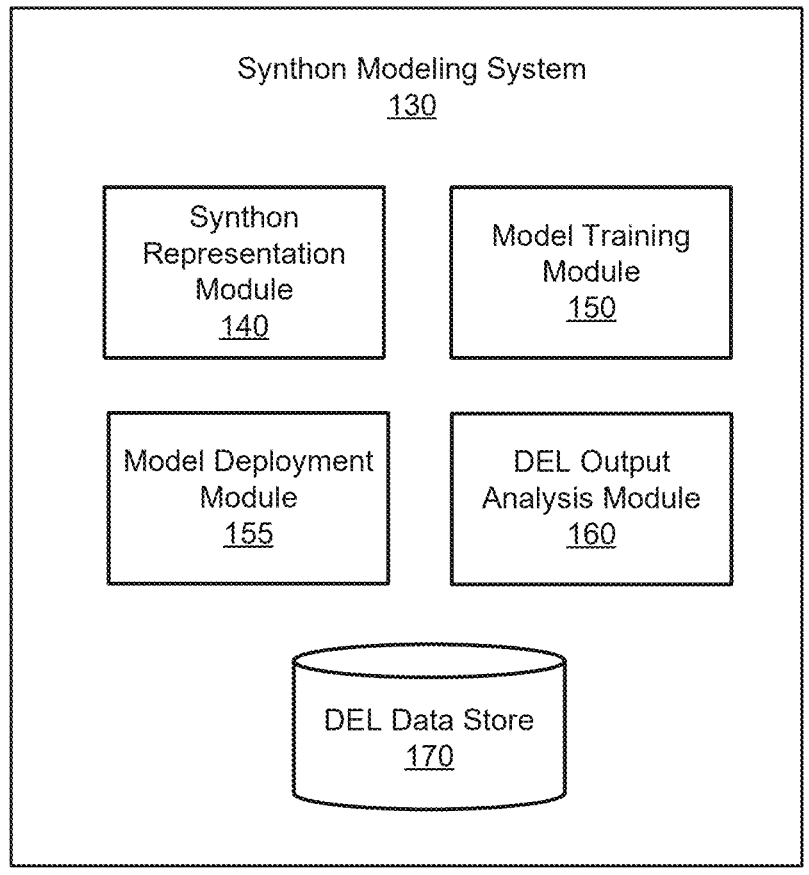
FIG. 2 depicts a block diagram of a synthon modeling system, in accordance with an embodiment.

FIG. 2 depicts a block diagram of the synthon modeling system 130, in accordance with an embodiment. FIG. 2 introduces individual components of the synthon modeling system 130, examples of which include a synthon representation module 140, a model training module 150, a model deployment module 155, a DEL output analysis module 160, and a DEL data store 170.

Referring to the synthon representation module 140, it generates representations of synthons (e.g., derived from synthons from compounds or derived from training synthons from training compounds). In various embodiments, the synthon representation module 140 generates a representation of a synthon by obtaining a plurality of factorized synthons of a compound. Here, a synthon of a compound can be represented as an encoding, such as a fingerprint, a graph of the synthon, or a 3-D point cloud. An example fingerprint of a synthon can be expressed as a Morgan fingerprint or a subunit of a Morgan fingerprint. Additional example encodings of the synthon can be expressed in a particular structure, such as any of a simplified molecular-input line-entry system (SMILES) string, MDL Molfile (MDL MOL), Structure Data File (SDF), Protein Data Bank (PDB), Molecule specification file (xyz), International Union of Pure and Applied Chemistry (IUPAC) International Chemical Identifier (InChI), and Tripos Mol2 file (mol2) format. In various embodiments, the synthon representation module 140 generates a plurality of synthon representations by transforming the plurality of synthons. In various embodiments, the synthon representation module 140 applies one or more machine learning models, referred to herein as learned representation models, to transform the plurality of synthons into plurality of synthon representations. In various embodiments, the one or more learned representation models are neural networks, such as multilayer perceptrons (MLPs). Further details of the methods performed by the synthon representation module 140 are described herein.

Referring to the model training module 150, it trains machine learning models using a training dataset. Generally, the model training module 150 trains machine learning models to effectively denoise DEL experimental data to generate target enrichment predictions representing binding between compounds and targets. In particular embodiments, the model training module 150 trains machine learning models to effectively denoise DEL experimental data in view of one or both of load bias and replicate bias to improve target enrichment predictions. Thus, the methods disclosed herein involve training machine learning models to generate target enrichment predictions that are better correlated with binding measurements in comparison to prior works. Further details of the training processes performed by the model training module 150 are described herein.

Referring to the model deployment module 155, it deploys machine learning models to generate target enrichment predictions representing binding between compounds and targets. The target enrichment predictions are useful for various applications, such as for performing a virtual compound screen, for selecting and analyzing hits, and for identifying common binding motifs on targets (e.g., protein targets). Further details of the processes performed by the model deployment module 155 are described herein.

Referring to the DEL output analysis module 160, it analyzes the outputs of one or more trained machine learned models. In various embodiments, the DEL output analysis module 160 translates predictions outputted by a machine learned model to a value representing a measure of binding between a compound and a target. As a specific example, the DEL output analysis module 160 may translate a target enrichment prediction outputted by a machine learning model to a binding affinity value. In various embodiments, the DEL output analysis module 160 ranks compounds according to at least their target enrichment predictions or according to the measure of binding. In various embodiments, the DEL output analysis module 160 identifies candidate compounds that are likely binders of a target based on the target enrichment prediction outputted by a machine learned model. For example, candidate compounds may be highly ranked compounds according to their target enrichment predictions or according to their measure of binding. Thus, candidate compounds can be synthesized e.g., as part of a medicinal chemistry campaign, and experimentally screened against the target to validate its binding and effects. In various embodiments, the DEL output analysis module 160 identifies common binding motifs in the binders that likely contribute towards effective binding between the binders and the target. This enables identification of valuable binding motifs that can be further incorporated into the design of additional compounds to achieve desired activity. Further details of the processes performed by the DEL output analysis module 160 are described herein.

Example Methods for Generating Target Enrichment Predictions

As described herein, methods for generating target enrichment predictions involve training and/or deploying machine learning models that analyze molecular embeddings derived from factorized synthons. Machine learning models are further trained to denoise the target enrichment predictions by accounting for effects of one or more covariates. Thus, machine learning models are capable of generating target enrichment predictions that better correlate with experimental binding affinity measurements. In various embodiments the experimental binding affinity measurements encompass any known method of measuring compound binding affinity to a biological target (e.g. DNA, RNA, and/or protein). Example experimental methods include, but are not limited to, fluorescent polarization, plasmon resonance/surface plasmon resonance (SPR), Enzyme-linked immunosorbent assay (ELISA), isothermal titration calorimetry (ITC), radioligand binding assay, Fluorescence Resonance Energy Transfer (FRET) assay, and/or Equilibrium dialysis.

Figure 3A:
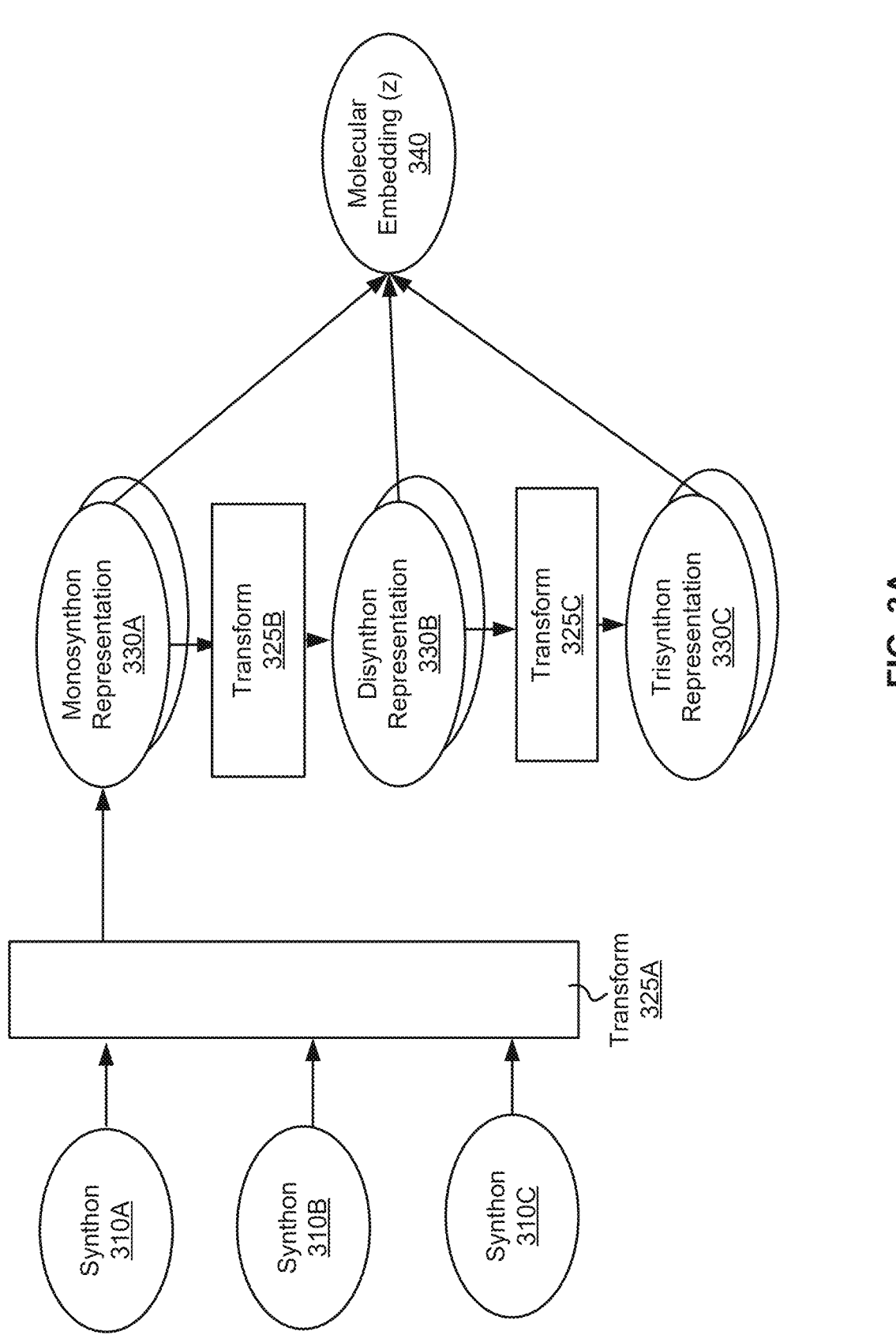
FIG. 3A depicts a flow diagram for analyzing factorized synthons to generate a molecular embedding, in accordance with an embodiment.
Figure 3B:
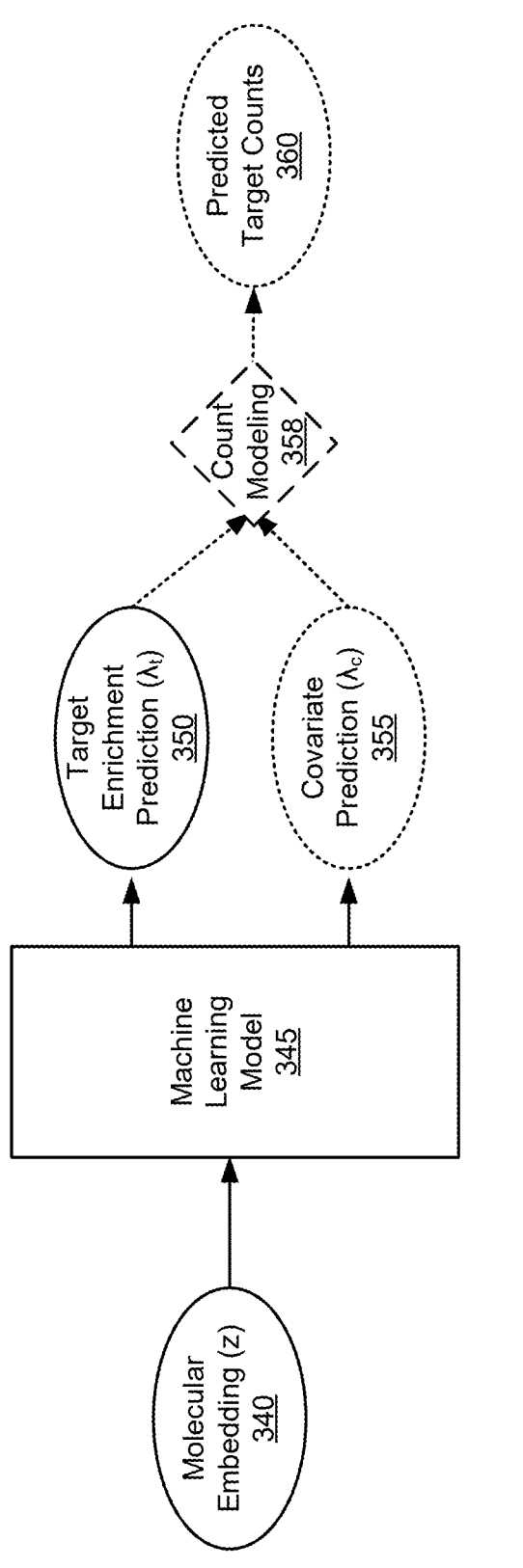
FIG. 3B depicts a flow diagram showing the implementation of a machine learning model, for predicting experimental counts for a DEL, in accordance with an embodiment.

Reference is now made to FIGS. 3A and 3B. Specifically, FIG. 3A depicts a flow diagram for analyzing factorized synthons to generate a molecular embedding, in accordance with an embodiment. Additionally, FIG. 3B depicts a flow diagram showing the implementation of a machine learning model, for predicting experimental counts for a DEL, in accordance with an embodiment. In various embodiments, the steps of the flow diagram shown in FIG. 3A can be performed by the synthon representation module 140.
Methods for Generating Molecular Representations FIG. 3A begins with a plurality of synthons e.g., synthon 310A, 310B, 310C. The plurality of synthons may be synthons of a compound. For example, the plurality of synthons may be a subset of the synthons of a compound. As another example, the plurality of synthons are all the synthons of a compound. The compound may be included as a part of a virtual library of compounds for performing a molecular screen (e.g., a virtual molecular screen) against a target. In various embodiments, the target can be a protein target. In particular embodiments, the target can be a human protein target. The protein target may be implicated in disease and therefore, the virtual molecular screen is useful for identifying candidate compounds that can bind to the protein target and modulate its behavior in disease. As one specific example, the protein target may be a human carbonic anhydrase IX (CAIX) protein target. As another specific example, the protein target may be a horseradish peroxidase (HRP) protein target. As another specific example, the protein target may be a discoidin domain receptor tyrosine kinase 1 (DDR1) protein target. As another specific example, the protein target may be mitogen-activated protein kinase 14 (MAPK14) protein target. However, as one of skill in the art would appreciate, other known target proteins can be used.

Although FIG. 3A explicitly depicts three synthons 310A, 310B, and 310C, in various embodiments, there may be fewer or additional synthons. Thus, the following description can similarly be applicable to embodiments in which there may be fewer (e.g., one synthon or two synthons) or additional synthons (e.g., four synthons, five synthons, six synthons, seven synthons, eight synthons, nine synthons, ten synthons, eleven synthons, twelve synthons, thirteen synthons, fourteen synthons, fifteen synthons, sixteen synthons, seventeen synthons, eighteen synthons, nineteen synthons, or twenty or more synthons). As discussed herein, by handling a compound at the synthon level (e.g., in the form of factorized synthons) the process avoids performing a step of enumerating the compound from the plurality of synthons, which is often a costly and error-prone process.

Generally, the plurality of synthons 310 are transformed into a plurality of synthon representations. For example, the plurality of synthons 310 undergo one or more transformations to generate the plurality of synthon representations. In various embodiments, transforming the plurality of synthons into a plurality of synthon representations comprises transforming the plurality of synthons using at least two transformations, at least three transformations, at least four transformations, at least five transformations, at least six transformations, at least seven transformations, at least eight transformations, at least nine transformations, at least ten transformations, at least eleven transformations, at least twelve transformations, at least thirteen transformations, at least fourteen transformations, at least fifteen transformations, at least sixteen transformations, at least seventeen transformations, at least eighteen transformations, at least nineteen transformations, or at least twenty transformations. In particular embodiments, transforming the plurality of synthons into a plurality of synthon representations comprises transforming the plurality of synthons using two transformations. In particular embodiments, transforming the plurality of synthons into a plurality of synthon representations comprises transforming the plurality of synthons using three transformations. In particular embodiments, transforming the plurality of synthons into a plurality of synthon representations comprises transforming the plurality of synthons using four transformations.

In various embodiments, one or more of the transformations involves applying a learned representation model. In various embodiments, each of the transformations involves applying a learned representation model. In various embodiments, a learned representation model used for a first transformation is a different learned representation model used for another transformation. In various embodiments, every learned representation model used for a transformation is different from another learned representation model used for another transformation. In various embodiments, a learned representation model is a neural network. In particular embodiments, a learned representation model is a multilayer perceptron (MLP).

In various embodiments, transforming the plurality of synthons into a plurality of synthon representations comprises generating one or more monosynthon representations from the plurality of synthons. In various embodiments, transforming the plurality of synthons into a plurality of synthon representations comprises generating one or more disynthon representations. In various embodiments, transforming the plurality of synthons into a plurality of synthon representations comprises generating one or more trisynthon representations. In various embodiments, transforming the plurality of synthons into a plurality of synthon representations comprises generating one or more tetrasynthon representations. In various embodiments, generating one or more monosynthon representations from the plurality of synthons comprises analyzing the plurality of synthons using a learned representation model. In various embodiments, generating one or more disynthon representations from the one or more monosynthon representations comprises analyzing the one or more monosynthon representations using a learned representation model. In various embodiments, generating one or more trisynthon representations from the one or more disynthon representations comprises analyzing the one or more disynthon representations using a learned representation model.

In various embodiments, the plurality of synthons are transformed into a plurality of synthon representations, which include one or more monosynthon representations, one or more disynthon representations, and one or more trisynthon representations. In various embodiments, the plurality of synthon representations include three monosynthon representations, three disynthon representations, and one trisynthon representation.

Returning to FIG. 3A, the plurality of synthons 310 undergo a hierarchical transformation process to generate a plurality of synthon representations. By doing so, this methodology capitalizes on the inherent hierarchical structure of molecules (in the form of their synthons). Here, the plurality of synthon representations includes monosynthon representations 330A, disynthon representations 330B, and trisynthon representations 330C. One skilled in the art would understand that in additional embodiments, there may be additional synthon representations (e.g., tetrasynthon representations, pentasynthon representations, etc.).

The plurality of synthons 310 undergo a first transform 325A to generate a plurality of monosynthon representations 330A. Here, monosynthon representations 330A may represent the synthon building blocks of the compound. In various embodiments, the number of monosynthon representations 330A equals the number of synthons in the plurality of synthons 310. For example, if there are three synthons 310, then there may be a corresponding three monosynthon representations 330A.

In various embodiments, the first transform 325A involves applying a learned representation model, such as a multilayer perceptron. In various embodiments, the first transform 325A of the plurality of synthons 310 to the monosynthon representations 330A can be expressed as:

$$z_\sigma = f(x_\sigma) \forall\ \sigma \in \{a, b, c\}$$

where a, b, c refer to synthons at a first, second, and third positions, respectively, $z_\sigma$ is a monosynthon embedding.

The monosython representations 330A are further transformed through a second transform 325B to generate disynthon representations 330B. Here, disynthon representations 330B may represent disynthons (e.g., two synthons) of the compound. In various embodiments, the disynthon representations 330B include one, two, three, four, or five representations. In various embodiments, the disynthon representations 330B include two representations. For example, given sythons a, b, c, the disynthon representations 330B may include a first disynthon representation $z_{ab}$ and a second disynthon representation $z_{bc}$. In various embodiments, the disynthon representations 330B include three representations. For example, given sythons a, b, c, the disynthon representations 330B may include a first disynthon representation $z_{ab}$, a second disynthon representation $z_{bc}$, and a third disynthon representation $z_{ac}$.

In various embodiments, the second transform 325B involves applying a learned representation model, such as a multilayer perceptron. In various embodiments, the second transform 325B of the plurality of monosynthon representations 330A to the disynthon representations 330B can be expressed as:

$$z_{ab} = MLP([z_a; z_b])$$
$$z_{bc} = MLP([z_b; z_c])$$
$$z_{ac} = MLP([z_a; z_c])$$

where a, b, c refer to synthons at a first, second, and third positions, respectively, and $z_{ab}$, $z_{bc}$, $z_{ac}$ represent disynthon embeddings.

The disynthon representations 330B are further transformed through a third transform 325C to generate trisynthon representations 330C. Here, trisynthon representations 330C represent trisynthons (e.g., three synthons) of the compound. In various embodiments, the trisynthon representations 330A include one, two, three, four, or five representations. In various embodiments, the trisynthon representations 330C include one representation. For example, given sythons a, b, c, the trisynthon representation 330C may include a trisynthon representation $z_{abc}$. In various embodiments, the trisynthon representations 330C include more than one representation. For example, given sythons a, b, c, d, the trisynthon representations 330C may include a first trisynthon representation $z_{abc}$ and a second trisynthon representation $z_{bcd}$.

In various embodiments, the third transform 325C involves applying a learned representation model, such as a multilayer perceptron. In various embodiments, the third transform 325C of the plurality of disynthon representations 330B to the trisynthon representations 330C can be expressed as:

$$z_{abc} = MLP([z_{ab}; z_{bc}; z_{ac}])$$

where a, b, c refer to synthons at a first, second, and third positions, respectively, and $z_{abc}$ represents a trisynthon embedding.

In some embodiments, third transform 325C considers only a subset of all the disynthon representations 330B. For example, the third transform 325C can be expressed as:

$$z_{abc} = MLP([z_{ab}; z_c;])$$

where a, b, c refer to synthons at a first, second, and third positions, respectively, and $z_{abc}$ represents a trisynthon embedding.

Although not shown in FIG. 3A, one or more additional transformations can be performed to generate additional higher order synthon representations. As used herein, higher order synthon representations refer to synthon representations representing larger numbers of synthons. For example, a trisynthon representation would be a higher order representation in comparison to a disynthon representation.

The plurality of synthon representations, which in FIG. 3A includes the monosynthon representations 330A, the disynthon representations 330B, and the trisynthon representations 330C, are combined to generate the molecular embedding (z) 340. In various embodiments, combining the synthon representations comprises applying a model to generate the molecular embedding (z) 340. In various embodiments, combining the synthon representations comprises applying a feed-forward model, such as a feed-forward neural network, to generate the molecular embedding (z) 340. In various embodiments, combining the synthon representations comprises applying a recurrent model, such as a recurrent neural network, to generate the molecular embedding (z) 340. For example, combining the synthon representations may include inputting two monosynthon representations 330A to the recurrent model, followed by further inputting a third monosynthon representation to the recurrent model.

In various embodiments, combining the synthon representations comprises aggregating the synthon representations, followed by applying a model to the aggregated synthon representations to generate the molecular embedding (z) 340. For example, combining the synthon representations comprises aggregating the synthon representations and applying a multi-layer perceptron to the aggregated synthon representations.

In various embodiments, combining the plurality of synthon representations into a molecular embedding includes implementing a multi-head attention mechanism across the plurality of synthon representations. In various embodiments, implementing the multi-head attention mechanism comprises using one or more learned attention weights of the plurality of synthon representations. Here, the learned attention weights of the plurality of synthon representations may be useful for identifying which synthon representations are playing a role in the binding of the compound. For example, synthon representations that are assigned higher weights may be deemed to be contributing more towards the binding of the compound to the target whereas synthon representations that are assigned lower weights may be deemed to be contributing less towards the binding of the compound to the target. In various embodiments, the one or more learned attention weights are used to rank the plurality of synthons (corresponding to synthon representations) for their ability to bind to the target.

In various embodiments, the molecular embedding (z) 340 can be expressed as:

$$z = \text{Multihead} - \text{Attention}([z_a; z_b; z_c; z_{ab}; z_{bc}; z_{ac}; z_{abc}])$$

Figure 4A:
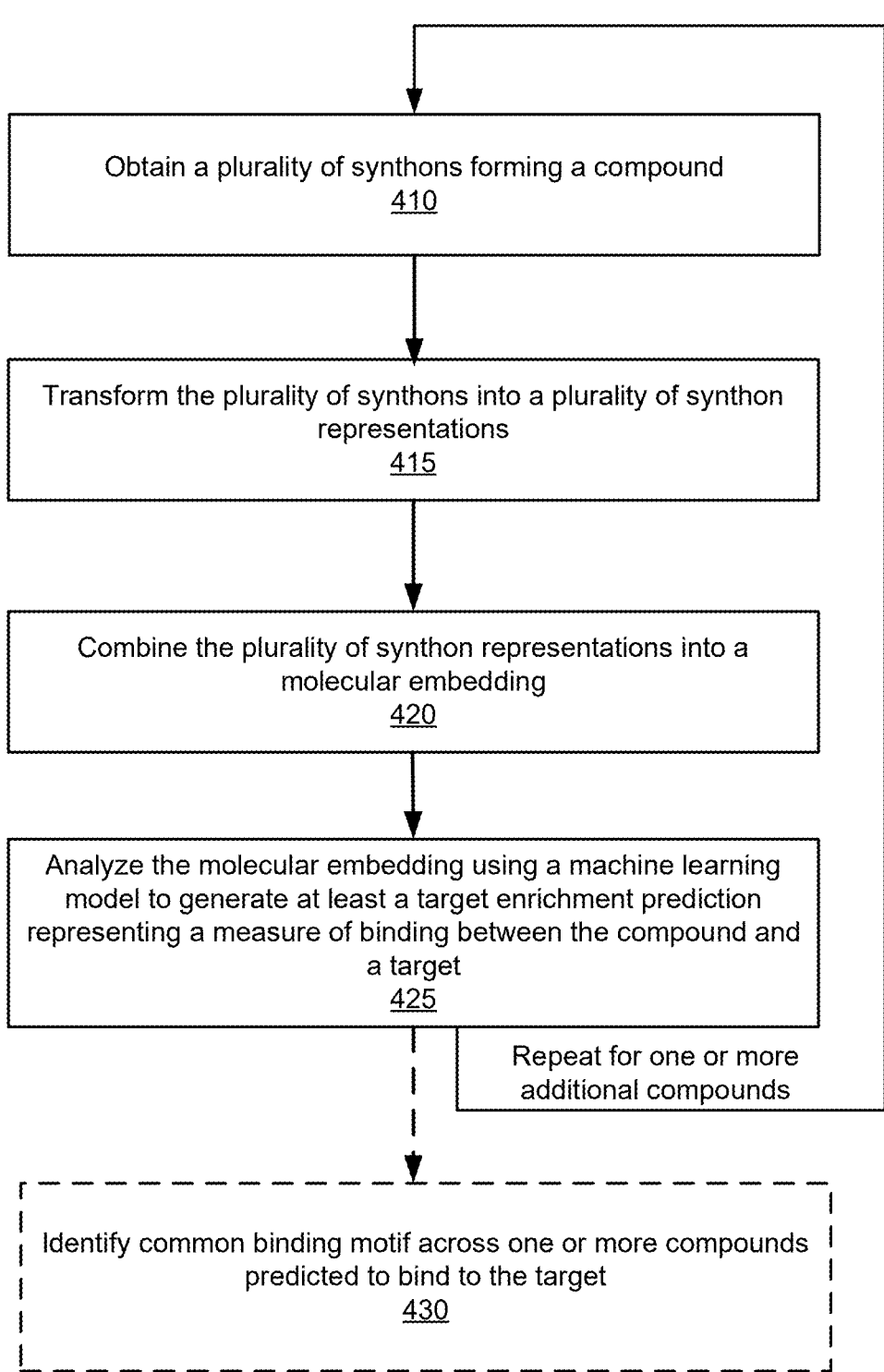
FIG. 4A depicts an example flow process for generating target enrichment predictions, in accordance with an embodiment.
Figure 4B:
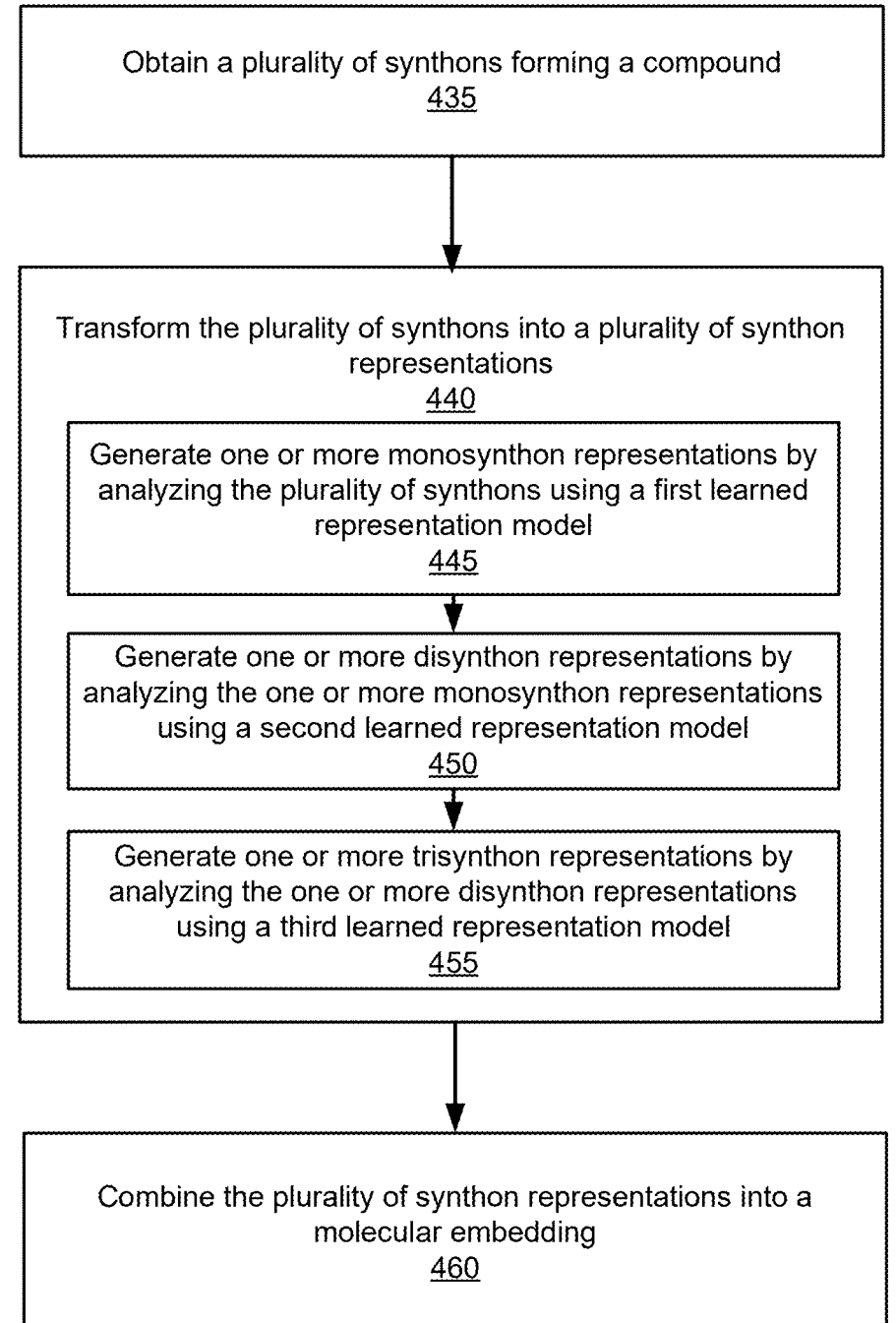
FIG. 4B depicts an example flow process for generating molecular representations, in accordance with an embodiment.

Reference is now made to FIG. 4B, which depicts an example flow process for generating molecular representations, in accordance with an embodiment. Step 435 involves obtaining a plurality of synthons forming a compound.

Step 440 involves transforming the plurality of synthons into a plurality of synthon representations. In various embodiments, step 440 involves performing a hierarchical transformation in which higher order synthon representations are hierarchically constructed from lower order synthon representations.

As shown in FIG. 4B, step 440 can involve multiple substeps, such as step 445, 450, and 455. Specifically, step 445 involves generating one or more monosynthon representations by analyzing the plurality of synthons using a first learned representation model. Step 450 involves generating one or more disynthon representations by analyzing the one or more monosynthon representations using a second learned representation model. Then, step 455 involves generating one or more trisynthon representations by analyzing the one or more disynthon representations using a third learned representation model.

Step 460 involves combining the plurality of synthon representations (e.g., monosynthon, disynthon, trisynthon representations) to generate a molecular embedding.

Example Methods for Generating Target Enrichment Prediction

Methods disclosed herein further encompass generating a target enrichment prediction using e.g., molecular embeddings. Referring next to FIG. 3B, the molecular embedding (z) 340 can be provided as input to a machine learning model 345. Here, the machine learning model 345 is trained to generate a target enrichment prediction ($\lambda_r$) 350, representing a measure of binding between the compound and the target. Specifically, the target enrichment prediction 350 is a prediction learned by the machine learning model 345. For example, the target enrichment prediction 350 represents a prediction of binding between a compound and a target that is denoised (e.g., absent influence from covariates and other sources of noise).

In various embodiments, the machine learning model 345 further generates one or more covariate predictions ($\lambda_c$) 355. The covariate prediction 355 refers to a learned prediction of the effects of one or more covariates (e.g., sources of noise in DEL experiments). For example, the covariate prediction can be a learned prediction of the effects from one or more covariates comprising any of non-specific binding (e.g., as determined from controls) and/or other target data (e.g., binding to beads, binding to streptavidin of the beads, binding to biotin, binding to gels, binding to DEL container surfaces) or other sources of noise, such as, load bias, replicate bias, starting tag imbalance, experimental conditions, chemical reaction yields, side and truncated products, errors from the library synthesis, DNA affinity to target, sequencing depth, and sequencing noise such as PCR bias. In particular embodiments, the covariate prediction arises from load bias. In particular embodiments, the covariate prediction arises from replicate noise.

Although FIG. 3B only shows a single covariate prediction ($\lambda_c$) 355, in various embodiments, the machine learning model 345 may be trained to predict two or more covariate predictions ($\lambda_c$) 355 that each represent a learned prediction of the effects of a particular covariate. In particular embodiments, the machine learning model 345 is trained to predict two covariate predictions ($\lambda_c$) 355. For example, a first covariate prediction arises from load bias, and the second covariate prediction arises from replicate bias.

In various embodiments, all of the steps shown in FIG. 3B pertaining to the machine learning model 345 may be performed during both training of the machine learning model 345 and during deployment of the machine learning model 345. However, in some embodiments, as indicated in FIG. 3B by the dotted lines, certain steps shown in FIG. 3B may only be performed when training the machine learning model 345 and need not be performed during deployment of the machine learning model 345. For example, the machine learning model 345 need not generate covariate prediction (Ae) during deployment of the machine learning model 345 and is only generated during training of the machine learning model 345. In this scenario, the covariate prediction 355, the count modeling 358, and the predicted target counts 360 need not be generated. In various embodiments, during deployment of the machine learning model 345, the covariate prediction (Ae) 355 is generated but is discarded and need not be used. In such embodiments, the predicted target counts 360 are not generated.

As shown in FIG. 3B, the target enrichment prediction 350 may, in various embodiments, be directly outputted by the machine learning model 345. Generally, the target enrichment prediction 350 represents a measure of binding between the compound and the target. The target enrichment prediction 350 may be used to calculate a binding affinity value for the compound-target complex. In various embodiments, the target enrichment prediction 350 can be converted to a binding affinity value. In various embodiments, the binding affinity value is measured by an equilibrium dissociation constant ($K_d$). In various embodiments, a binding affinity value is measured by the negative log value of the equilibrium dissociation constant ($pK_d$). In various embodiments, a binding affinity value is measured by an equilibrium inhibition constant ($K_i$). In various embodiments, a binding affinity value is measured by the negative log value of the equilibrium inhibition constant ($pK_i$). In various embodiments, a binding affinity value is measured by the half maximal inhibitory concentration value (IC50). In various embodiments, a binding affinity value is measured by the half maximal effective concentration value (EC50). In various embodiments, a binding affinity value is measured by the equilibrium association constant ($K_a$). In various embodiments, a binding affinity value is measured by the negative log value of the equilibrium association constant ($K_a$). In various embodiments, a binding affinity value is measured by a percent activation value. In various embodiments, a binding affinity value is measured by a percent inhibition value.

In various embodiments, the target enrichment prediction 350 is converted to a binding affinity value according to a pre-determined conversion relationship. The pre-determined conversion relationship may be determined using DEL experimental data such as previously generated DEL outputs (e.g., DEL output 120A and 120B shown in FIG. 1A) based on DEL experiments. In various embodiments, the pre-determined conversion relationship is a linear equation. Here, the target enrichment prediction 350 may be correlated to the binding affinity value. In various embodiments, the pre-determined conversion relationship is any of a linear, exponential, logarithmic, non-linear, or polynomial equation.

In various embodiments, target enrichment prediction 350 can be used to rank order compounds. For example, a first compound with a target enrichment prediction that is correlated with a stronger binding affinity to a target can be ranked higher than a second compound with a target enrichment prediction that is correlated with a weaker binding affinity to the target. Generally, in a medicinal chemistry campaign such as hit-to-lead optimization, binding affinity values are commonly used to assess and select the next compounds to be synthesized. Thus, the target enrichment prediction, which correlates to binding affinity values, can be useful for rank ordering compounds and hence be used directly to guide design.

In various embodiments, the ranking of the compounds uses the target enrichment prediction 350 as well as a probability obtained from a probability density function. In various embodiments, the probability density function is any one of a Poisson distribution, Binomial distribution, Gamma distribution, Binomial-Poisson distribution, or negative binomial distribution. In particular embodiments, the probability density function is a Poisson distribution. In particular embodiments, the Poisson distribution is a zero-inflated Poisson distribution. As discussed further herein, the probability density function may be a learned distribution for modeling DEL counts (e.g., target counts or control counts). The probability obtained from the probability density function may be a predicted zero-probability p. Here, p is a parameter of the probability distribution. Thus, the ranking of the compounds may be determined according to a metric $\varepsilon$, which is expressed as $\varepsilon = p * \lambda$, where $\lambda$ represents the target enrichment prediction 350.

In various embodiments, the rank ordering of compounds is used to identify binders and non-binders. In various embodiments, identifying binders includes identifying the top Z compounds in the ranked list as binders. Compounds not included in the top Z compounds are considered non-binders. In various embodiments, the top Z compounds refers to any of the top 5 compounds, top 10 compounds, top 20 compounds, top 30 compounds, top 40 compounds, top 50 compounds, top 75 compounds, top 100 compounds, top 200 compounds, top 300 compounds, top 400 compounds, top 500 compounds, top 1000 compounds, or top 5000 compounds.

In various embodiments, compounds that are identified as binders to a target can be further analyzed to characterize the binders. In various embodiments, binders can be defined as compounds that have predicted binding affinity above a threshold binding value. In one scenario, binders are analyzed to identify common binding motifs in the binders that likely contribute towards effective binding between the binders and the target. In various embodiments, common binding motifs refer to chemical groups that appear in at least X % of the binders. In various embodiments, X % is at least 10% of binders, at least 20% of binders, at least 30% of binders, at least 40% of binders, at least 50% of binders, at least 60% of binders, at least 70% of binders, at least 80% of binders, at least 90% of binders, or at least 95% of binders. In various embodiments, X % is 100% of binders.

As a specific example, a target protein can be a human carbonic anhydrase IX (CAIX) protein. However, as one of skill in the art would appreciate, other known target proteins can be used. Using the methods described herein, compounds that bind to the target protein can be identified based on target enrichment predictions 350 generated by machine learning models. A binding motif that is commonly present in many of the compounds predicted to bind to the target protein (e.g., binders) can be a benzenesulfonamide group.

Reference is now made to FIG. 4A, which depicts an example flow process for generating target enrichment predictions, in accordance with an embodiment.

Step 410 involves obtaining a plurality of synthons forming a compound.

Step 415 involves transforming the plurality of synthons into a plurality of synthon representations.

Step 420 involves combining the plurality of synthon representations into a molecular embedding 420.

Step 425 involves analyzing the molecular embedding using a machine learning model to generate at least a target enrichment prediction representing a measure of binding between the compound and a target. Generally, the machine learning model is trained to predict the target enrichment prediction which represents a prediction that is denoised to account for one or more covariate predictions (e.g., absent influence from covariates and other sources of noise).

As shown in FIG. 4A, the steps 410, 415, 420, and 425 can be repeated for one or more additional compounds to generate target enrichment predictions for each of the or more additional compounds. Thus, compounds that bind to the target (e.g., binders) can be readily identified. Thus, virtual compound screens can be efficiently performed by repeating steps 410, 415, 420, and 425 at a large scale or in a high-throughput manner.

Optionally, step 430 involves identifying a common binding motif across one or more compounds that are predicted to bind to the target.

Example Methods for Generating Predicted Target Counts

Additionally disclosed herein are methods for generating predicted target counts e.g., of a DEL. Generally, methods for generating predicted target counts involve implementing a machine learning model and one or more probability density functions for modeling the target counts. For example, methods for generating predicted target counts of a DEL may involve analyzing a molecular embedding using a trained machine learning model that is trained to output a target enrichment prediction and one or more covariate predictions. The target enrichment prediction and the one or more covariate predictions are further analyzed e.g., using one or more probability density functions, to model at least experimental target counts of a DEL.

Reference is again made to FIG. 3B, which is an exemplary flow process for generating predicted target counts 360 of a DEL. Here, the predicted target counts 360 may be a predicted DEL output for a DEL panning experiment. For example, the predicted target counts 360 may represent a DEL output of one or more DEL panning experiments, examples of which include a prediction of DEL counts and/or mean counts across multiple replicates of DEL panning experiments. Here, the predicted target counts 360 is a prediction of DEL counts in which various covariates, such as off-target binding or noise (e.g., background, matrix, covariates) are included. Thus, for a given DEL panning experiment, the flow process of FIG. 3B can be used to predict, in silico, the DEL counts that would be observed in the panning experiment.

FIG. 3B begins with a molecular embedding (z) 340, as previously described. The machine learning model 345 analyzes the molecular embedding (z) 340 and outputs the target enrichment prediction ($\lambda_t$) and one or more covariate predictions ($\lambda_c$) 355.

In various embodiments, the target enrichment prediction ($\lambda_t$) 350 and the covariate prediction ($\lambda_c$) 355 are combined to generate predicted target counts 360. As an example, combining the target enrichment prediction ($\lambda_t$) 350 and the covariate prediction ($\lambda_c$) 355 involves performing a count modeling 358. In various embodiments, the count modeling 358 step includes implementing a probability density function that is trained to model the predicted target counts 360. Thus, in the embodiment shown in FIG. 3B, the count modeling 358 would involve implementing a probability density function that is trained to model predicted target counts 360 of a DEL experiment that includes contributions from both binding between the compound and the target, as well as other covariates.

In various embodiments, the probability density function is represented by any one of a Poisson distribution, Binomial distribution, Gamma distribution, Binomial-Poisson distribution, or negative binomial distribution. In particular embodiments, the probability density function is a Poisson distribution. In particular embodiments, the Poisson distribution is a zero-inflated Poisson distribution.

Generally, the probability density function includes one or more learnable parameters (e.g., learned and/or tuned during training, which is further described herein). For example, the probability density function may include a parameter $\gamma$ which enables the probability density function to more accurately model the predicted target counts while accounting for covariates (e.g., noise/bias) in the DEL experiment.

In various embodiments, the predicted target counts 360 is expressed as:

$$c_t^j \sim ZIPoisson\left(l * \exp\left(\gamma_t^j\right) * \exp(\lambda_c * \lambda_t)\right)$$

where $$c_t^j$$

represents the predicted target counts of the jth replicate of the target, "ZIPoisson" represents a zero-inflated Poisson distribution, l is the normalized preselection count data (normalized to account for differences in sequencing depth across experiments), and $$\gamma_t^j$$

is a learned parameter of the zero-inflated Poisson distribution to account for covariates (e.g., load bias and/or replicate bias). Ae represents the covariate prediction 355 and $\lambda_t$ represents the target enrichment prediction 350.

Although not shown in FIG. 3B, one or more additional count modeling steps can be performed by implementing one or more additional probability density functions to model additional DEL counts. For example, an additional count modeling step can be performed by implementing an additional probability density function that analyzes the covariate prediction ($\lambda_c$) 355 and generates a predicted control counts. As used herein, "predicted control counts" refers to predicted DEL counts that arise due to one or more covariate factors. Thus, in such embodiments, implementing the additional probability density function enables modeling of the predicted quantity of DEL counts that are due to covariates. In various embodiments, these DEL counts from covariate effects can be discarded as they do not arise from binding between the compound and the desired target.

In various embodiments, the predicted control counts are expressed as:

$$c_c^i \sim ZIPoisson(l * \exp(\gamma_c^i) * \exp(\lambda_c))$$

where $$c_c^i$$

represents predicted control counts of the ith replicate of the covariate, "ZIPoisson" represents a zero-inflated Poisson distribution, l is the normalized preselection count data, and $$\gamma_c^j$$

is a learned parameter of the zero-inflated Poisson distribution, and $\lambda_c$ represents the covariate prediction 355.

In various embodiments, the machine learning model 345 outputs multiple covariate predictions 355 (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more covariate predictions). In such embodiments, the target enrichment prediction ($\lambda_t$) 350 is combined with the multiple covariate predictions 355 through the count modeling 358 to generate the predicted target counts 360. In various embodiments, additional probability density functions may be implemented for one or more of the multiple covariate predictions 355 to model the DEL counts that arise due to any of the corresponding covariate effects.

As described herein, in various embodiments multiple probability density functions can be implemented to generate the predicted target counts 360 as well as one or more additional DEL counts, such as one or more predicted control counts arising from covariates. In such embodiments, each of the multiple probability density functions can independently be one of a Poisson distribution, Binomial distribution, Gamma distribution, Binomial-Poisson distribution, or negative binomial distribution. In particular embodiments, each of the probability density functions is a Poisson distribution. In particular embodiments, each of the Poisson distributions is a zero-inflated Poisson distribution. In various embodiments, each of the multiple probability density functions include one or more learnable parameters $\gamma$ that are learned/tuned during training.

FIG. 4C depicts an example flow process for predicting experimental counts for a DEL, in accordance with an embodiment.

Step 485 involves obtaining a molecular embedding of a compound. As described herein, the molecular embedding may be generated from a plurality of synthon representations of the compound. Such synthon representations can be derived from factorized synthons of the compound and therefore, a compound enumeration step need not be performed.

Step 490 involves analyzing the molecular embedding using a machine learning model to generate (A) a target enrichment prediction representing a measure of binding between the compound and the target, and (B) one or more covariate predictions.

Step 495 involves combining the target enrichment prediction and the one or more covariate predictions to generate a predicted target counts by applying a probability density function that models the experimental target counts. In various embodiments, the probability density function is a Poisson distribution, such as a zero-inflated Poisson distribution.

Example Machine Learning Models

Embodiments disclosed herein involve training and/or deploying one or more machine learning models for generating predictions for any of a virtual screen, hit selection and analysis, or predicting binding affinity. For example, a machine learning model (e.g., machine learning model 345, as described in FIG. 3B) can be implemented to analyze molecular embeddings and to predict target enrichment predictions. In various embodiments, machine learning models described herein include learned representation models (e.g., learned representation models that perform transform 325A, 325B, 325C as described in FIG. 3A). For example, learned representation models may be neural networks, optionally multilayer perceptrons. In various embodiments, machine learning models described herein include models that use probability density functions (e.g., probability density functions for count modeling 358, as described in FIG. 3B) for modeling target or control counts. The following description regarding exemplary machine learning models can be applicable to any or all of the machine learning model (e.g., machine learning model 345, as described in FIG. 3B), the learned representation models (e.g., learned representation models that perform transform 325A, 325B, 325C as described in FIG. 3A), and/or the models that use probability density functions (e.g., probability density functions for count modeling 358, as described in FIG. 3B).

In various embodiments, machine learning models disclosed herein can be any one of a regression model (e.g., linear regression, logistic regression, or polynomial regression), decision tree, random forest, support vector machine, Naïve Bayes model, k-means cluster, or neural network (e.g., feed-forward networks, convolutional neural networks (CNN), deep neural networks (DNN), autoencoder neural networks, generative adversarial networks, attention based models, geometric neural networks, equivariant neural networks, or recurrent networks (e.g., long short-term memory networks (LSTM), bi-directional recurrent networks, deep bi-directional recurrent networks).

In particular embodiments, machine learning models disclosed herein are neural networks. For example, the machine learning model (e.g., machine learning model 345, as described in FIG. 3B) can be implemented as a neural network. As another example, the learned representation models (e.g., learned representation models that perform transform 325A, 325B, 325C as described in FIG. 3A) can be implemented as a neural network. As another example, the models that use probability density functions (e.g., probability density functions for count modeling 358, as described in FIG. 3B) can be implemented as neural networks.

In various embodiments, the machine learning models disclosed herein comprise a feedforward artificial neural network. For example, the machine learning model (e.g., machine learning model 345, as described in FIG. 3B) can be implemented as a feedforward artificial neural network. As another example, the learned representation models (e.g., learned representation models that perform transform 325A, 325B, 325C as described in FIG. 3A) can be implemented as a feedforward artificial neural network. As another example, the models that use probability density functions (e.g., probability density functions for count modeling 358, as described in FIG. 3B) can be implemented as feedforward artificial neural networks.

In various embodiments, the machine learning models disclosed herein comprise a multilayer perceptron. For example, the machine learning model (e.g., machine learning model 345, as described in FIG. 3B) can be implemented as a multilayer perceptron. As another example, the learned representation models (e.g., learned representation models that perform transform 325A, 325B, 325C as described in FIG. 3A) can be implemented as a multilayer perceptron. As another example, the models that use probability density functions (e.g., probability density functions for count modeling 358, as described in FIG. 3B) can be implemented as multilayer perceptrons.

In various embodiments, machine learning models disclosed herein can be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, gradient based optimization technique, and dimensionality reduction techniques such as manifold learning, principal component analysis, factor analysis, autoencoder, and independent component analysis, or combinations thereof. In various embodiments, the machine learning model is trained using supervised learning algorithms, unsupervised learning algorithms, semi-supervised learning algorithms (e.g., partial supervision), weak supervision, transfer, multi-task learning, or any combination thereof.

In various embodiments, machine learning models disclosed herein have one or more parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of a neural network, support vectors in a support vector machine, and coefficients in a regression model. The model parameters of the machine learning model are trained (e.g., adjusted) using the training data to improve the predictive power of the machine learning model.

Training Machine Learning Models

Embodiments disclosed herein describe the training of machine learning models that analyze molecular embeddings derived from factorized synthons. Generally, machine learning models are trained to generate target enrichment predictions, which represent the learned binding strength between compounds and targets. Thus, the target enrichment prediction can be useful for identifying and/or ranking potential binders e.g., in virtual compound screens. In various embodiments, the target enrichment prediction represents an intermediate prediction of a machine learning model. For example, the target enrichment prediction is learned by training the machine learning model to predict the experimentally observed target counts and/or experimentally observed control counts arising from background/matrix/covariates.

Generally, machine learning models described herein are trained using training synthons of training compounds with corresponding DNA-encoded library (DEL) outputs. Training synthons refer to factorized synthons of a training compound. As used herein, a training compound refers to a compound with known corresponding experimental counts generated through one or more DEL panning experiments. Thus, these experimental counts can represent ground truth values for training the machine learning model.

In various embodiments, training synthons of a training compound have a known corresponding experimental target count from a DEL panning experiment. The experimental target count may refer to signal in DEL data from a DEL experiment in which various sources of noise (e.g., background, matrix, covariates) are included. For example, the DEL experiment may include immobilizing protein targets on beads, exposing the protein targets to DEL compounds, washing the mixture to remove unbound compounds, and eluting, amplifying, and sequencing the tag sequences. Thus, the experimental target count obtained from this DEL experiment may include data arising from the various sources of noise.

In various embodiments, training synthons of a training compound have one or more known corresponding experimental control counts from a DEL panning experiment. The experimental control counts may refer to signal in DEL data from a DEL experiment in which only one or more sources of noise (e.g., background, matrix, covariates) are included. For example, a DEL experiment may model a covariate (e.g., non-specific binding to beads). This involves incubating small molecule compounds with beads without the presence of immobilized targets on the bead. The mixture is washed to remove non-binders, followed by elution, sequence amplification, and sequencing. Thus, the experimental control counts obtained from this DEL experiment includes data arising from the sources of noise but does not include data arising from actual binding of compounds and the target.

In various embodiments, training synthons of a training compound have both 1) one or more known corresponding experimental control counts from one or more additional DEL panning experiments and 2) a known corresponding experimental target count from a DEL panning experiment. Specifically, the corresponding DNA-encoded library (DEL) outputs for a training compound comprises: 1) experimental control counts arising from a covariate determined through a first panning experiment; and 2) experimental target counts determined through a second panning experiment. In such embodiments, both the experimental control counts and the experimental target counts can be used as reference ground truth values for training the machine learning model. For example, a machine learning model is trained to generate a target enrichment prediction by attempting to predict the experimental control counts and the experimental target counts observed for training compounds.

Generally, during a training iteration involving training synthons of a training compound, the methods for training the machine learning model involve obtaining a plurality of training synthons forming a training compound, transforming the plurality of training synthons into a plurality of training synthon representations, and combining the plurality of training synthon representations into a molecular embedding.

Here, the step of obtaining a plurality of training synthons forming a training compound may be performed in a similar or same manner as was described above in reference to synthons of a compound (e.g., as described in reference to the synthons 310A, 310B, 310C in FIG. 3A). The step of transforming the plurality of training synthons into a plurality of training synthon representations may be performed in a similar or same manner as was described above in reference to a compound (e.g., as described in reference to the transforms 325A, 325B, 325C in FIG. 3A). For example, the plurality of training synthons can be generated via a hierarchical transformation process, where higher order synthon representations are generated from lower order synthon representations. Additionally, the step of combining the plurality of training synthon representations into a molecular embedding may be performed in a similar or same manner as was described above in reference to the plurality of synthon representations (e.g., monosynthon representation 330A, disynthon representation 330B, and trisynthon representation 330C as described in FIG. 3A).

Furthermore, during a training iteration involving training synthons of the training compound, the machine learning model is implemented to analyze the molecular embedding to generate a target enrichment prediction and one or more covariate predictions. Here, this step may be performed in a similar or same manner as was described above in reference to a molecular embedding during deployment of the machine learning model (e.g., as described in reference to FIG. 3B regarding molecular embedding (z) 340).

Additionally, a training iteration involving the training compound further includes combining the target enrichment prediction and one or more covariate predictions to generate a predicted target counts. In various embodiments, combining the target enrichment prediction and the covariate prediction to generate a predicted target counts comprises applying a probability density function that models the predicted target counts. In various embodiments, the probability density functions are represented by any one of a Poisson distribution, Binomial distribution, Gamma distribution, Binomial-Poisson distribution, or Gamma-Poisson distribution. In particular embodiments, the probability density functions are represented by Poisson distributions. In various embodiments, the Poisson distributions are zero-inflated Poisson distributions.

In various embodiments, a training iteration involving the training compound further includes analyzing one or more covariate predictions to generate one or more predicted control counts. In various embodiments, generating one or more predicted control counts includes applying a probability density function that models the experimental control counts. In various embodiments, the probability density functions are represented by any one of a Poisson distribution, Binomial distribution, Gamma distribution, Binomial-Poisson distribution, or Gamma-Poisson distribution. In particular embodiments, the probability density functions are represented by Poisson distributions. In various embodiments, the Poisson distributions are zero-inflated Poisson distributions.

In various embodiments, a training iteration involving the training compound further includes analyzing two covariate predictions to generate two predicted control counts. For example, a first covariate prediction may account for a first covariate (e.g., load bias) and a second covariate prediction may account for a second covariate (e.g., replicate bias). In various embodiments, generating each predicted control count includes applying a probability density function that models a corresponding experimental control count. In various embodiments, the probability density functions are represented by any one of a Poisson distribution, Binomial distribution, Gamma distribution, Binomial-Poisson distribution, or Gamma-Poisson distribution. In particular embodiments, the probability density functions are represented by Poisson distributions. In various embodiments, the Poisson distributions are zero-inflated Poisson distributions.

Additionally, a training iteration involving the training compound further includes determining, according to a loss function, a loss value based on at least the predicted target counts and the experimental target counts. The loss value can then be used (e.g., backpropagated) to tune the parameters of at least the machine learning model to improve the predictions of the machine learning model. In various embodiments, the loss value is calculated using the predicted target counts and the experimental target counts. For example, the closer the predicted target counts are to the experimental target counts, the smaller the loss value. Thus, the machine learning model can be trained (e.g., parameters of the machine learning model are adjusted) to minimize the loss value.

In various embodiments, the loss value is calculated using the predicted control counts and the experimental control counts. For example, the closer the predicted control counts are to the experimental control counts, the smaller the loss value. In various embodiments, the loss value is calculated using predicted control counts and experimental control counts for a first covariate, as well as predicted control counts and experimental control counts for a second covariate. In various embodiments, the loss value is calculated using each of the predicted target counts, the experimental target counts, the one or more predicted control counts, and the one or more experimental control counts. In such embodiments, the closer the predicted target counts are to the experimental target counts and the closer each of the one or more predicted control counts are to the corresponding one or more experimental control counts, the smaller the loss value. In various embodiments, the loss value is determined by calculating a root mean squared error (RMSE) value. For example, the RMSE value may be calculated as the square root of the summation of 1) a difference between predicted target counts and experimental target counts and 2) differences between the one or more predicted control counts and the one or more corresponding experimental control counts.

In various embodiments, the loss value is determined according to probability density functions that model the experimental target counts and the experimental control counts. In various embodiments, the loss value is determined according to a first probability density function that models the experimental target counts and a second probability density function that models the experimental control counts.

In various embodiments, the probability density functions are represented by any one of a Poisson distribution, Binomial distribution, Gamma distribution, Binomial-Poisson distribution, or Gamma-Poisson distribution. In particular embodiments, the probability density functions are represented by Poisson distributions. In various embodiments, the Poisson distributions are zero-inflated Poisson distributions. Example zero-inflated Poisson (ZIP) distributions are described and implemented according to Equations (2) and (3) in the Examples below (e.g., for calculating $$c_c^i \text{ and } c_t^j,$$

respectively). In particular embodiments, Poisson distributions are characterized according to one or more parameters γ. Example parameters $$\gamma_c^i \text{ and } \gamma_t^j$$

of Poisson distributions are described according to Equations (2) and (3) in the Examples below.

In various embodiments, the loss function is any one of a negative log-likelihood loss, binary cross entropy loss, focal loss, arc loss, cosface loss, cosine based loss, or loss function based on a BEDROC metric. In particular embodiments, the loss function is a negative log-likelihood loss.

Figure 5A:
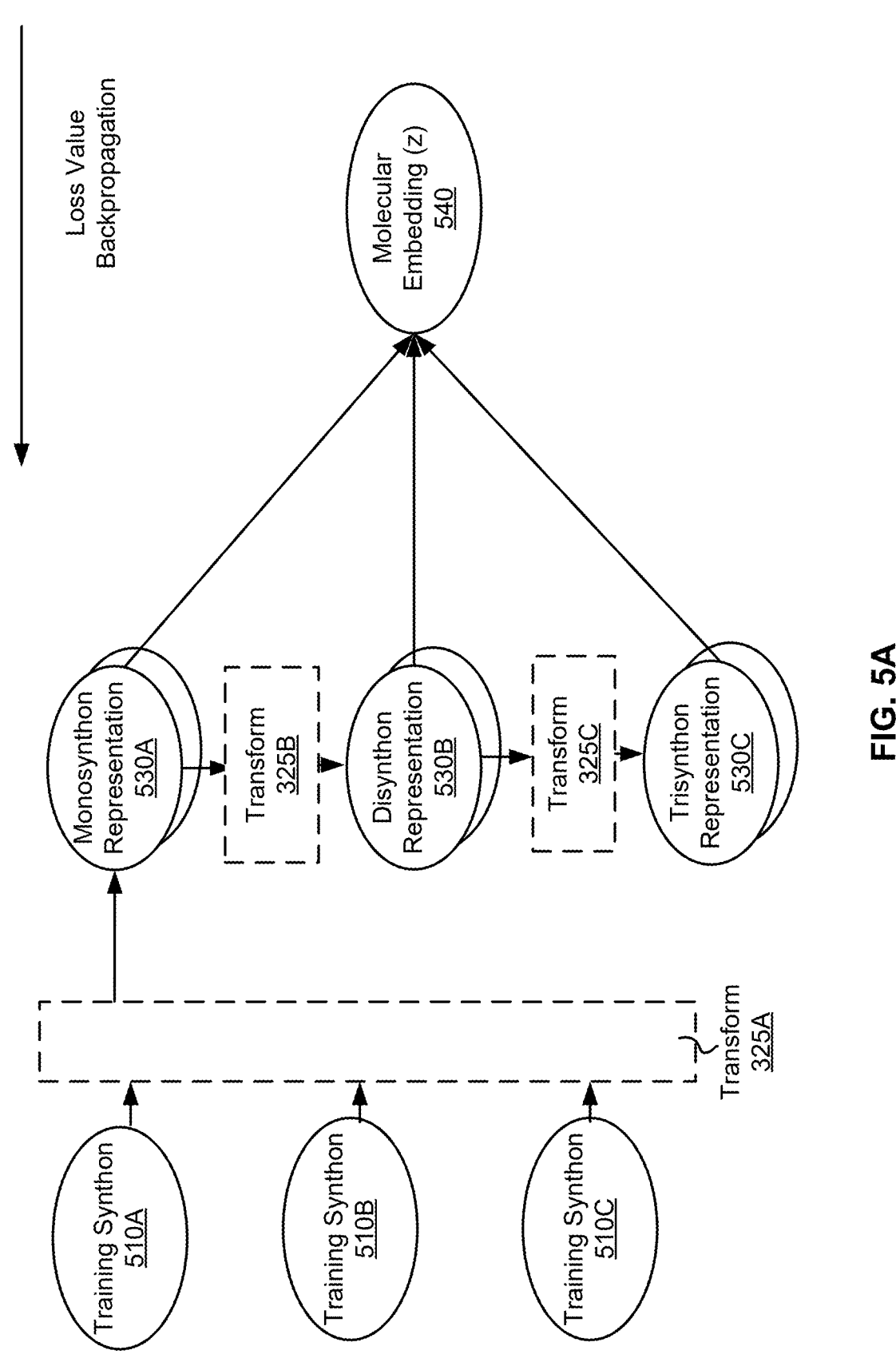
FIG. 5A depicts an example flow diagram for training the machine learning model, in accordance with an embodiment.
Figure 5B:
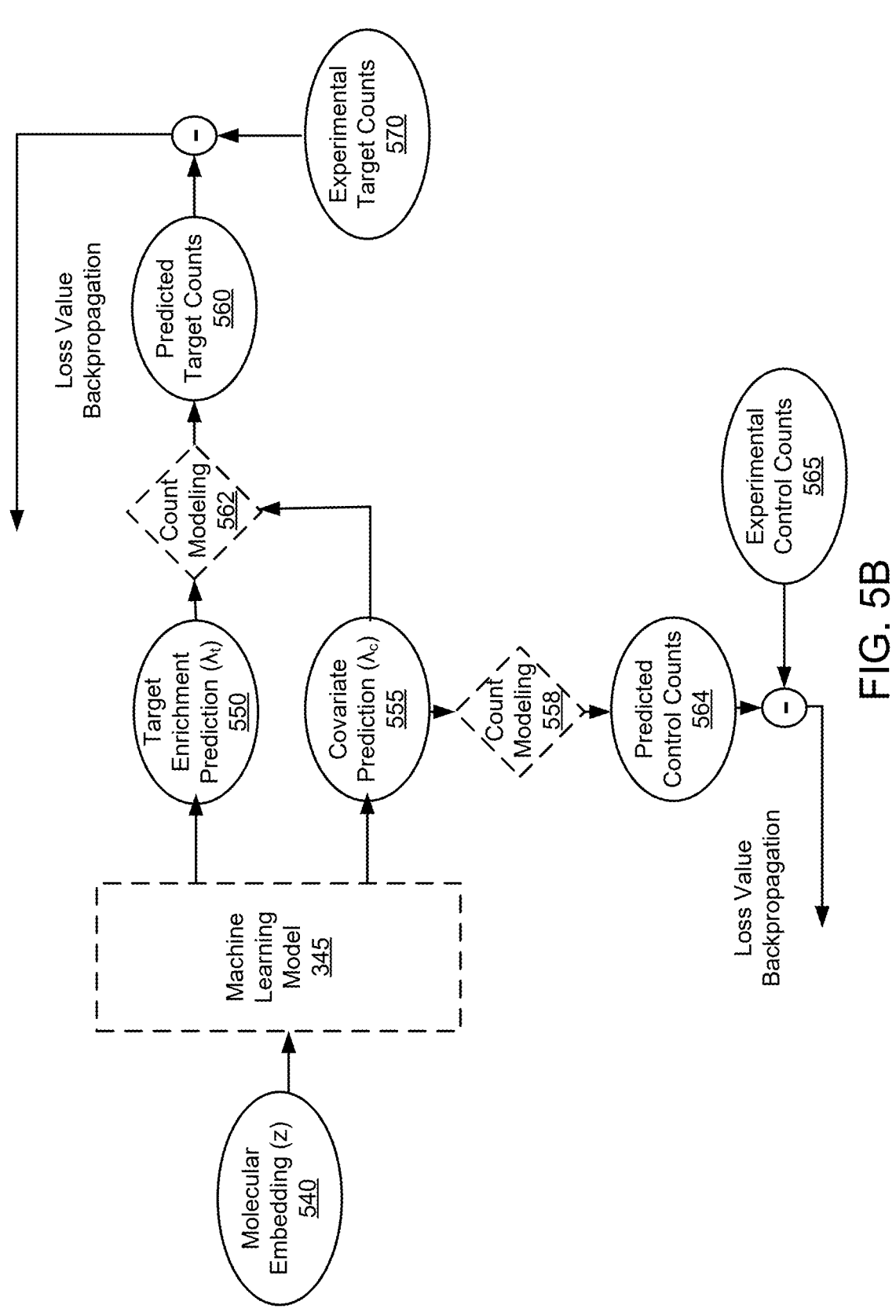
FIG. 5B further depicts an example flow diagram for training the machine learning model, in accordance with an embodiment.

Reference is now made to FIG. 5A, which depicts an example flow diagram for training the machine learning model, in accordance with an embodiment. Reference is additionally made to FIG. 5B, which further depicts an example flow diagram for training the machine learning model, in accordance with an embodiment. FIGS. 5A and 5B together depict a single training iteration for training synthons of a training compound. Thus, the flow diagram shown in FIGS. 5A and 5B can be performed multiple times over multiple iterations to train the machine learning model.

The example flow diagram in FIG. 5A begins with a plurality of training synthons 510A, 510B, 510C of a training compound. The plurality of training synthons 510 may undergo a hierarchical transformation process to generate a plurality of synthon representations (e.g., shown as monosynthon representations 530A, disynthon representations 530B and trisynthon representations 530C in FIG. 5A). Specifically, the plurality of training synthons 510 undergo a transform 325A to generate monosynthon representations 530A. The monosynthon representations 530A undergo a transform 325B to generate disynthon representations 530B. The disynthon representations 530B undergo a transform 325C to generate trisynthon representations 530C. In various embodiments, although not shown in FIG. 5A, additional transforms can occur to further generate higher order synthon representations.

Each of transform 325A, transform 325B, and transform 325C may be performed by a representation model. In various embodiments, each representation model is a machine learning model, such as a neural network. In particular embodiments, each representation model is a multilayer perceptron.

The plurality of synthon representations (e.g., shown as monosynthon representations 530A, disynthon representations 530B and trisynthon representations 530C in FIG. 5A) are combined to generate the molecular embedding (z) 540. In various embodiments, combining the plurality of synthon representations involves implementing a multi-head attention mechanism across the plurality of synthon representations.

Referring next to FIG. 5B, the molecular embedding (z) 540 is input into the machine learning model 345. The machine learning model generates a target enrichment prediction ($\lambda_t$) 550 representing binding between the training compound and a target (e.g., protein target). The machine learning model further generates an covariate prediction ($\lambda_c$) 555 (e.g., a noise prediction). Here, the target enrichment prediction 550 represents a learned enrichment value representing binding between the training compound and the target, absent sources of noise (e.g., background, matrix, covariates). The covariate prediction 555 represents a learned value or score attributable to sources of non-target binding and/or other noise sources (e.g., background, matrix, covariates).

The target enrichment prediction 550 and the covariate prediction 555 are combined to generate the predicted target counts 560. The predicted target counts 560 represents a prediction of DEL counts of a DEL panning experiment in which various sources of non-target binding and/or other sources of noise (e.g., background, matrix, covariates) are included. In various embodiments, combining the target enrichment prediction 550 and the covariate prediction 555 involves summing the target enrichment prediction 540 and the covariate prediction 555. In various embodiments, combining the target enrichment prediction 540 and the covariate prediction 555 involves performing a linear or non-linear combination of the target enrichment prediction 540 and the covariate prediction 555. For example, in some embodiments, combining the target enrichment prediction 540 and the covariate prediction 555 may involve performing a weighted summation of the target enrichment prediction 540 and the covariate prediction 555, where the weights are previously learned (e.g., learned weights from a machine learning model, such as a neural work) or can be fixed weights determined according to a predetermined weighting scheme. In various embodiments, such as an embodiment shown in FIG. 5B, a count modeling 562 is performed to combine the target enrichment prediction 550 and the covariate prediction 555 to generate the predicted target counts 560. Here, the count modeling 562 involves implementing a probability density function to model the predicted target counts 560. As described herein, the probability density function may be a Poisson distribution, optionally a zero-inflated Poisson distribution. The probability density function includes one or more learnable parameters (e.g., parameter γ).

Given the predicted target counts 560, a loss value is calculated. Here, the loss value can be calculated based on a combination of the predicted target counts 560 and the experimental target counts 570. As shown in FIG. 5B, the loss value can be represented as the difference between the predicted target counts 560 and the experimental target counts 570. Here, the loss value can be backpropagated for training at least the machine learning model.

In particular embodiments, the experimental target counts 570 is an observed dataset, such as a set of DEL counts. The predicted target counts 560 may be represented as a distribution that maximizes the likelihood of this observed data. Here, the distribution is parametrized by weights predicted by the model. To compute the loss value for a single training example (e.g., single training molecule), the likelihood of each count observation under the predicted distribution is determined. Assuming that each observed data (e.g., count observation) is independent, the loss value for a single training molecule can be the product of individual probabilities or likelihoods (associated with each count observation for that molecule). In particular embodiments, the loss value is calculated by taking the negative log likelihood (NLL) as the loss.

As further shown in FIG. 5B, the covariate prediction ($\lambda_c$) can be analyzed e.g., by performing a count modeling 558 to generate predicted control counts 564. In various embodiments, the count modeling 558 involves implementing a probability density function to model the predicted control counts 564. As described herein, the probability density function may be a Poisson distribution, optionally a zero-inflated Poisson distribution. The probability density function includes one or more learnable parameters (e.g., parameter γ).

Given the predicted control counts 564, a loss value is calculated. Here, the loss value can be calculated based on a combination of the predicted control counts 564 and the experimental control counts 565. As shown in FIG. 5B, the loss value can be represented as the difference between the predicted control counts 564 and the experimental control counts 565. Here, the loss value can be backpropagated for training at least the machine learning model.

Although FIG. 5B shows two separate loss values that are backpropagated, in various embodiments, the two loss values can be combined into a single loss value that is backpropagated for training at least the machine learning model. In various embodiments, the machine learning model outputs two or more covariate predictions 555 which model two or more covariates. Therefore, count modeling 558 can be performed for the two or more covariate predictions 555 to generate two or more predicted control counts 564. The two or more predicted control counts 564 are combined with corresponding two or more experimental control counts 565 for each of the two or more covariates to generate a loss value for backpropagation.

The loss value is backpropagated to train at least the machine learning model 345. The parameters of the machine learning model 345 are adjusted according to the calculated loss value. Specifically, the parameters of the machine learning model 345 are adjusted to minimize the calculated loss value. In various embodiments, the backpropagated loss value is further used to train one or more additional machine learning models including the representation models that perform the transform 325A, 325B, or 325C shown in FIG. 5A, or the probability density functions for performing the count modeling 558 or 562 shown in FIG. 5B. Specifically, the trainable elements shown in FIGS. 5A and 5B are depicted in dashed lines. In various embodiments, each of the machine learning model 345, the representation models that perform the transform 325A, 325B, or 325C shown in FIG. 5A, and the probability density functions for performing the count modeling 558 or 562 shown in FIG. 5B are jointly trained. Put another way, the parameters of the machine learning model 345, the parameters of the representation models, and the parameters of the probability density functions can be jointly adjusted over training iterations such that the machine learning model is able to better predict experimentally observed target counts and experimentally observed control counts arising from background/matrix/covariates, thereby intrinsically learning the target enrichment prediction.

Figure 6:
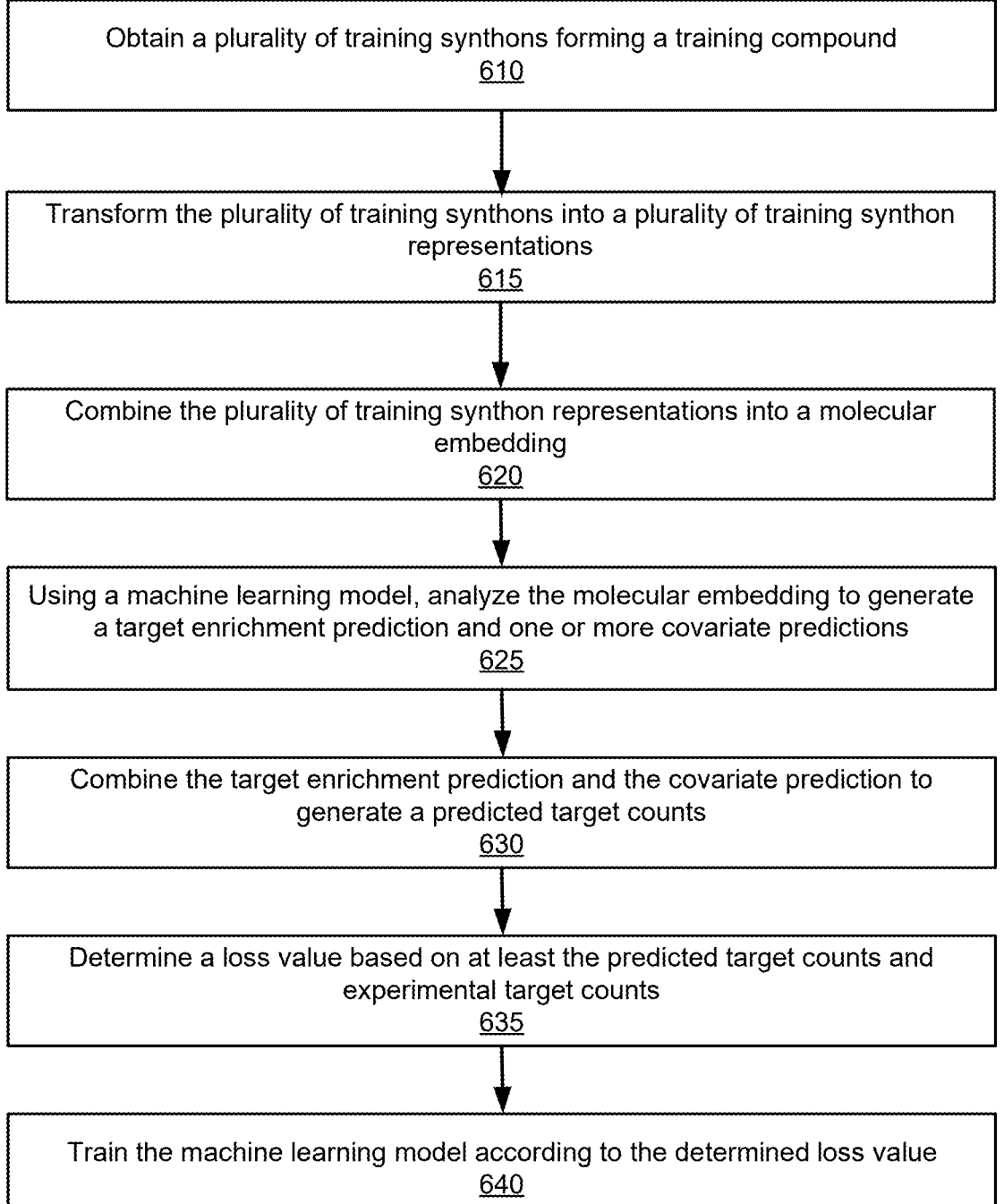
FIG. 6 depicts an example flow process for training a machine learning model, in accordance with an embodiment.

Reference is now made to FIG. 6 depicts an example flow process for training a machine learning model, in accordance with an embodiment.

Step 610 involves obtaining a plurality of training synthons forming a training compound. Here, the plurality of training synthons represent factorized synthons of the training compound.

Step 615 involves transforming the plurality of training synthons into a plurality of training synthon representations. In various embodiments, the step of transforming the plurality of training synthons may involve a hierarchical transformation process, such as the process described in reference to FIG. 3A, to generate the plurality of training synthon representations. Briefly, transforming the plurality of training synthons into a plurality of training synthon representations may involve applying one or more representation models to hierarchically construct synthon representations of higher order.

Step 620 involves combining the plurality of training synthon representations (e.g., monosynthon representations, disynthon representations, trisynthon representations, etc.) into a molecular embedding.

Step 625 involves analyzing the molecular embedding using a machine learning model to generate a target enrichment prediction and one or more covariate predictions. In particular embodiments, the machine learning model generates two covariate predictions (e.g., load bias and replicate bias).

Step 630 involves combining the target enrichment prediction and the covariate prediction to generate a predicted target counts. In various embodiments, combining the target enrichment prediction and the covariate prediction involves performing a count modeling by implementing a probability density function that models the predicted target counts (e.g., DEL counts).

Step 635 involves determining a loss value based on at least the predicted target counts and experimental target counts. Here, the experimental target counts serves as a ground truth value.

Step 640 involves training the machine learning model according to the determined loss value. In various embodiments, step 640 further involves training one or more representation models and one or more models that use the probability density functions for modeling the predicted target counts. In various embodiments, the determined loss value is used to jointly train each of the machine learning model, the one or more representation models, and the models that use the probability density functions for modeling the predicted target counts. Thus, over training iterations, the target enrichment prediction is learned by trying to predict at least the experimental control counts (e.g., observed experimental control counts from a DEL experiment modeling a particular covariate).

Benchmarking Machine Learning Models

In various embodiments, the methods described herein, are evaluated relative to known methods to determine the relative performance of the disclosed models. Example known methods includes but is not limited to: Random forest (RF), XGBoost, k-nearest neighbors (kNN), and deep neural network (DNN), and/or Graph isomorphism network (GIN). Evaluation metrics for model performance can include any known machine learning performance metric (e.g. loss-value, spearman correlation between model prediction and experimental results, F1 score, accuracy, precision, and/or recall).

Systems and Computing Devices

In various embodiments, the methods described herein, are performed on a computing device. Examples of a computing device can include a personal computer, desktop computer laptop, server computer, a computing node within a cluster, message processors, hand-held devices, multiprocessor systems, microprocessor-based or programmable consumer electronics, network PCs, minicomputers, mainframe computers, mobile telephones, PDAs, tablets, pagers, routers, switches, and the like.

Figure 7A:
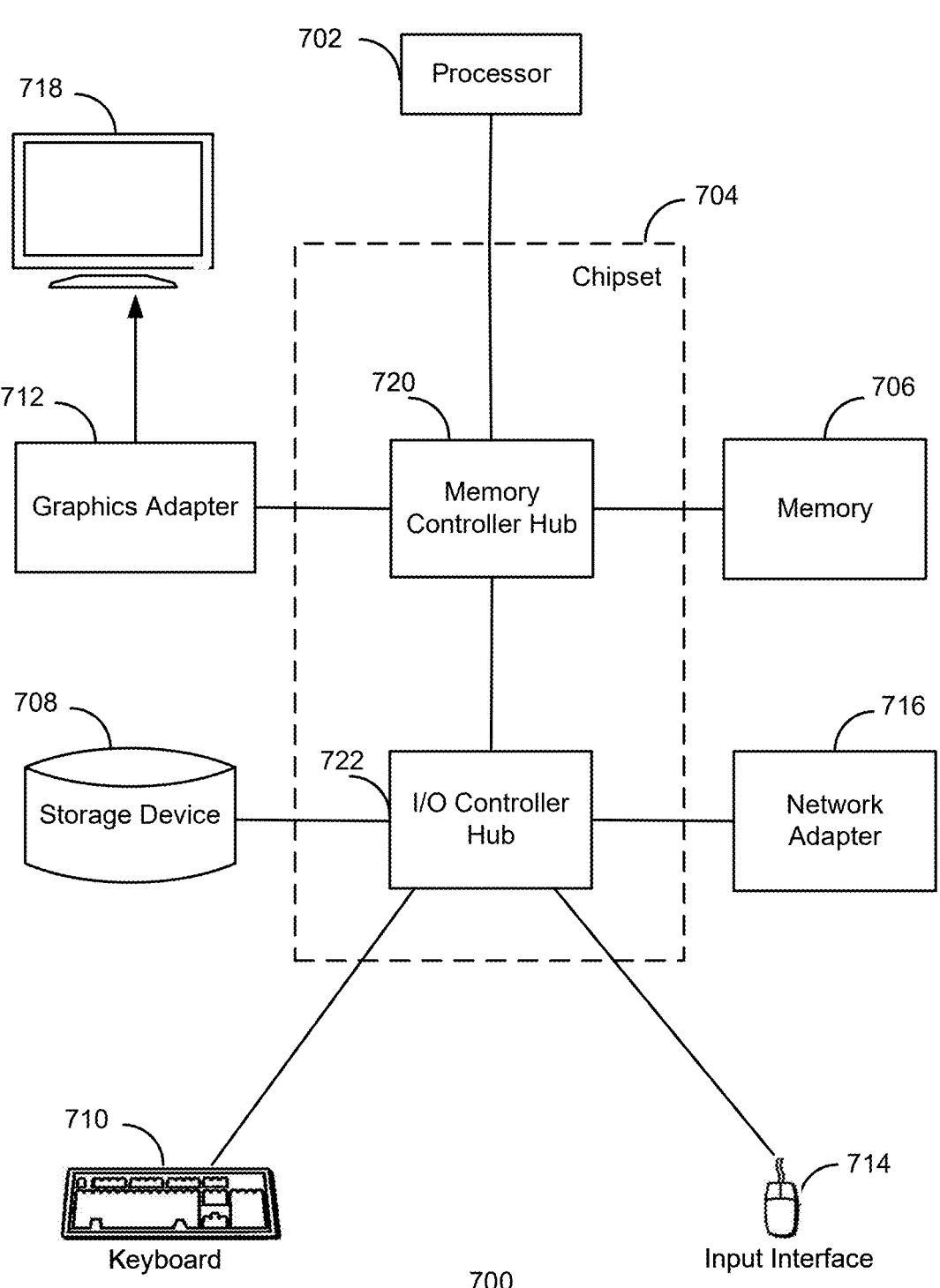
FIG. 7A illustrates an example computing device for implementing the system and methods described in FIGS. 1A-1B, 2, 3A-3B, 4A-4C, 5A-5B, and 6.
Figure 7B:
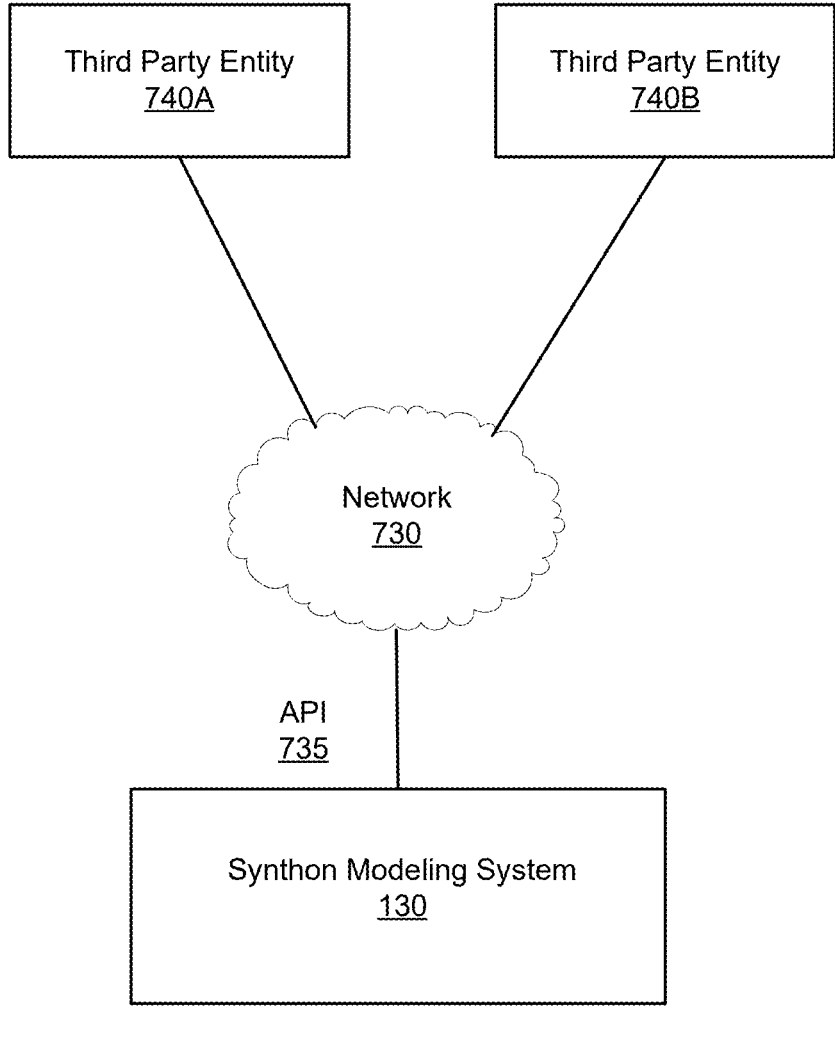
FIG. 7B depicts an overall system environment for implementing a synthon modeling system, in accordance with an embodiment.
Figure 7C:
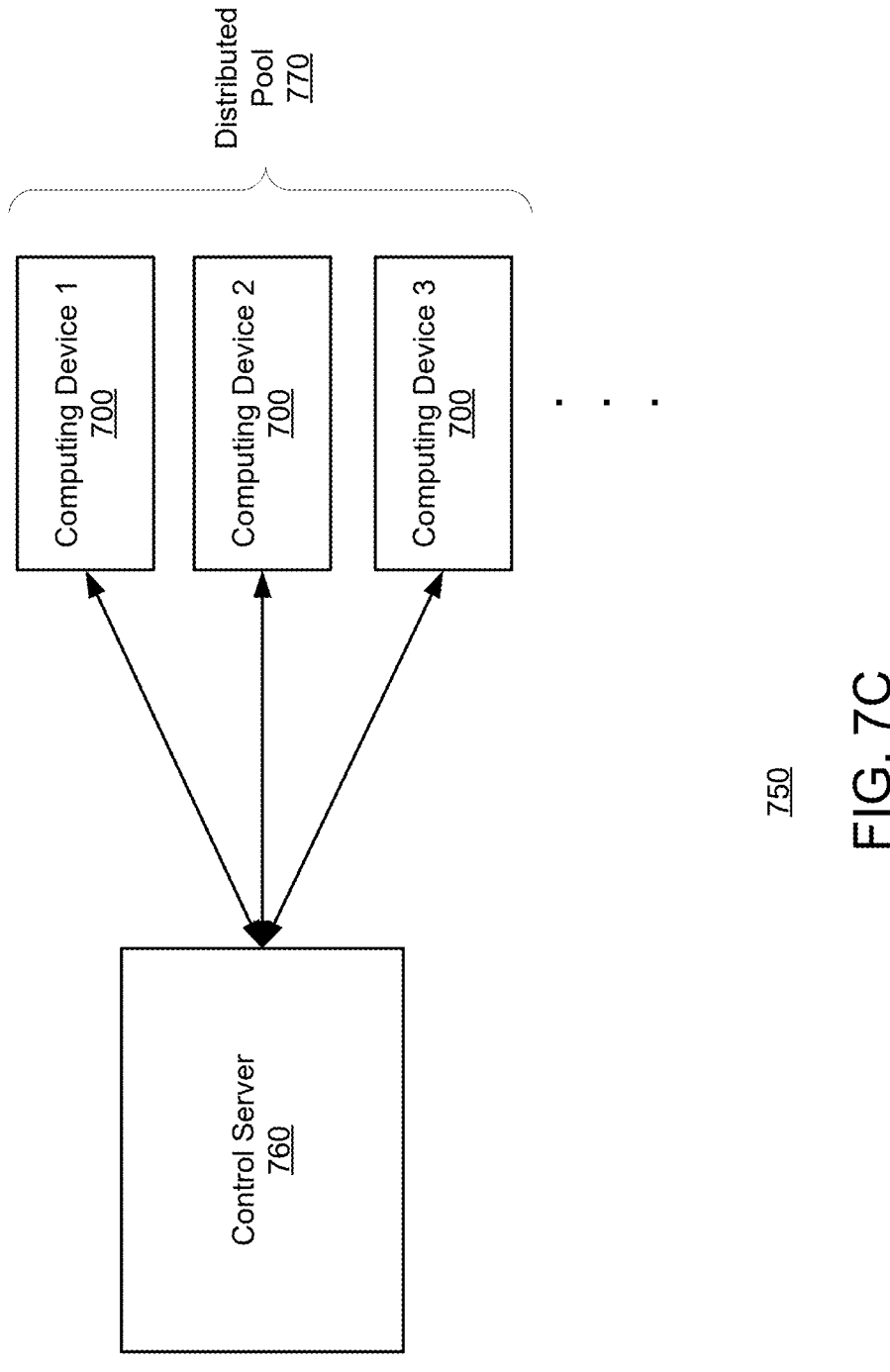
FIG. 7C is an example depiction of a distributed computing system environment for implementing the system environment of FIG. 7B.

FIG. 7A illustrates an example computing device for implementing the system and methods described in FIGS. 1A-1B, 2, 3A-3B, 4A-4C, 5A-5B, and 6. Furthermore, FIG. 7B depicts an overall system environment for implementing a synthon modeling system, in accordance with an embodiment. FIG. 7C is an example depiction of a distributed computing system environment for implementing the system environment of FIG. 7B.

In some embodiments, the computing device 700 shown in FIG. 7A includes at least one processor 702 coupled to a chipset 704. The chipset 704 includes a memory controller hub 720 and an input/output (I/O) controller hub 722. A memory 706 and a graphics adapter 712 are coupled to the memory controller hub 720, and a display 718 is coupled to the graphics adapter 712. A storage device 708, an input interface 714, and network adapter 716 are coupled to the I/O controller hub 722. Other embodiments of the computing device 700 have different architectures.

The storage device 708 is a non-transitory computer-readable storage medium such as a hard drive, compact disk read-only memory (CD-ROM), DVD, or a solid-state memory device. The memory 706 holds instructions and data used by the processor 702. The input interface 714 is a touch-screen interface, a mouse, track ball, or other type of input interface, a keyboard, or some combination thereof, and is used to input data into the computing device 700. In some embodiments, the computing device 700 may be configured to receive input (e.g., commands) from the input interface 714 via gestures from the user. The graphics adapter 712 displays images and other information on the display 718. The network adapter 716 couples the computing device 700 to one or more computer networks.

The computing device 700 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 708, loaded into the memory 706, and executed by the processor 702.

The types of computing devices 700 can vary from the embodiments described herein. For example, the computing device 700 can lack some of the components described above, such as graphics adapters 712, input interface 714, and displays 718. In some embodiments, a computing device 700 can include a processor 702 for executing instructions stored on a memory 706.

In various embodiments, the different entities depicted in FIG. 7B may implement one or more computing devices to perform the methods described above, including the methods of training and deploying one or more machine learning models. For example, the synthon modeling system 130, third party entity 740A, and third party entity 740B may each employ one or more computing devices. As another example, one or more of the subsystems of the synthon modeling system 130 (as shown in FIG. 1B) may employ one or more computing devices to perform the methods described above.

The methods of training and deploying one or more machine learning models can be implemented in hardware or software, or a combination of both. In one embodiment, a non-transitory machine-readable storage medium, such as one described above, is provided, the medium comprising a data storage material encoded with machine readable data which, when using a machine programmed with instructions for using said data, is capable of displaying any of the datasets and execution and results of a machine learning model disclosed herein.

Embodiments of the methods described above can be implemented in computer programs executing on programmable computers, comprising a processor, a data storage system (including volatile and non-volatile memory and/or storage elements), a graphics adapter, an input interface, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high-level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that is capable of recording and reproducing the signature pattern information of the present invention. The databases of the present invention can be recorded on computer readable media, e.g., any medium that can be read and accessed directly by a computer. Such media include, but are not limited to magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g., word processing text file, database format, etc.

System Environment

FIG. 7B depicts an overall system environment for implementing a synthon modeling system, in accordance with an embodiment. The overall system environment 725 includes a synthon modeling system 130, as described earlier in reference to FIG. 1A, and one or more third party entities 740A and 740B in communication with one another through a network 730. FIG. 7A depicts one embodiment of the overall system environment 725. In other embodiments, additional or fewer third party entities 740 in communication with the synthon modeling system 130 can be included. Generally, the synthon modeling system 130 implements machine learning models that make predictions, e.g., predictions for compound binding, virtual screen, or hit selection and analysis. The third party entities 740 communicate with the synthon modeling system 130 for purposes associated with implementing the machine learning models or obtaining predictions or results from the machine learning models.

In various embodiments, the methods described above as being performed by the synthon modeling system 130 can be dispersed between the synthon modeling system 130 and third party entities 740. For example, a third party entity 740A or 740B can generate training data and/or train a machine learning model. The synthon modeling system 130 can then deploy the machine learning model to generate predictions e.g., predictions for compound binding, virtual screen, or hit selection and analysis.

Third Party Entity

In various embodiments, the third party entity 740 represents a partner entity of the synthon modeling system 130 that operates either upstream or downstream of the synthon modeling system 130. As one example, the third party entity 740 operates upstream of the synthon modeling system 130 and provide information to the synthon modeling system 130 to enable the training of machine learning models. In this scenario, the synthon modeling system 130 receives data, such as DEL experimental data collected by the third party entity 740. For example, the third party entity 740 may have performed the analysis concerning one or more DEL experiments (e.g., DEL experiment 115A or 115B shown in FIG. 1A) and provides the DEL experimental data of those experiments to the synthon modeling system 130. Here, the third party entity 740 may synthesize the small molecule compounds of the DEL, incubate the small molecule compounds of the DEL with immobilized protein targets, eluting bound compounds, and amplifying/sequencing the DNA tags to identify putative binders. Thus, the third party entity 740 may provide the sequencing data to the synthon modeling system 130.

As another example, the third party entity 740 operates downstream of the synthon modeling system 130. In this scenario, the synthon modeling system 130 may identify predicted binders through a virtual screen and provides information relating to the predicted binders to the third party entity 740. The third party entity 740 can subsequently use the information identifying the predicted binders relating for their own purposes. For example, the third party entity 740 may be a drug developer. Therefore, the drug developer can synthesize the predicted binder for further investigation.

Network

This disclosure contemplates any suitable network 730 that enables connection between the synthon modeling system 130 and third party entities 740. The network 730 may comprise any combination of local area and/or wide area networks, using both wired and/or wireless communication systems. In one embodiment, the network 730 uses standard communications technologies and/or protocols. For example, the network 730 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 730 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 730 may be represented using any suitable format, such as hypertext markup language (HTML) or extensible markup language (XML). In some embodiments, all or some of the communication links of the network 730 may be encrypted using any suitable technique or techniques.

Application Programming Interface (API)

In various embodiments, the synthon modeling system 130 communicates with third party entities 740A or 740B through one or more application programming interfaces (API) 735. The API 735 may define the data fields, calling protocols and functionality exchanges between computing systems maintained by third party entities 740 and the synthon modeling system 130. The API 735 may be implemented to define or control the parameters for data to be received or provided by a third party entity 740 and data to be received or provided by the synthon modeling system 130. For instance, the API may be implemented to provide access only to information generated by one of the subsystems comprising the synthon modeling system 130. The API 735 may support implementation of licensing restrictions and tracking mechanisms for information provided by synthon modeling system 130 to a third party entity 740. Such licensing restrictions and tracking mechanisms supported by API 735 may be implemented using blockchain-based networks, secure ledgers and information management keys. Examples of APIs include remote APIs, web APIs, operating system APIs, or software application APIs.

An API may be provided in the form of a library that includes specifications for routines, data structures, object classes, and variables. In other cases, an API may be provided as a specification of remote calls exposed to the API consumers. An API specification may take many forms, including an international standard such as POSIX, vendor documentation such as the Microsoft Windows API, or the libraries of a programming language, e.g., Standard Template Library in C++ or Java API. In various embodiments, the synthon modeling system 130 includes a set of custom API that is developed specifically for the synthon modeling system 130 or the subsystems of the synthon modeling system 130.

Distributed Computing Environment

In some embodiments, the methods described above, including the methods of training and implementing one or more machine learning models, are performed in distributed computing system environments where local and remote computer systems, which are linked (either by hardwired data links, wireless data links, or by a combination of hardwired and wireless data links) through a network, both perform tasks. In some embodiments, one or more processors for implementing the methods described above may be located in a single geographic location (e.g., within a home environment, an office environment, or a server farm). In various embodiments, one or more processors for implementing the methods described above may be distributed across a number of geographic locations. In a distributed computing system environment, program modules may be located in both local and remote memory storage devices.

FIG. 7C is an example depiction of a distributed computing system environment for implementing the system environment of FIG. 7B. The distributed computing system environment 750 can include a control server 760 connected via communications network with at least one distributed pool 770 of computing resources, such as computing devices 700, examples of which are described above in reference to FIG. 7. In various embodiments, additional distributed pools 770 may exist in conjunction with the control server 760 within the distributed computing system environment 750. Computing resources can be dedicated for the exclusive use in the distributed pool 770 or shared with other pools within the distributed processing system and with other applications outside of the distributed processing system. Furthermore, the computing resources in distributed pool 770 can be allocated dynamically, with computing devices 700 added or removed from the pool 710 as necessary.

In various embodiments, the control server 760 is a software application that provides the control and monitoring of the computing devices 700 in the distributed pool 770. The control server 760 itself may be implemented on a computing device (e.g., computing device 700 described above in reference to FIG. 7A). Communications between the control server 760 and computing devices 700 in the distributed pool 770 can be facilitated through an application programming interface (API), such as a Web services API. In some embodiments, the control server 760 provides users with administration and computing resource management functions for controlling the distributed pool 770 (e.g., defining resource availability, submission, monitoring and control of tasks to performed by the computing devices 700, control timing of tasks to be completed, ranking task priorities, or storage/transmission of data resulting from completed tasks).

In various embodiments, the control server 760 identifies a computing task to be executed across the distributed computing system environment 750. The computing task can be divided into multiple work units that can be executed by the different computing devices 700 in the distributed pool 770. By dividing up and executing the computing task across the computing devices 700, the computing task can be effectively executed in parallel. This enables the completion of the task with increased performance (e.g., faster, less consumption of resources) in comparison to a non-distributed computing system environment.

In various embodiments, the computing devices 700 in the distributed pool 770 can be differently configured in order to ensure effective performance for their respective jobs. For example, a first set of computing devices 700 may be dedicated to performing collection and/or analysis of phenotypic assay data. A second set of computing devices 700 may be dedicated to performing the training of machine learning models. The first set of computing devices 700 may have less random access memory (RAM) and/or processors than the second set of second computing devices 700 given the likely need for more resources when training the machine learning models.

The computing devices 700 in the distributed pool 770 can perform, in parallel, each of their jobs and when completed, can store the results in a persistent storage and/or transmit the results back to the control server 760. The control server 760 can compile the results or, if needed, redistribute the results to the respective computing devices 700 to for continued processing.

In some embodiments, the distributed computing system environment 750 is implemented in a cloud computing environment. In this description, "cloud computing" is defined as a model for enabling on-demand network access to a shared set of configurable computing resources. For example, the control server 760 and the computing devices 700 of the distributed pool 770 may communicate through the cloud. Thus, in some embodiments, the control server 760 and computing devices 700 are located in geographically different locations. Cloud computing can be employed to offer on-demand access to the shared set of configurable computing resources. The shared set of configurable computing resources can be rapidly provisioned via virtualization and released with low management effort or service provider interaction, and then scaled accordingly. A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

EXAMPLES

Example 1: Example Model Architecture

The Examples describe the disclosed model, herein referred to as the "Factorized" model, which learns factorized synthon representations, constructs corresponding di-synthon and tri-synthon representations from the factorized synthon representations, and generates target enrichment predictions.

Molecules as Synthon Compositions

The factorized model disclosed herein broadly capitalizes on the combinatorial nature of DEL molecules, and creates a composition of representations using the individual building blocks of each molecule. As DEL selection data signal is highly correlated to its synthon composition, this hierarchical decomposition captures the noisy nuances of the data. To that end, described here is a fully generative model that captures the underlying data-generating process for DEL count data. First, introduced herein are mathematical notations:

Let $\chi$ be the set of DEL molecules in the dataset, and $\{S_A, S_B, S_C\}$ be the sets of synthons at the first, second and third positions respectively. Each molecule is denoted by $x_{abc} \in \chi$, where the subscript indicates the identity of the synthon at a particular position ($a \in S_A$, $b \in S_B$, $c \in S_C$). To simplify notation, the subscript for a particular synthon position is omitted if it is absent. For instance, $x_b$ denotes the molecule corresponding to the synthon b at the second position, and $x_{ab}$ denotes the molecule corresponding to the combination of synthon a at the first position and b at the second position. This process was further generalized trivially to higher order synthon composition over more than 3 synthons, but for the purpose of presentation, the setting of tri-synthons DEL molecules was the focus here. DEL molecules were used in selection experiments wherein molecules underwent multiple rounds of washes to determine the strongest binders in each experimental condition. Here, there were two experimental conditions, the target condition, which describes the data for selection against the protein target of interest, and the matrix condition, which describes the data in the absence of the protein target. The observed data were DNA read counts, which is denoted as $$C_t = \{c_t^i | i \in [1, n_t]\}$$

and $$C_m = \{c_m^j | j \in [1, n_m]\}$$

for target and matrix read counts respectively. Here, $(n_t, n_m)$ are the number of count replicates for target and control respectively. Moreover, DEL data is usually calibrated with an additional read-out of the library itself, which we denote as $c_p$ (this notation is lowercase, as there is usually only a single read-out of the library). This library read-out is a noisy estimate of the relative abundance of each molecule member.

Generative Model of DEL Data

Figure 8A:
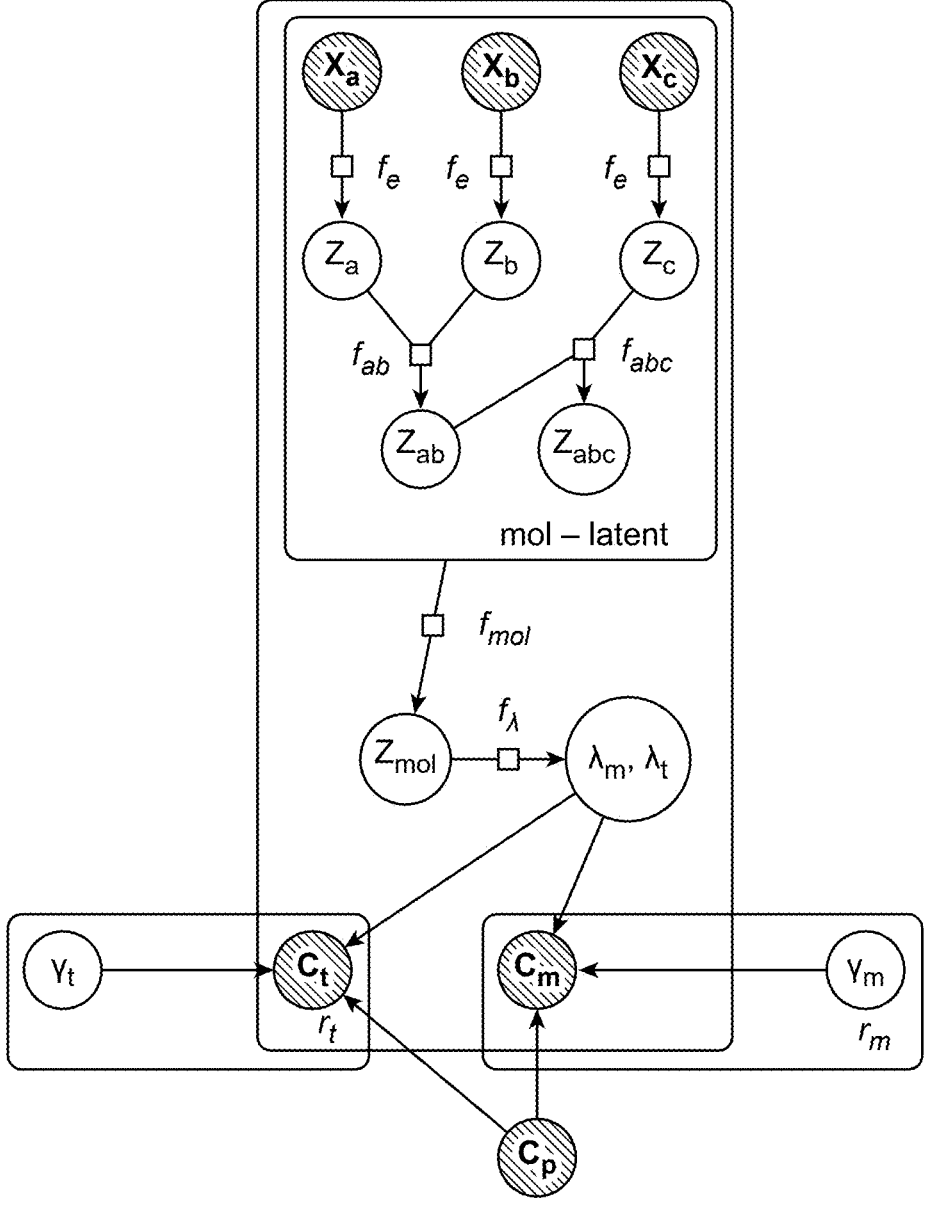
FIG. 8A depicts the general paradigm for modeling DEL molecules leveraging their combinatorial nature.

The general objective is to maximize the likelihood of observing the count data given input molecule $x_{abc}$. The plate model of this paradigm is depicted in FIG. 8A. For brevity, assume that there is only one replicate of counts, but can easily extend to multiple observations. Let $Z = \{z_s | s \in [a, b, c, ab, bc, ac, abc]\}$ be the latent synthon embeddings; in its most basic form, the objective was decomposed into Equation 1:

$$p(C_m, C_t | x_a, x_b, x_c) = p(C_m, C_t | Z) \cdot p(Z | x_a, x_b, x_c) \qquad (1)$$

To better de-noise the contribution of actual molecule binding to the read-outs, latent variables were explicitly defined as $\{\lambda_t, \lambda_m\}$, which captures a molecule's affinity for binding in the target and matrix experimental conditions. While there are many factors that affect the final read count for DEL experiments, two prominent factors were chosen for incorporation into the mode. The two factors included pre-selection library read-out, $c_p$, and replicate-level noise, which are denoted $\{\gamma_t, \gamma_m\}$. The latter accounts for variance across different replicates of the same experiment, as the differently encoded DNA for replicates can be correlated to PCR bias noise. The generative model can then be broken down according to Equation 2, where $\Theta$ is the set of learned model parameters.

$$p(C_m, C_t | x_a, x_b, x_c; \Theta) = p(C_m, C_t | \lambda_m, \lambda_t, c_p, \gamma_m, \gamma_t) \cdot \qquad (2)$$
$$p(\lambda_m, \lambda_t | Z; \Theta) \cdot p(c_p) \cdot p(\gamma_m, \gamma_t) \cdot p(Z | x_a, x_b, x_c; \Theta)$$

Parametrizing Synthon and Molecule Representations Via Neural Networks

Figure 8B:
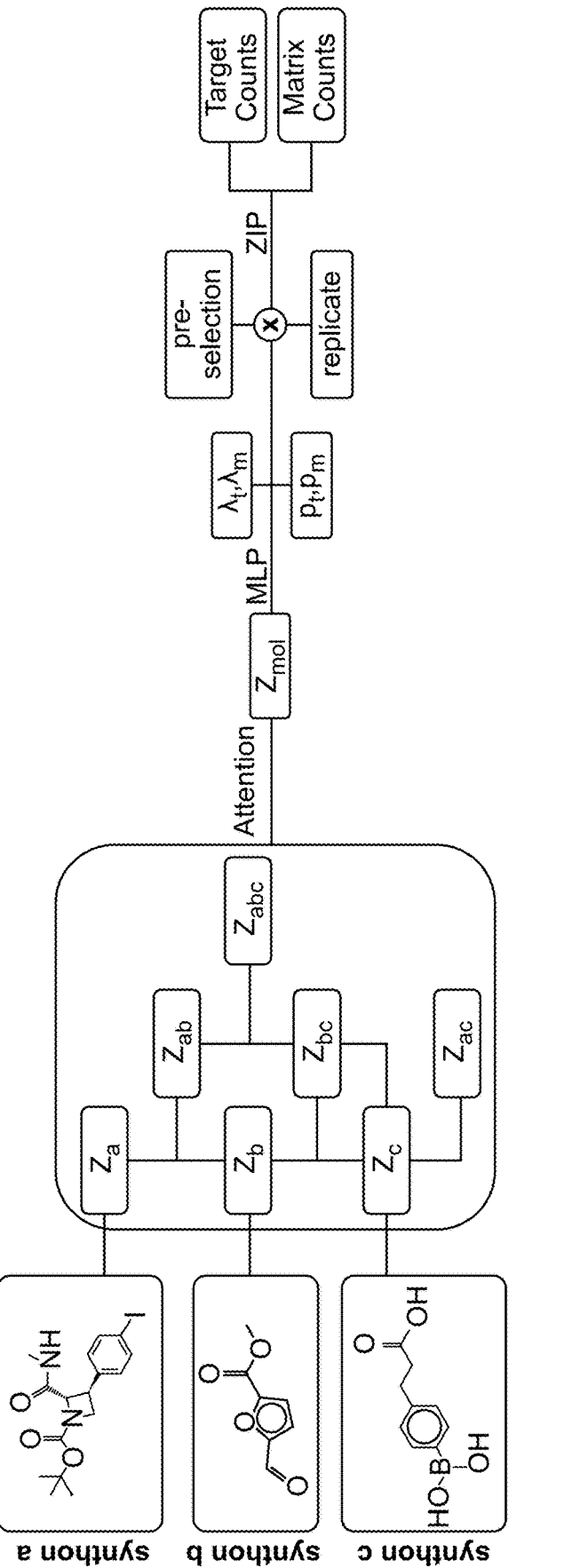
FIG. 8B depicts a schematic illustration of the machine learning architecture and data flow.

Reference is made to FIG. 8B, which depicts a schematic illustration of the architecture of the Factorized model and corresponding data flow. Let $x_{abc} \in X_{ABC}$ be the set of DEL molecules, where $a \in A$, $b \in B$, $c \in C$ are the sets of synthons at the first, second and third position respectively.

Additionally included is the null element $\emptyset$ in each set to indicate an absence of synthon at that position (since not all molecules may be tri-synthons). To simplify notation, the subscript for a particular synthon is omitted if it is absent. For instance, $x_b$ denotes the molecule corresponding to the synthon b at the second position, and $x_{ab}$ denotes the molecule corresponding to the combination of synthon a at the first position and b at the second position.

Let z be the output embedding of the molecule. There is some transformation f: $X_{ABC} \rightarrow \mathbb{R}^n$ that takes an input molecule and maps it to an n-dimensional embedding. The simplest transformation f can be a multi-layer perceptron (MLP) on top of fingerprint representation of $x_{abc}$, i.e., $z_{abc} = f(x_{abc}) = MLP(fps_{x_{abc}})$.

However, full molecules $x_{abc}$ require careful enumeration, which is typically a costly process. Since DEL data is highly correlated within a particular synthon group, individual synthon information is preserved in the construction of molecule embeddings. To that end, proposed here is a model that does not require manual enumeration. First, individual mono-synthon embeddings were constructed as $z_\sigma = f(x_\sigma)$ $\forall \sigma \in \{a, b, c\}$. Next, di-synthon embeddings were constructed as $z_{ab} = MLP([z_a; z_b])$ and tri-synthon (full molecule embeddings) as $z_{abc} = MLP([z_{ab}, z_{bc}])$. The aggregated molecule embedding is then:

$$z = Multihead - Attention([z_a; z_b; z_c; z_{ab}; z_{bc}; z_{ac}; z_{abc}]) \qquad (1)$$

Here, the molecule embedding z is used to predict intrinsic properties of the molecule: $\{\lambda_c, \lambda_t\}$ which are the molecule's binding affinity for control/matrix and target respectively, and $\{p_c, p_t\} \in (0, 1)$, which is a probability that measures the noisiness/uncertainty of prediction.

Let $$\{c_c^i, c_t^j\}$$

$\in N$ be the count data for the i/jth replicate of control/matrix and target respectively. To incorporate load/pre-selection and replicate bias, additional terms were introduced including: let l be the normalized pre-selection count data $$\left( l = 1e6 * \frac{l_x}{L} \,\middle|\, L = \sum_x l_x \right),$$

and let $$\gamma_c^i, \gamma_t^j$$

$\in \mathbb{R}$ be learned weights to account for replicate bias in control and target experiments.

The count data was modeled as a zero-inflated Poisson distribution as follows:

$$c_c^i \sim ZIPoisson(l * \exp(\gamma_c^i) * \exp(\lambda_c)) \qquad (2)$$

$$c_t^j \sim ZIPoisson(l * \exp(\gamma_t^j) * \exp(\lambda_c + \lambda_t)) \qquad (3)$$

Example 2: Example Data and Training

Experiments in this Example were conducted on public DEL data from Gerry, C., et al "DNA barcoding a complete matrix of stereoisomeric small molecules."*Journal of the American Chemical Society* 2019, 141, 10225-10235, which is hereby incorporated by reference in its entirety. Gerry et al. describes panning data on two targets: Carbonic Anhydrase IX (CA-IX) and horseradish peroxidase (HRP). Their DEL is a tri-synthon library, consisting of 8 synthons at the A position, 114 synthons at the B position and 118 synthons at the C position (107,616 total molecules) chosen to encourage chemical diversity of the molecules. Their data consists of both on-target experiments with read counts as well as off-target read counts that are collected with only the beads. For CAIX this dataset includes 2 replicates of off-target control data, and 4 replicates of on-target experimental data; while for HRP, this dataset includes 4 replicates of off-target control data and 2 replicates of on-target data. Additionally, there is data collected on the pre-selection DEL, which is an indicator of the relative abundance of the different DEL members.

Figure 9A:
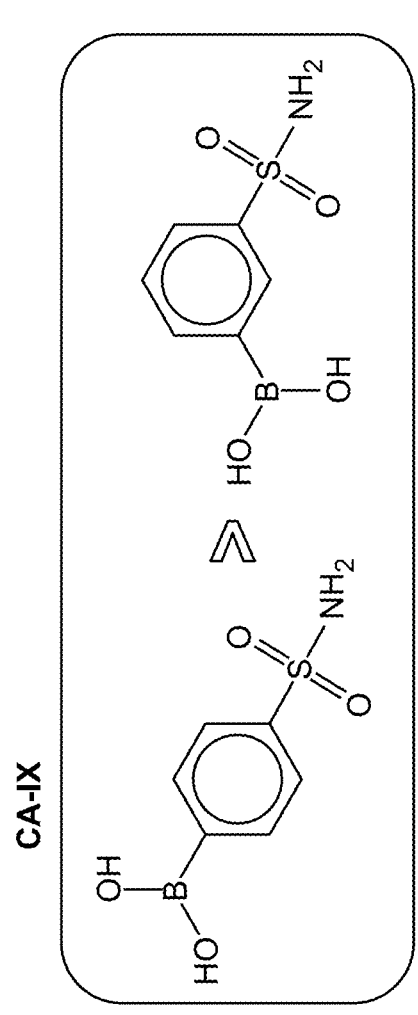
FIG. 9A shows known pharmacophores for carbonic anhydrase IX (CA-IX) pictured in order of binding affinity.
Figure 9B:
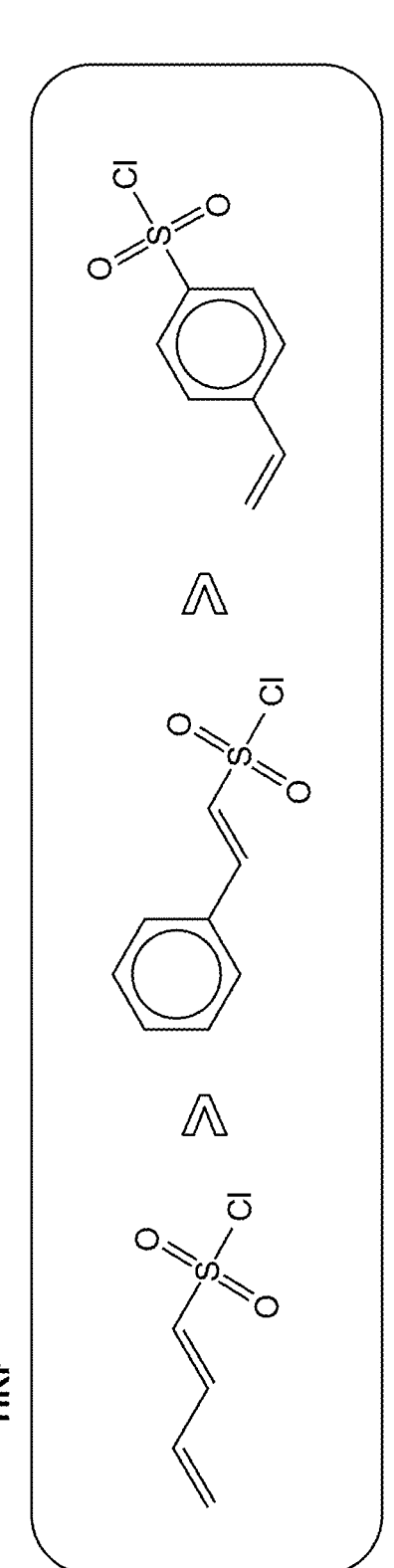
FIG. 9B shows known pharmacophores of horseradish peroxidase (HRP) pictured in order of binding affinity.
Figure 10A:
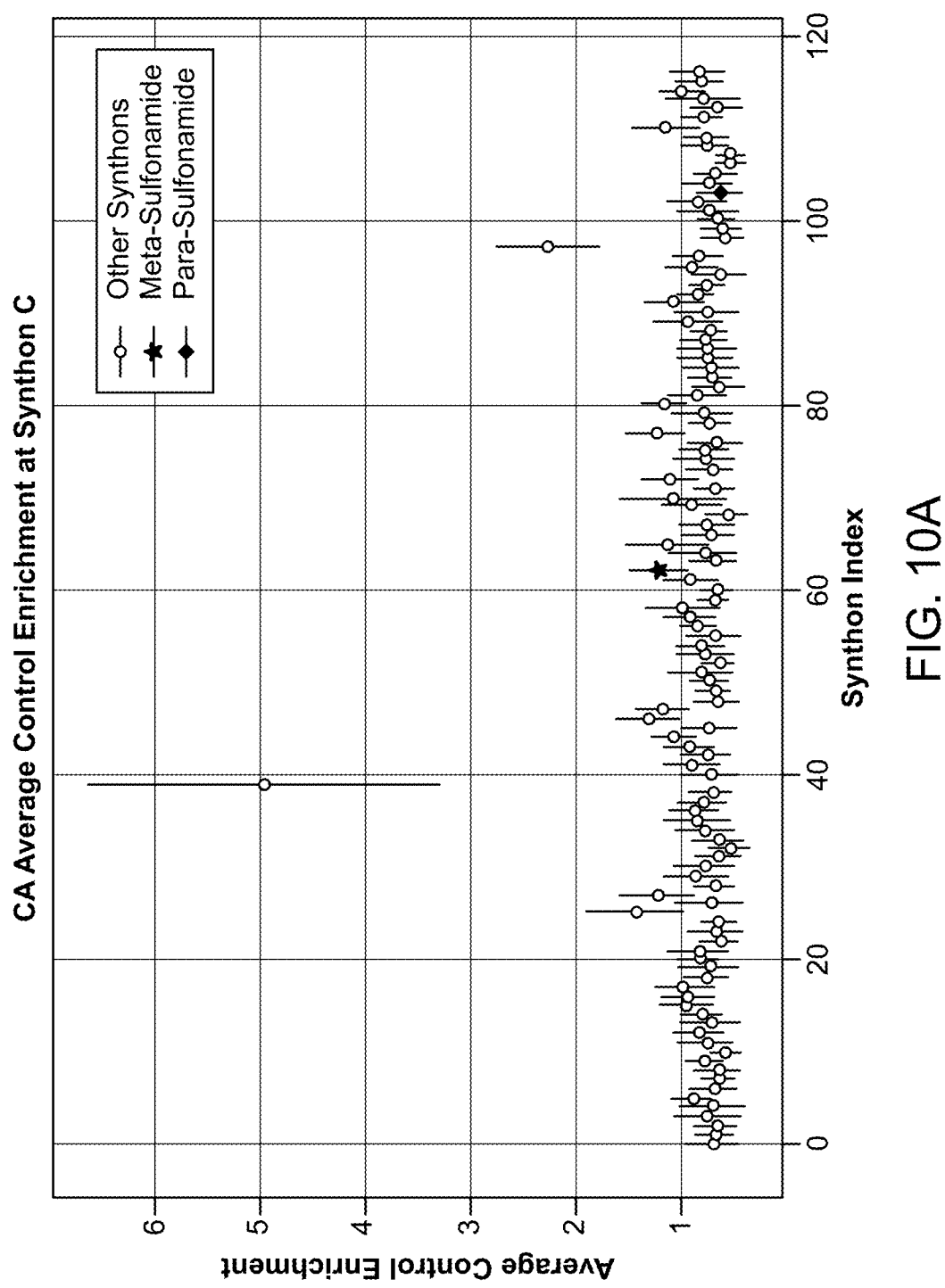
FIGS. 10A-10D show predicted average enrichment of molecules in control and target conditions grouped by synthons at positions B or C for CA-IX and HRP.
Figure 10B:
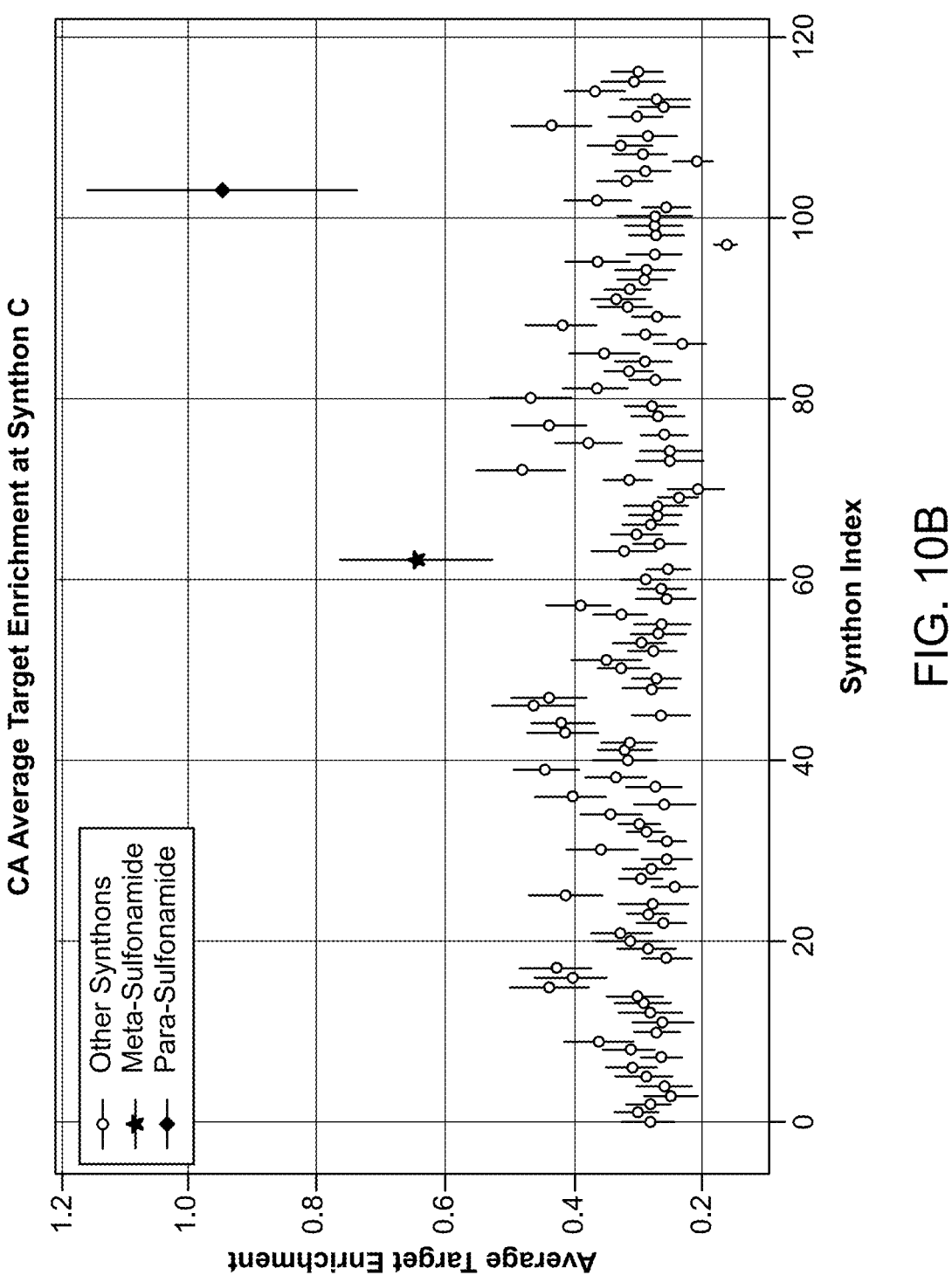
Figure 10C:
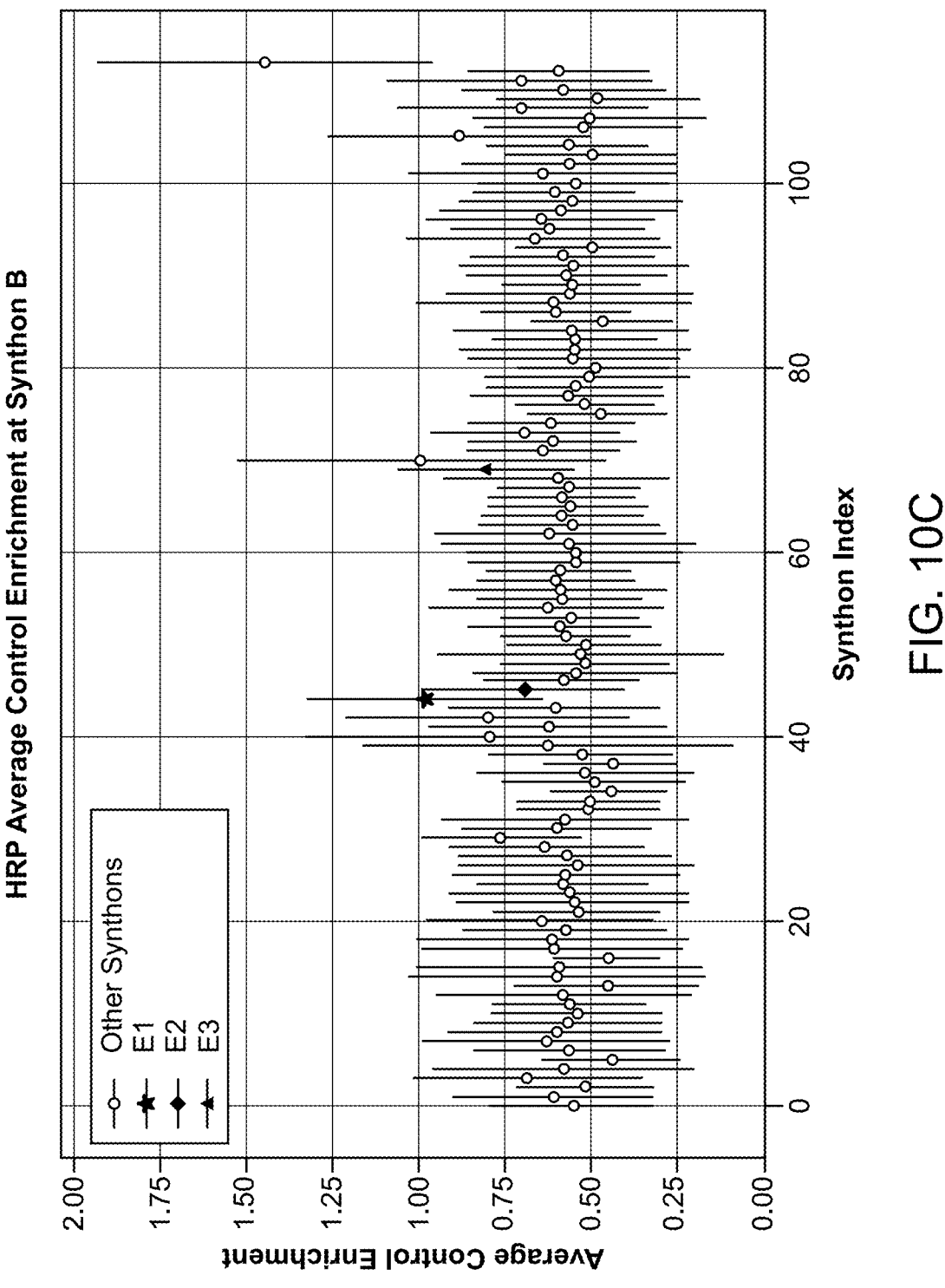
Figure 10D:
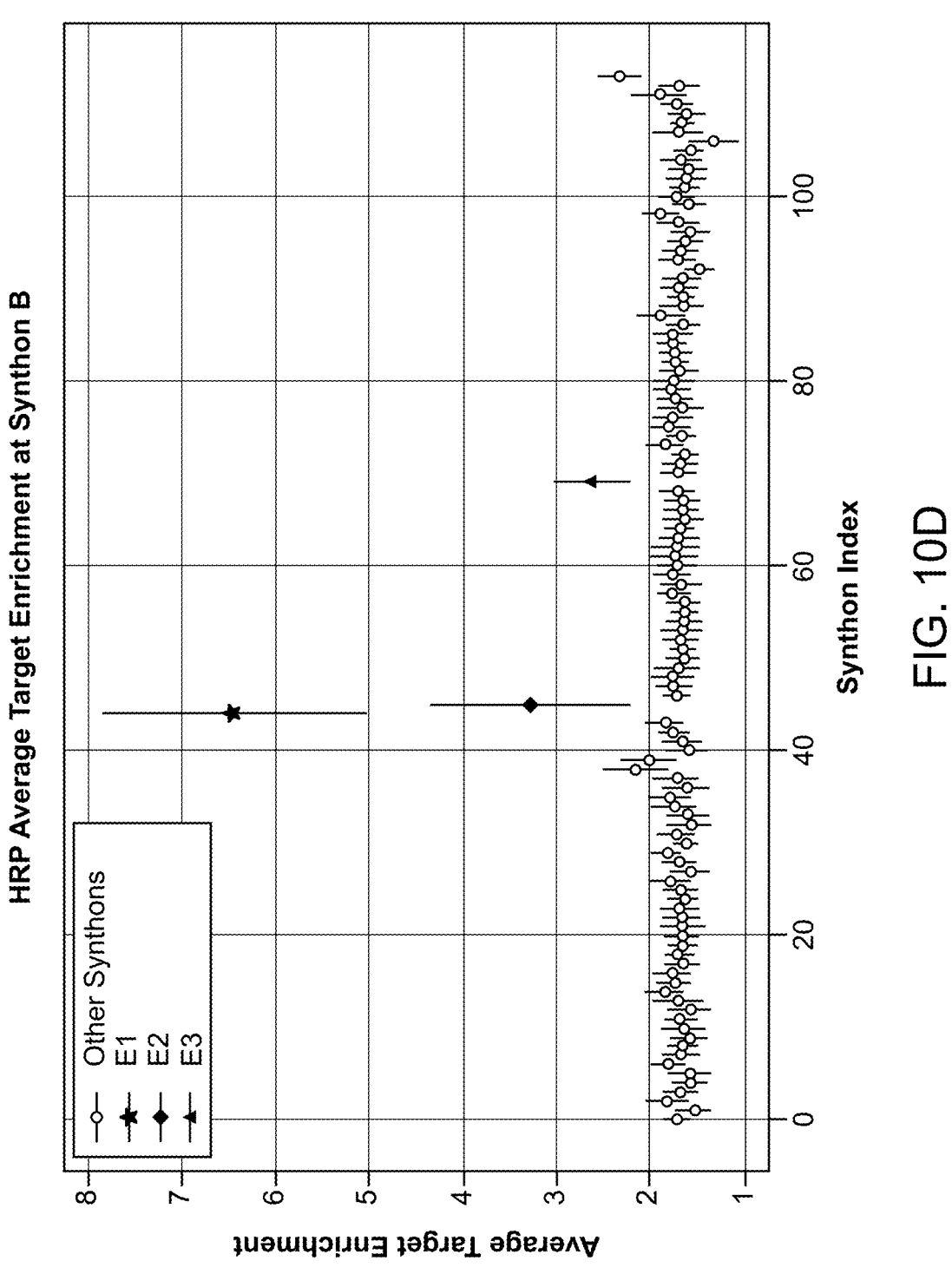
Figure 11A:
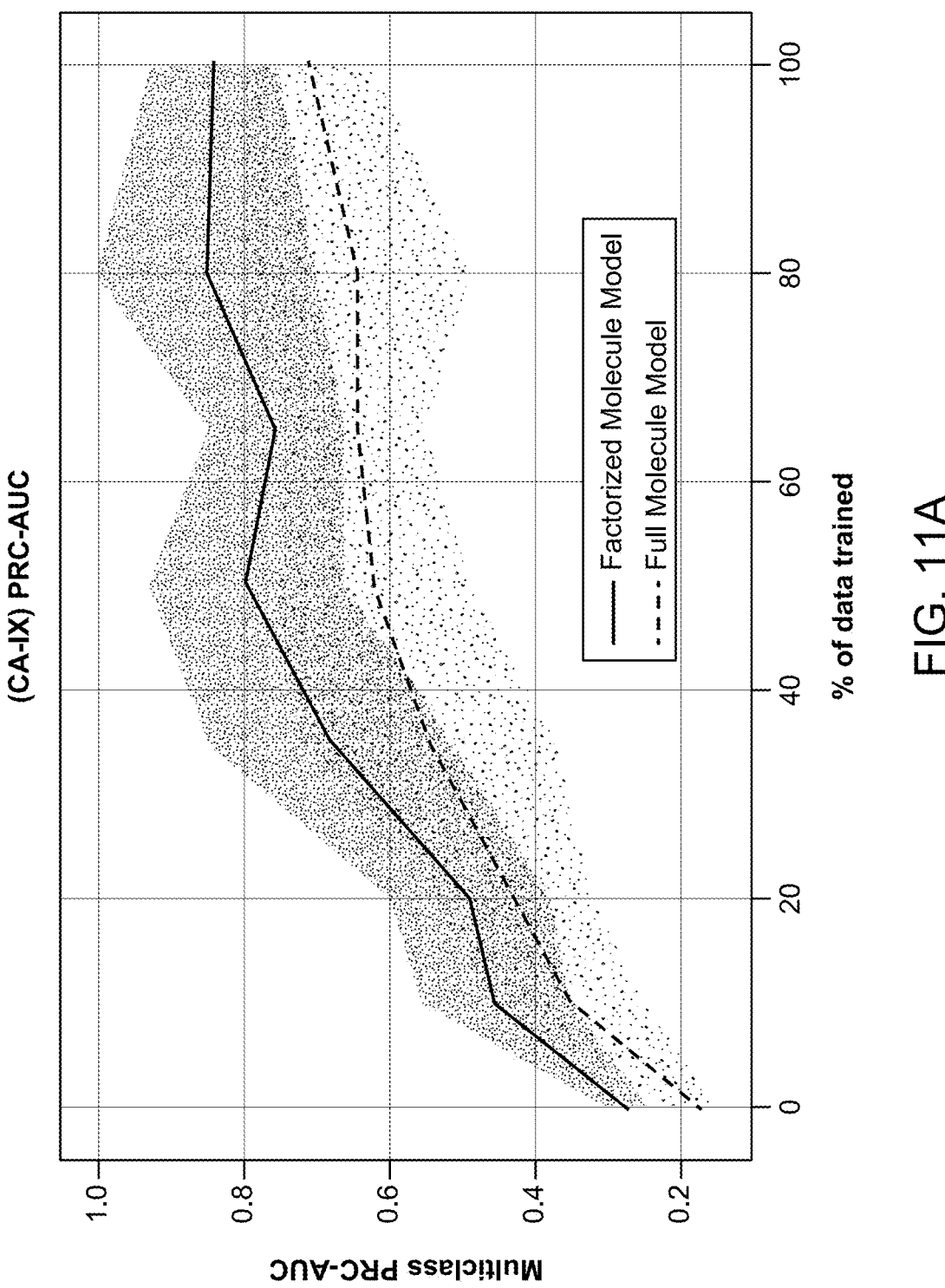
FIGS. 11A-11D show performance of models using factorized representations of molecules in comparison to using full molecule representations. Each model is trained with a different % of the data heldout.
Figure 11B:
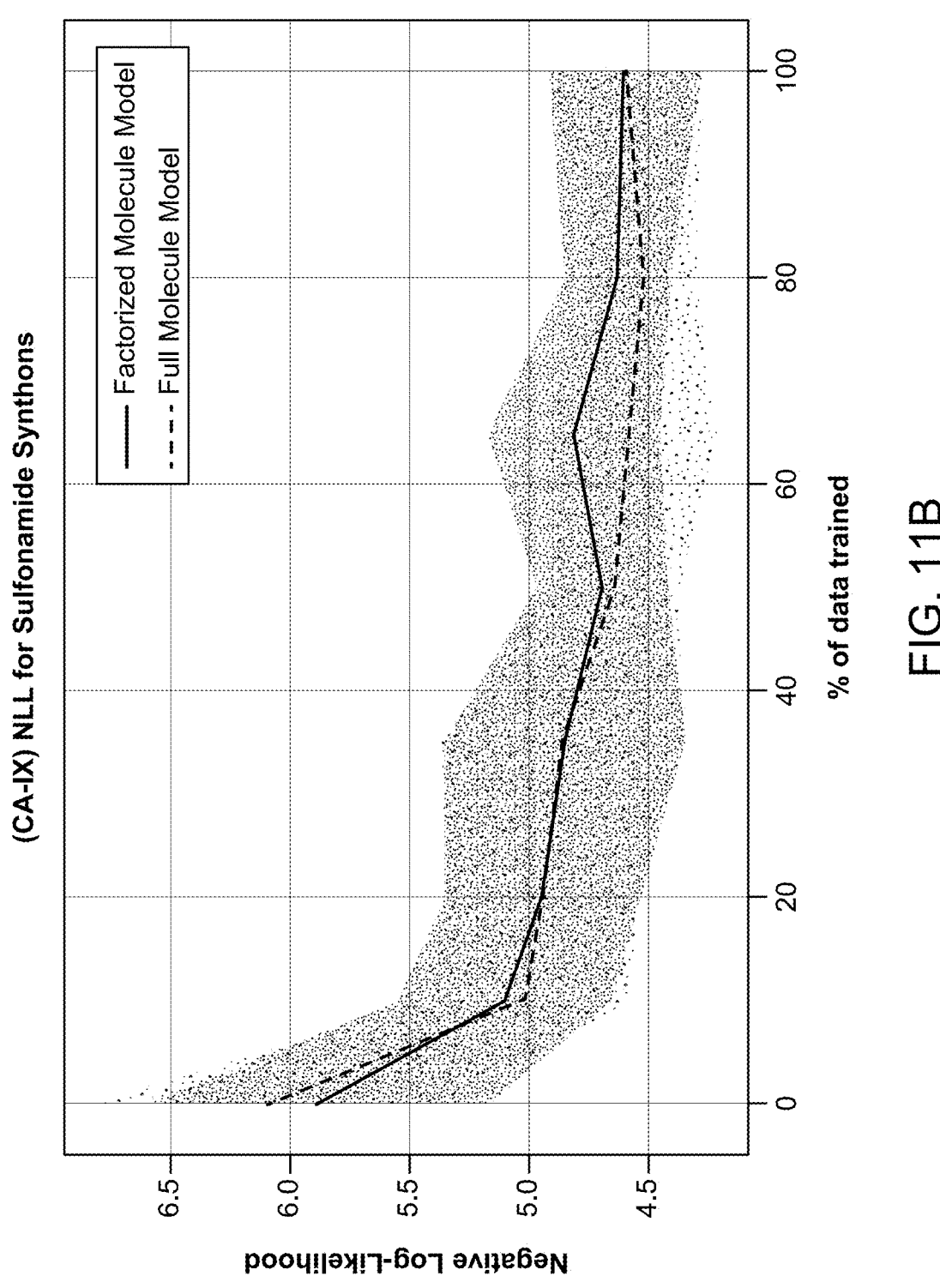
Figure 11C:
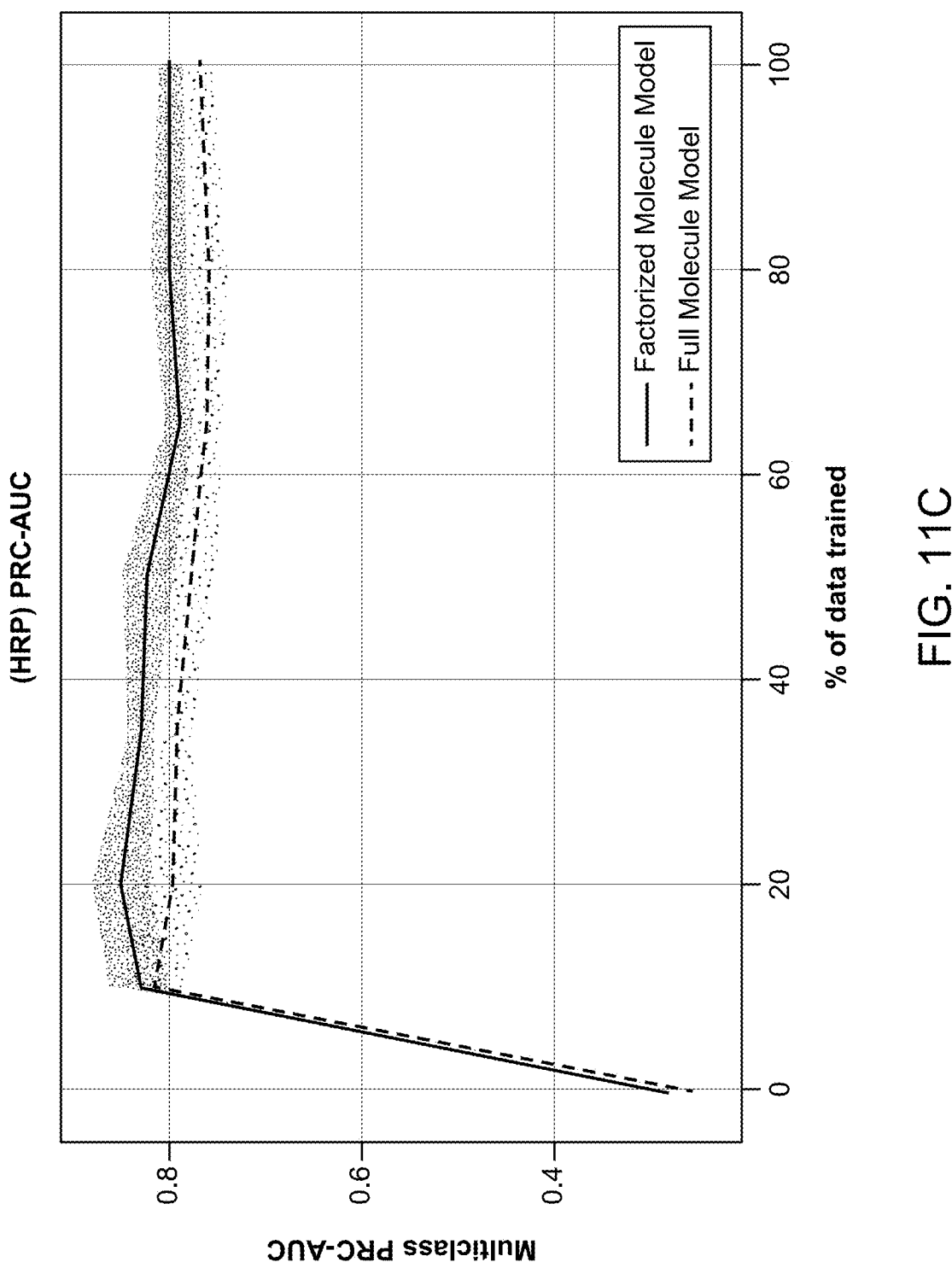
Figure 11D:
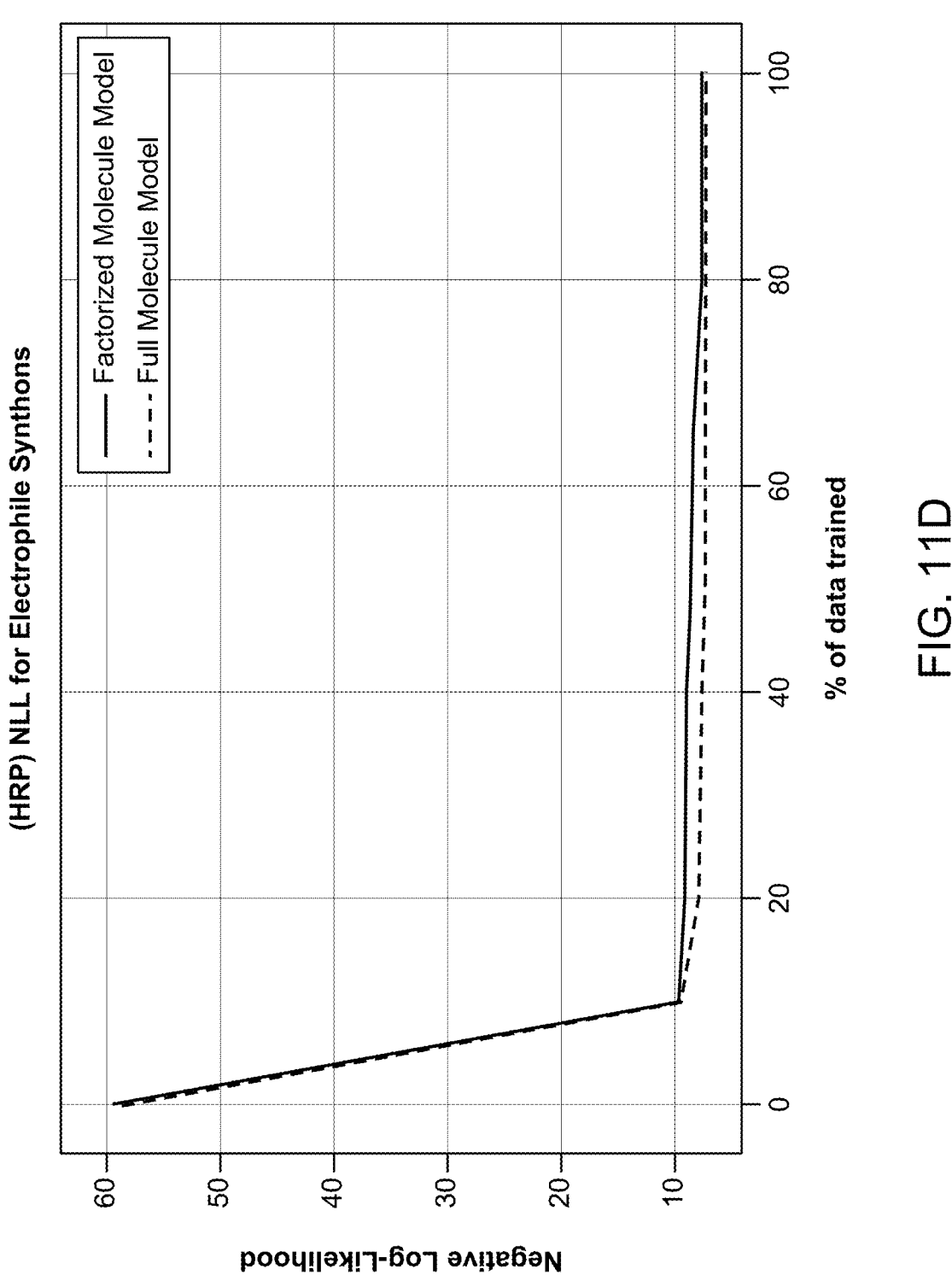

Both CA-IX and HRP have known pharmacophores. The benzene-sulfonamide motif is a known structure to promote binding to CA-IX. In this dataset, there are two synthons at the C position that includes benzene-sulfonamides, one that is meta-substituted with respect to the aryl group, and the other which is para-substituted. The benzene-sulfonamide substituted at the para position is much more highly active, in general, towards the CA-IX. Meanwhile, HRP has been a protein historically well-studied in DEL contexts that seem to have high affinity for compounds with sulfonyl chloride-derived Michael acceptors. In this dataset, there are three such synthons at the B position that shows high activity and are the three synthons we treat as "gold" labels for HRP. These structures are visualized in FIGS. 9A and 9B in descending order of binding affinity. Specifically, FIG. 9A shows known pharmacophores for carbonic anhydrase IX (CA-IX) pictured in order of binding affinity. FIG. 9B shows known pharmacophores of horseradish peroxidase (HRP) pictured in order of binding affinity. For CA-IX, benzene-sulfonamides are known structures to induce activity. The substitution of the sulfonamide affects the reactivity of the chemical specie, wherein the para-substituted constituent is found to be much more active. For HRP, electrophilic Michael acceptors are known pharmacophores. In this dataset, there are three Michael acceptors with activity.

Training Setup

A few training setups were included to validate the model's performance. At the most primitive level, the model's performance was evaluated on a held-out test set of the data. To that end, the data were randomly split into 5 different splits of 80%/10%/10% for train/validation/test sets respectively. Models were trained on the train set, selected based on the validation set and then finally tested on the held-out test set. Where applicable, the results were averaged across the 5 different splits.

Random splits are not always ideal for testing molecule datasets. In order to test the generalizability of molecule representations, many approaches attempt to split molecule by molecular scaffolds for DELs, rather than using generic molecule scaffolding strategies, synthons provide a natural grouping and separation of the chemical space. By using synthons to split the data, the generalizability of the model can be tested on unseen chemical structures.

In this dataset, the known pharmacophores are conveniently localized to specific synthons, so intuitive splitting strategies can be developed. Most of the signal is captured by these pharmacophores, so not all of these molecules were withheld from training. Instead, splits were performed on the synthon position that did not include these individual pharmacophores. Specifically, for CA-IX, the benzene-sulfonamides are at the C position, so synthon splits were created by splitting on the B position. For HRP, the electrophilic Michael Acceptors are at the B position, so the data were split at the C position. To understand more about the models, a third setup was introduced that tests the ability of the model to adapt under low-resource regimes. Since most of the signal reside in the molecules with known pharmacophores for their respective targets, the performance of the model was investigated when the amount of data provided to the model was changed. These experiments provide a good way to compare different representational modalities, as the factorized approach is expected to learn faster under resource-limited regimes.

Metrics

Several well-motivated metrics were utilized to evaluate the performance of the model without additional data (i.e., on-DNA $k_d$ data for DEL molecules). The observed data was observed through predicting the most likely count distribution, and the performance was measured through model loss, which is the negative log likelihood for a held-out test set. This is a typical metric to gauge the overall fitness of a probabilistic model. However, there are potential pitfalls in utilizing likelihood metrics, as the likelihood does not give indications of the usefulness of the learned representations. As the quality of the learned latent variables is of interest, metrics were developed to capture their ability to learn useful signals in the data. The latent variables in the model are used as the means of the zero-inflated Poisson distributions. The expected mean of the predicted distribution was used as the computed enrichment of the model, which is $\varepsilon = p*\lambda$, where p is the predicted zero-probability and A is the predicted latent score for a molecule. The model predicts both a distribution of counts for the control and target experiments, however, the former is mainly used to calibrate a molecule's affinity for the protein target.

The performance of the factorized model was evaluated at a synthon-aggregate level, as known pharmacophores are present for each of our two datasets CA-IX and HRP. A new metric was further developed to evaluate the quality of the factorized model's predictions by the ability of the model to separate out different classes of molecules. CA-IX has three distinct groups, $\{g_{para}, g_{meta}, g_{other}\}$, in order of protein activity for the para-substituted sulfonamides, meta-substituted sulfonamides, and other molecules respectively. HRP has four distinct groups, $\{g_{e1}, g_{e2}, g_{e3}, g_{other}\}$, in order of protein activity for the three different Michael Acceptor electrophiles and other molecules respectively.

To evaluate the model, a multi-class one-vs-one area under the curve (OvO AUC) for precision recall (PR) curves was constructed to evaluate the ability of the model to differentiate different molecule classes. Let $s(g_a|g_b)$ be the computed PR-AUC using $g_a$ as the positive class and $G_b$ as the negative class. Since the expected rankings of these molecule classes are known (i.e., $g_{para} > g_{meta} > g_{other}$), the AUC for each pair was computed and then the unweighted average was calculated over all such pairs. Since the data are heavily skewed towards representation of molecules without appreciable activity towards the protein target, each molecule class was equally weighted.

These AUC computations are noted Equation (4) and Equation (5):

$$PR\text{-}AUC^{CA\text{-}IX} = \frac{1}{3}[s(g_{para} \mid g_{meta}) + s(g_{para} \mid g_{other}) + s(g_{meta} \mid g_{other})] \quad (4)$$

-continued $$PR\text{-}AUC^{HRP} = \frac{1}{6}[s(g_{e1} \mid g_{e2}) + s(g_{e1} \mid g_{e3}) + \tag{5}$$

$$s(g_{e2} \mid g_{e3}) + s(g_{e1} \mid g_{other}) + s(g_{e2} \mid g_{other}) + s(g_{e3} \mid g_{other})]$$

Example 3: Disclosed Models Achieve Improved Performance Over Baseline and Enriches Important Pharmacophores FIGS. 10A-10D show predicted average marginal enrichment of both control and target counts for CA-IX and HRP. Here, the plots show the average marginal enrichment of a synthon as predicted the model on the test set. For both protein targets, the model correctly enriches the important synthons, which are the benzene-sulfonamides for CA and the Michael-Acceptor electrophiles for HRP. Moreover, the model predicts the correct ranking of these different groups. Of particular interest is that the model enriches synthon #39 (and to a lesser extent synthon #97) in the control experiments of CA, but this synthon is not significantly enriched in the target, which is the expected outcome. This signifies that the model correctly distinguishes the synthons which might have high noise (i.e., off-target binding).

The deep-probabilistic approach was compared to several baselines that computes enrichments based on counts alone. Poisson enrichment computes a maximum likelihood Poisson distribution for the target and control counts and then computes a ratio of the target at the lower 95% confidence interval (CI) and the control at the upper 95% CI.

Diff enrichment:

$$score = \frac{1}{n_c}\sum_i c_t^i - \frac{1}{n_t}\sum_j c_c^j$$

Ratio enrichment:

$$score = \left[\left(\frac{1}{n_c}\sum_i c_t^i\right) + 1\right]\bigg/\left[\left(\frac{1}{n_t}\sum_j c_c^j\right) + 1\right]$$

Poisson Enrichment: score=CI$_{lower,95}$[Poisson(Target)]/ CI$_{upper,95}$[Poisson(Control)]

Since these baselines are not trained models, but rather explicit functions of the count data, these metrics cannot be compared against the factorized model in terms of predicted likelihood. However, all methods provide a ranking of the test molecules, from which the aforementioned multi-class PR-AUC can be computed. Therefore, the performance of the model and baselines were compared on both random and synthon splits for both targets, as shown in Table 1. In terms of likelihood, the disclosed Factorized model that incorporates both load and replicate factors outperforms all ablations. Furthermore, the negative log likelihood (NLL) scores are generally higher for the synthon splits, which is evidence that they are more challenging to model. Interestingly, the load factor is more useful for the target data for CA-IX, while the replicate factor is more useful for HRP. This perhaps highlights the variance in the data even within experiments done in the same conditions.

Comparing the enrichment baselines to the results of the Factorized model, variants of the Factorized model outperform the baselines in terms of multi-class PRC-AUC. Baseline metrics do not incorporate the load data, but even the base factorized models outperform these baselines in most cases. Since the baseline models have oracle access to the actual data, this suggests that the Factorized models are capturing important aspects of the chemical data. It is further interesting to note that the multi-class PRC-AUC is best for the model in the synthon-split case, the more challenging learning scenario. This suggests that incorporating the correct factors of variation is important to generalize in challenging settings.

TABLE 1

Metrics for different ablations of the Factorized model compared to baseline enrichment metrics. Metrics were averaged across the test set over 5 different splits, either split randomly or based on synthons. Sum, ratio and Poisson enrichment uses the actual counts, whereas the model makes predictions on the test set.

| | Model | Control NLL | Target NLL | Sum NLL | PRC-AUC |
|---|---|---|---|---|---|
| CA-IX | Diff Enrichment | — | — | — | 0.23 ± 0.01 |
| | Ratio Enrichment | — | — | — | 0.26 ± 0.02 |
| | Poisson Enrichment | — | — | — | 0.25 ± 0.01 |
| | Factorized | 3.17 ± 0.03 | 2.82 ± 0.04 | 5.99 ± 0.06 | 0.28 ± 0.33 |
| | Factorized + Load | 2.97 ± 0.01 | 2.80 ± 0.02 | 5.77 ± 0.02 | 0.90 ± 0.03 |
| | Factorized + Rep | 3.13 ± 0.03 | 2.65 ± 0.03 | 5.78 ± 0.06 | 0.73 ± 0.34 |
| | Factorized + Load + Rep | 2.96 ± 0.02 | 2.65 ± 0.01 | 5.61 ± 0.01 | 0.84 ± 0.07 |
| HRP | Diff Enrichment | | | | 0.59 ± 0.01 |
| | Ratio Enrichment | | | | 0.48 ± 0.01 |
| | Poisson Enrichment | | | | 0.57 ± 0.01 |
| | Factorized | 6.51 ± 0.11 | 5.61 ± 0.09 | 12.12 ± 0.19 | 0.80 ± 0.12 |
| | Factorized + Load | 6.30 ± 0.03 | 5.35 ± 0.02 | 11.64 ± 0.04 | 0.78 ± 0.03 |
| | Factorized + Rep | 6.39 ± 0.04 | 5.53 ± 0.04 | 11.92 ± 0.08 | 0.81 ± 0.04 |
| | Factorized + Load + Rep | 6.23 ± 0.02 | 5.30 ± 0.02 | 11.54 ± 0.03 | 0.80 ± 0.04 |
| CA-IX | Diff Enrichment | | | | 0.22 ± 0.02 |
| | Ratio Enrichment | | | | 0.25 ± 0.02 |
| | Poisson Enrichment | | | | 0.24 ± 0.02 |
| | Factorized | 3.58 ± 0.34 | 2.83 ± 0.17 | 6.41 ± 0.46 | 0.13 ± 0.01 |
| | Factorized + Load | 3.13 ± 0.13 | 2.81 ± 0.18 | 5.94 ± 0.31 | 0.63 ± 0.42 |
| | Factorized + Rep | 3.54 ± 0.29 | 2.64 ± 0.14 | 6.19 ± 0.39 | 0.73 ± 0.33 |
| | Factorized + Load + Rep | 3.11 ± 0.11 | 2.61 ± 0.14 | 5.72 ± 0.25 | 0.75 ± 0.33 |

TABLE 1-continued

Metrics for different ablations of the Factorized model compared to baseline enrichment metrics. Metrics were averaged across the test set over 5 different splits, either split randomly or based on synthons. Sum, ratio and Poisson enrichment uses the actual counts, whereas the model makes predictions on the test set.

| | Model | Control NLL | Target NLL | Sum NLL | PRC-AUC |
|---|---|---|---|---|---|
| HRP | Diff Enrichment | | | | 0.59 ± 0.01 |
| | Ratio Enrichment | | | | 0.48 ± 0.01 |
| | Poisson Enrichment | | | | 0.56 ± 0.01 |
| | Factorized | 8.09 ± 2.04 | 7.36 ± 1.28 | 15.45 ± 3.32 | 0.85 ± 0.16 |
| | Factorized + Load | 7.44 ± 2.09 | 6.46 ± 1.35 | 13.90 ± 3.44 | 0.85 ± 0.13 |
| | Factorized + Rep | 8.75 ± 3.73 | 7.36 ± 1.69 | 16.11 ± 5.41 | 0.88 ± 0.05 |
| | Factorized + Load + Rep | 7.29 ± 2.11 | 6.26 ± 1.26 | 13.55 ± 3.36 | 0.90 ± 0.06 |

Example 4: Disclosed Models Exhibit Similar or Improved Performance in Comparison to Full-Molecule Models Even in Low-Resource Regimes One of the main benefits of utilizing a factorized model is it avoids building complex enumeration engines for DELs. However, while this is beneficial, the factorized models were evaluated to demonstrate that they perform competitively, or even better than, models that utilize full molecule representations. To do so, an in-depth investigation was conducted by training both versions of the model under different data-limiting regimes. Reference is now made to FIGS. 11A-11D which show performance of models using factorized representations of molecules in comparison to using full molecule representations. Each model was trained with a different % of the data heldout. Here, the performance of the models were compared a function of amount of data supplied during training. For both CA-IX and HRP, the multi-class PR-AUC is superior for the factorized model compared to the full model at each point. Meanwhile, the test likelihoods for the two models are very comparable as a function of the amount of data supplied. These results support the use of factorized representations as the methodology places the correct inductive biases into the model as a more efficient medium of learning.

Example 5: Disclosed Models Provide Insights into the Data

Figure 12A:
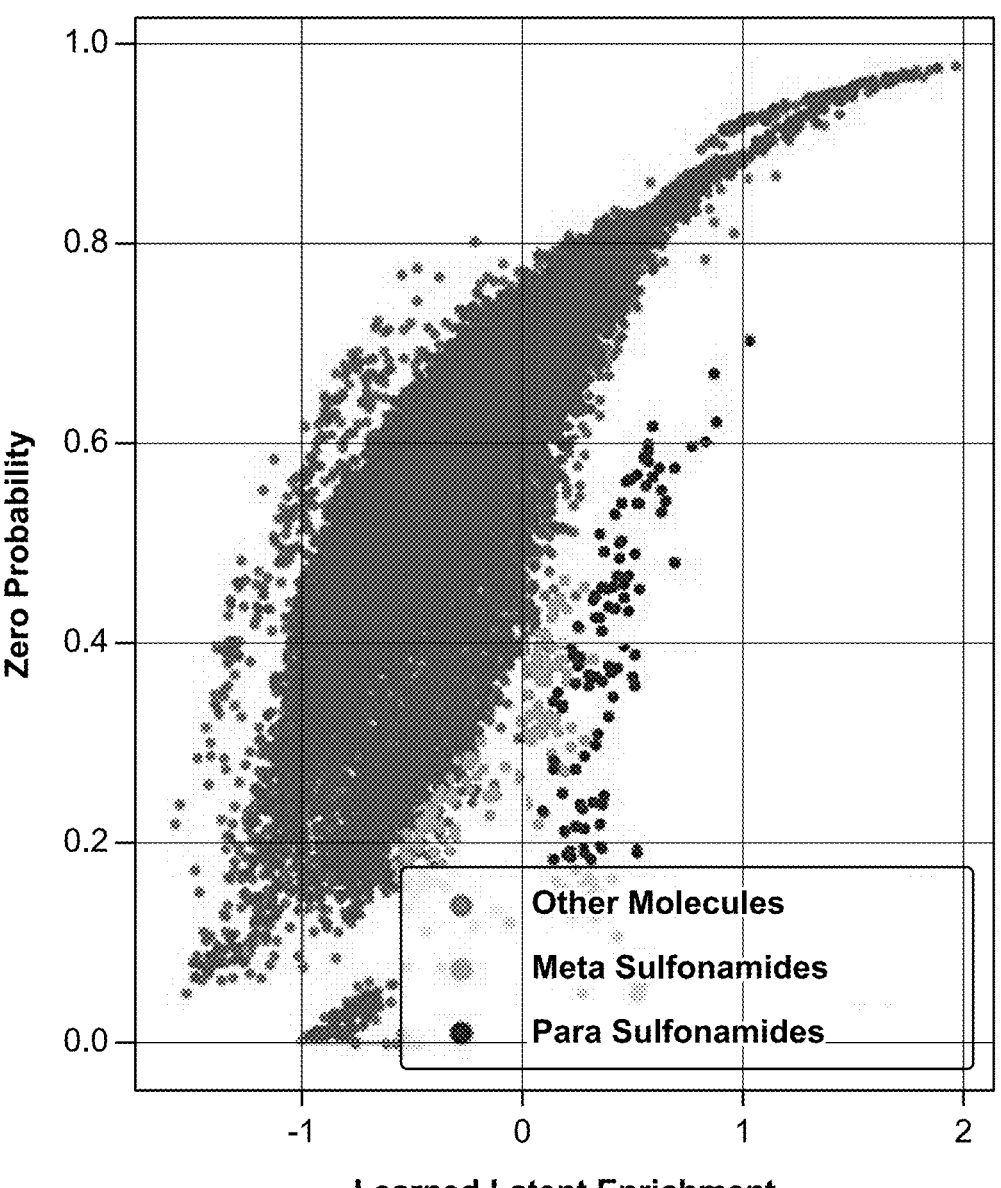
FIGS. 12A and 12B demonstrate that predicted zero-probability is a good measure of predicted noise for CA-IX and HRP.
Figure 12B:
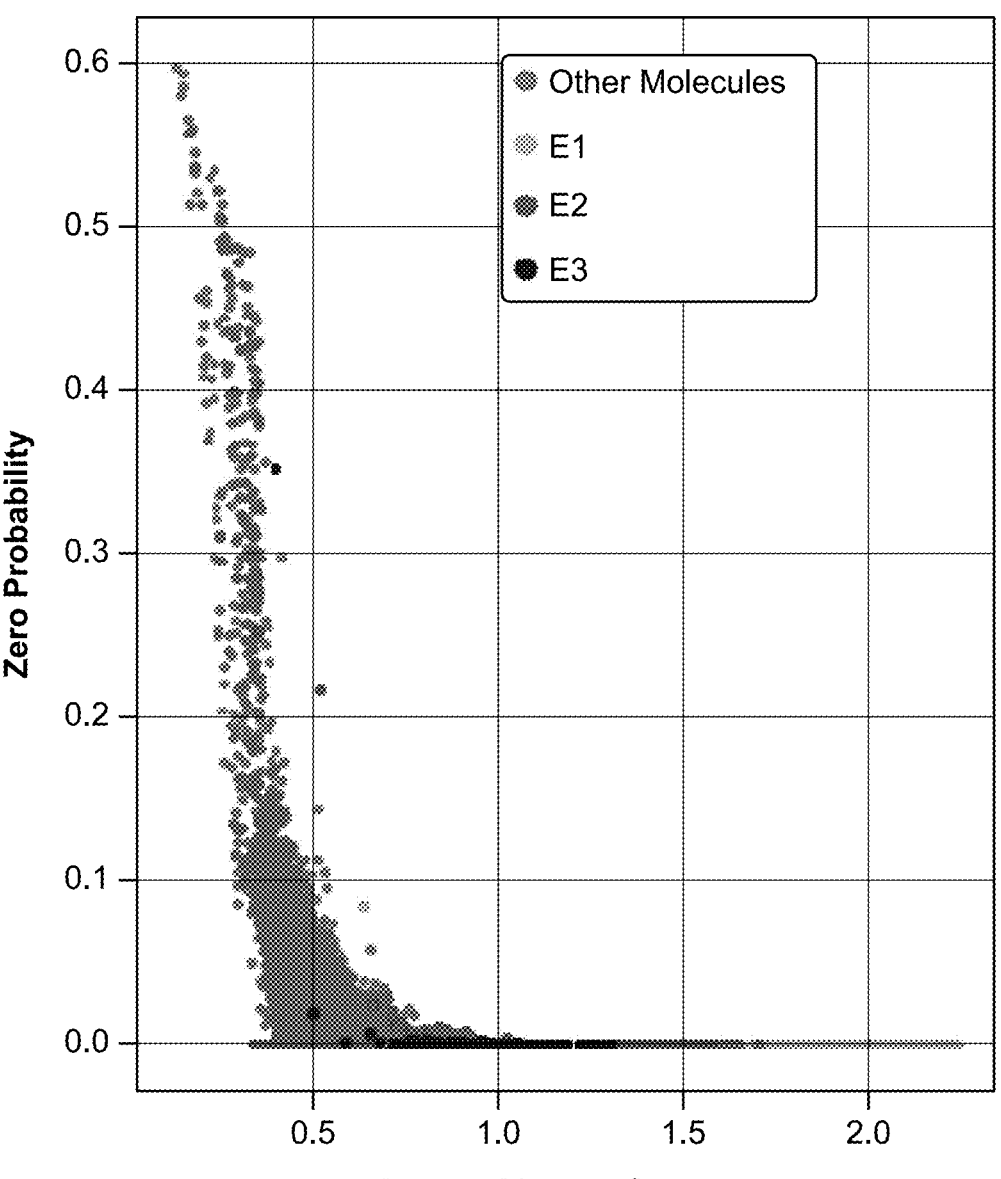

The factorized model further provides interpretable insights into the data. Since the zero-inflated distributions were used as the output distributions, this zero-probability can be intuitively used as a measure of noisiness of the data. FIGS. 12A and 12B demonstrate that predicted zero-probability is a good measure of predicted noise for CA-IX and HRP.

In FIGS. 12A and 12B, the learned latent scores $\lambda$ were plotted as a function of the predicted zero probability. For HRP, all the molecules having the substructures with known activity have high predicted scores and low zero-probability—the signal is strong and the noise is low. This is also seen in FIGS. 11A-11D, as the models trained on a small fraction of the HRP data quickly achieves optimal performance. However, the plot for CA-IX shows a number of molecules with high learned scores, but also high zero-probability—this region of the distribution likely contains more noise. Compared to the HRP data, the predicted scores for the benzene-sulfonamide containing molecules for CA-IX have some uncertainty associated, as implicated by their predicted zero-probabilities.

Figure 13A:
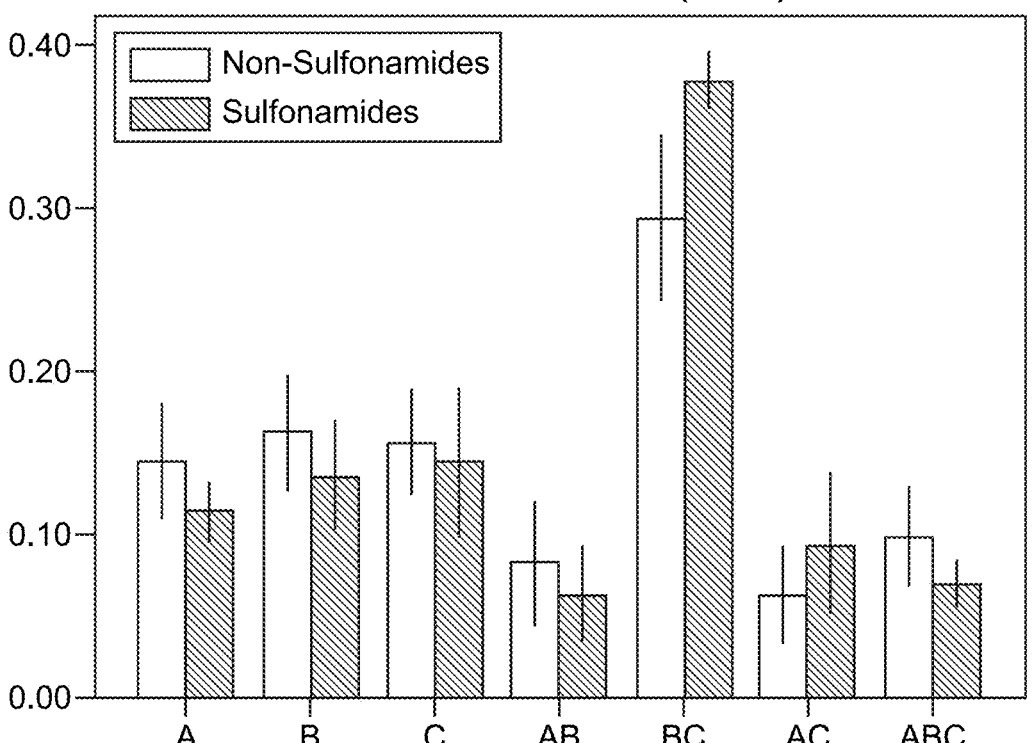
FIGS. 13A and 13B depict the attention distribution of the model for the CA-IX and HRP datasets, respectively.
Figure 13A:
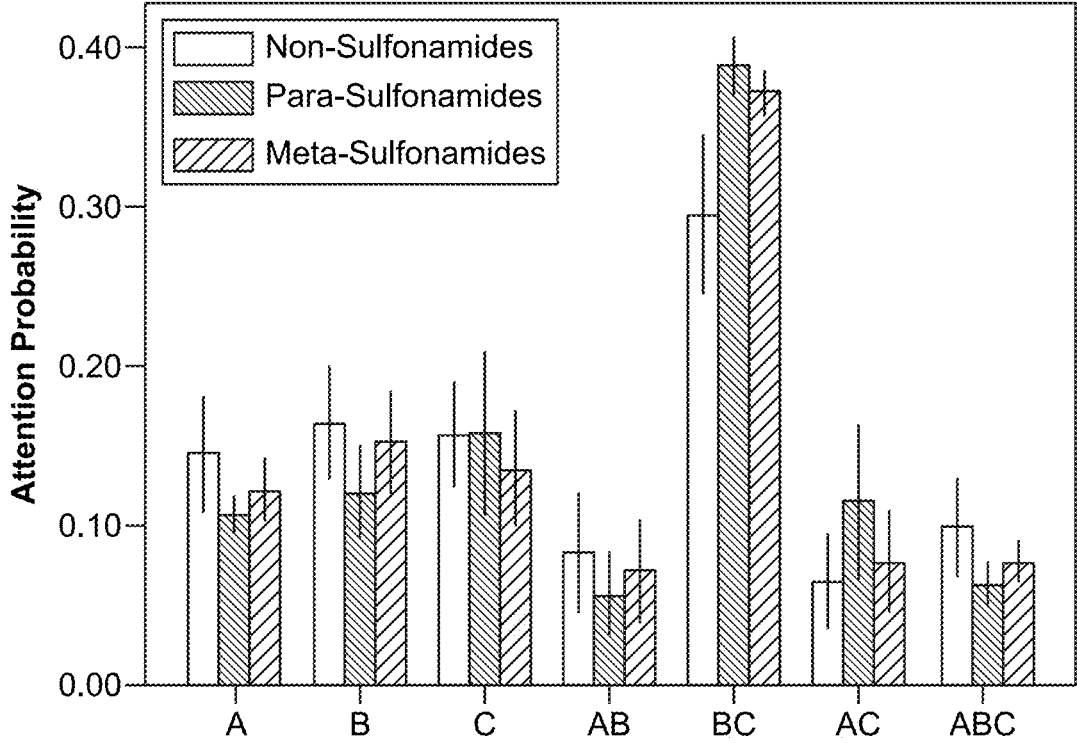
Figure 13B:
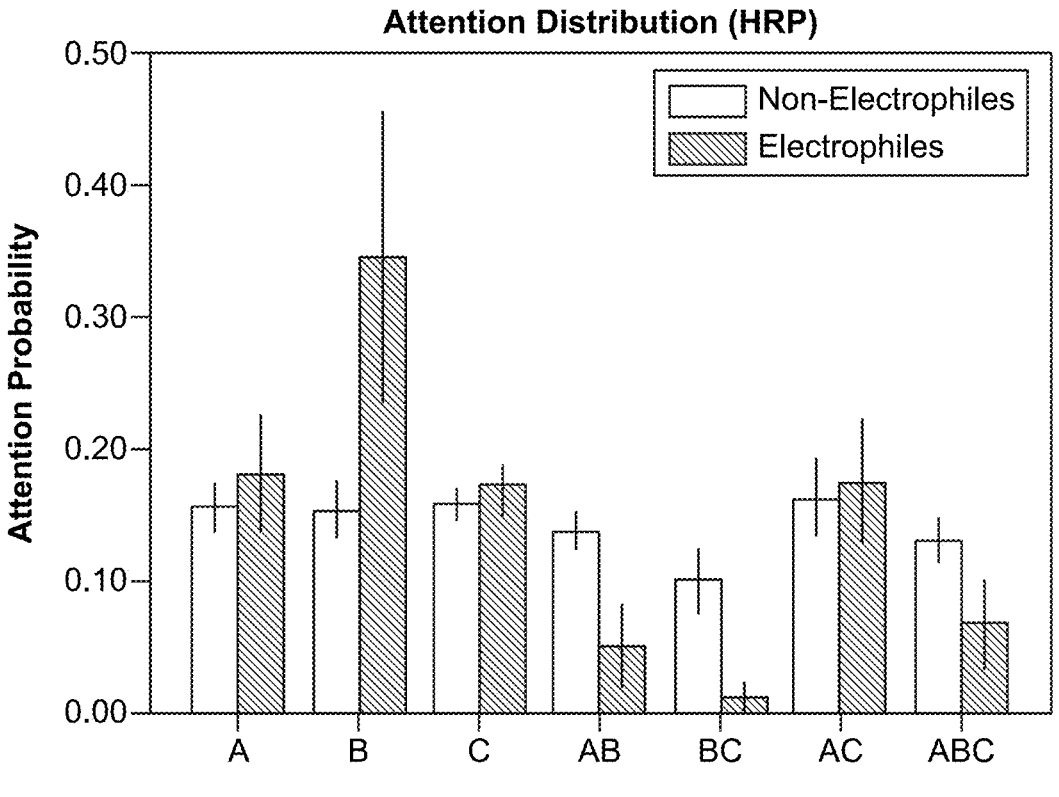
Figure 13B:
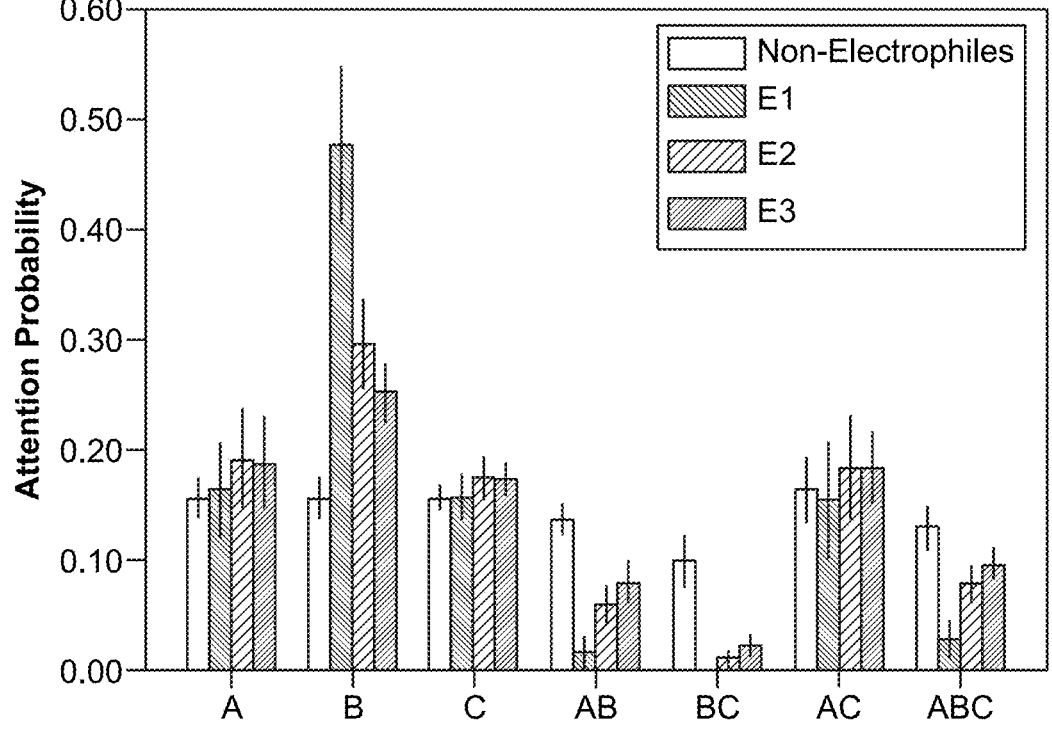

Additionally, using attention provides good interpretability and insights to the model. This may be valuable for purposes of synthesizing compounds e.g., to include or exclude certain synthons in synthesis campaigns. FIGS. 13A and 13B depict the attention distribution of the model for the CA-IX and HRP datasets, respectively. For CA-IX, the attention probabilities were primarily focused on the $x_{bc}$ di-synthon, while for HRP, the attention probabilities were primarily distributed on the $x_b$ mono-synthon. As the sulfonamides are on the C position for CA-IX, while the electrophiles are on the B position for HRP, these results indicate that both models chose the highest weight to be placed on synthon embeddings incorporating the correct synthon position. Interestingly, the model for CA-IX chose the di-synthon $x_{bc}$, instead of just the mono-synthon at the C position, which indicates enrichment of certain di-synthons. This establishes the value of the disclosed models which considers higher order synthon representations beyond solely mono-synthons.

Example 6: Disclosed Models Generalize to DNA-Encoded Library Dataset for Kinase Inhibitors (KinDEL)

In a separate set of experiments, the disclosed methods were applied to two protein kinase targets (discoidin domain receptor tyrosine kinase 1 (DDR1) and mitogen-activated protein kinase 14 (MAPK14)).

Training Setup

In this example, Kinase Inhibitor DNA-Encoded Library (KinDEL), a 100 million small molecule library, was tested against two kinase targets, MAPK14 and DDR1. Various benchmark tasks were developed and implemented to demonstrate the efficacy of using DEL data in deriving therapeutic insights. Additionally, validation of these computational approaches was determined by biophysical assay data.

The dataset utilized in this example included roughly three main parts:

1. synthesis of the DEL,
2. selection experiments, and
3. biophysical validation data.

Typically, selection experiments with DELs are run with at least a blank for control, which was also run in this example.

For step 1 (DEL synthesis), the DEL was designed as a tri-synthon library, comprising 382 synthons in the first step, 192 synthons in the second step and 1152 synthons in the terminal or capping step (~85M molecules in total). The first two steps were done either by acylation with N-protected amino acid, followed by deprotection, or by immobilization of the DNA to a solid support followed by a series of chemical transformations for acylation. In the final step, the downstream amino groups were reacted with monofunctional acids or aldehydes.

For step 2 (DEL Selection), selection experiments were then carried out using the synthesized library. Biotinylated Proteins DDR1 and MAPK1 were immobilized on a Phynexus tip. The library was combined with immobilized protein, and the mixture goes through multiple rounds of washing to successively remove any weak binders. Afterwards, hot water was used to elute the binders, which were then amplified and sequenced using Novaseq S4 platform.

For step 3 (biophysical assay validation), to accompany DEL data, which can compromise quality with volume, biophysical data was also collected on a small number of molecules-both on- and off-DNA. On-DNA, Fluorescence Polarization (FP) was utilized, which measures binding events in solution through polarized light. Off-DNA, Surface Plasmon Resonance (SPR) was used, which also uses light to measure molecular interactions.

Figure 14:
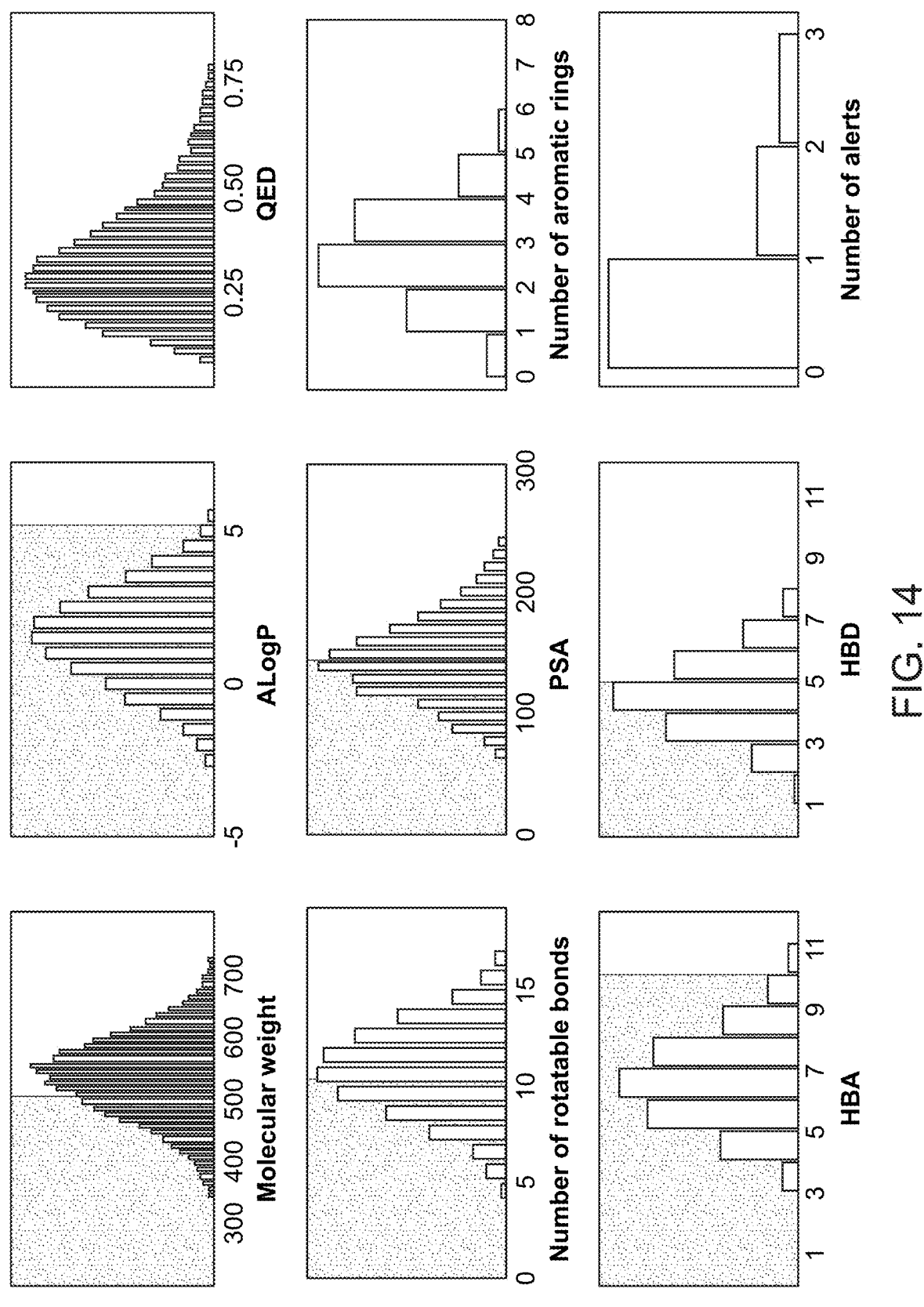
FIG. 14 depicts the distributions of chemical properties in the Kinase Inhibitor DNA-Encoded Library (KinDEL) dataset. These selected properties are often used to assess the druglikeness of molecules. The light blue areas are compliant with the Lipinski and Veber rules of druglikeness. QED: quantitative estimate of druglikeness; PSA: polar surface area; HBA: hydrogen bond acceptors; HBD: hydrogen bond donors.
Figure 15:
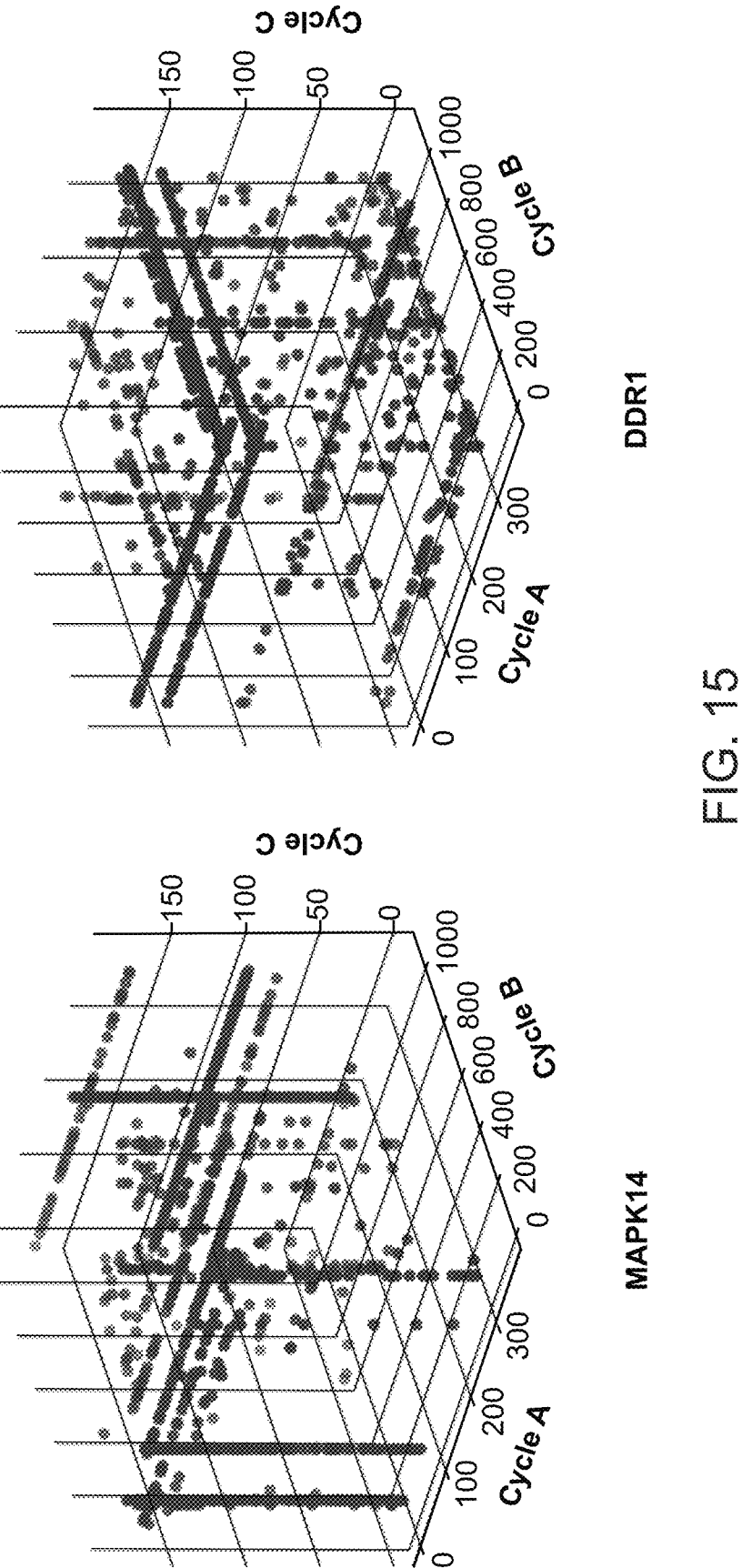
FIG. 15 depicts the 3D cube visualization of the KinDEL dataset, where each axis corresponds to a different cycle in the DEL. Points in the plot are the most enriched compounds (measured using Poisson enrichment). The linear patterns can be interpreted as enriched disynthons, i.e. combinations of two synthons that often bind to the protein target.

The KinDEL dataset contained ~85M molecules with their unique sequence counts over 3 different replicates of each experimental condition. FIG. 14 displays the distribution of chemical properties in the KinDEL dataset. These selected properties are often used to assess the druglikeness of molecules. Additionally, FIG. 15 is a 3D cube visualization of the dataset, where each axis corresponds to a different cycle in the DEL. Utilizing a Poisson enrichment, points on the plot represent the most enriched molecules. Further, linear patterns in FIG. 15 can represent enriched disynthons (e.g. combinations of two synthons that bind to the protein target (e.g. MAPK14 and DDR1)).

The KinDEL dataset was used to build predictive models of binding affinity. To that end, various benchmark models were investigated and their performance was compared on their ability to model binding affinity.

Benchmarking and Model Performance Evaluation

The benchmark featured two biological targets: MAPK14 and DDR1. For each target a held-out test set of compounds was selected from the DEL, and these candidates were resynthesized on- and off-DNA to create an in-library held-out test set. Additional compounds were added from outside the library to create an extended held-out test set. The binding affinity (Kd or $K_D$) of all molecules in the held-out sets was measured in biophysical assays. The model (DEL-Compose) performance reported in the benchmark of the held-out sets is the Spearman correlation coefficient between model predictions and experimental $K_D$. Additionally, model performance on the internal testing set was reported as the value of the loss function, which is MSE for all the models except for DEL-Compose, for which negative log-likelihood is reported.

The KinDEL datasets were split using two strategies, ensuring that all held-out compounds were placed in the testing set and not used for training. The first type of the data split was the random split, where 10% randomly selected compounds were placed in the validation set, and another 10% compounds were placed in the testing set. The second data split was the disynthon split, where pairs of blocks B and C were randomly sampled, and all compounds containing this combination were put in the same subset using the same 80-10-10 ratio between the training, validation, and testing sets, respectively. Each dataset was split five times for each splitting strategy, and the reported performance of the models was aggregated over five training runs.

To benchmark the models, commonly used models were compared to model DEL data. Two non-machine learning (ML) baselines were computed to gauge the alignment between DEL screening results and experimental $K_D$ data. The first baseline was the Spearman correlation between sum of the sequence counts of the molecules that bound to the target in three repeated experiments. The second baseline was the Poisson enrichment (Gerry et al., 2019) of the molecules that also took into account counts of the molecules that bound to the matrix instead of the target.

In this example, six machine learning (ML) models were compared. Random forest (RF), XGBoost, k-nearest neighbors (kNN), and deep neural network (DNN) use Morgan fingerprints (radius=2, length=2048) as input features and were trained to predict Poisson enrichment. Graph isomorphism network (GIN) was a graph neural network using molecular graphs as an input and predicting Poisson enrichment. DELCompose refers to the probabilistic model disclosed herein that used Morgan fingerprints as an input and predicts the parameters of the zero-inflated Poisson distribution that fit the sequence count data. DEL-Compose was further differentiated by a model that was ran with the fully enumerate molecule structure (DEL-compose$^{(M)}$), and another model which was ran using the synthon structures (DEL-compose$^{(S)}$).

The architectures of the neural network models followed the implementation in the original publications. The DNN architecture contained multiple linear layers with ReLU activation, batch normalization, and dropouts after each layer except for the last one. All neural networks were trained using the Adam optimizer until convergence with early stopping when the validation loss did not improve for more than 5 epochs.

Results

Tables 2 and 3 demonstrate the performance of the aforementioned models on MAPK14 and DDR1, respectively. The Poisson enrichment baseline served as an estimate of the alignment between DEL screening results and experimental $K_D$ computed directly from the sequence count data. Interestingly, in the case of the compounds selected for the off-DNA synthesis for MAPK14, the enrichment baseline was lower than predictions of the ML models trained using enrichment as targets. This showed that ML models have denoising capabilities, which makes them suitable for compound selections in DEL screening experiments. The results show that DEL-Compose, which views the data from a probabilistic perspective, performed favorably compared to other baseline models that output point estimates of the data. Since DEL data is noisy, capturing the uncertainty in the data, for instance with the zero-inflated Poisson distributions used to parametrize DEL-Compose, was valuable. The disynthon split was a more challenging task, since structures were entirely removed from the training data, and the models had to infer based on chemical structures. The data showed that the models generally perform worse for disynthon splits for MAPK14, and perform comparably for DDR1 in this new data split. Overall, the results indicate DEL-Compose's superior performance in predicting binding affinity relative to the benchmark algorithms for both MAPK14 and DDR1 across multiple benchmark metrics.

For MAPK14, random and disynthon splits both featured higher Spearman correlation coefficients between the DEL-compose model predictions and experimental Kd relative to the other 5 machine learning models for the extended on-DNA dataset (extended held-out test set). This dataset featured additional compounds, not featured in the training of the models, which may represent a more challenging and/or diverse testing dataset. Despite this, the generalizability of DEL-compose is highlighted by a higher Spearman correlation coefficient. Additionally, the DEL-compose showed superior denoising capabilities relative to the other 5 models, as shown by a higher Spearman correlation coefficient value in the "In Library off-DNA" conditions across random and synthon splits.

For DDR1, random and disynthon splits both featured higher Spearman correlation coefficients between the DEL-compose model predictions and experimental $K_D$ relative to the other 5 machine learning models for the In-Library on-DNA and off-DNA datasets, with the exception of kNN which performed similarly to DEL-compose model predictions in the random split.

Together, the examples provided herein represent an exemplary use case, among many, of the present disclosure in providing technical advantages and technological improvements in predicting binding affinity of DEL to a diverse array of biological targets (e.g. MAPK14, DDR1, CA-IX, and HRP).

TABLE 2

Model performance evaluation for MAPK14. The test loss column ("Test MSE") contains values of the loss function computed on the internal testing set. The performance for the on- and off-DNA compounds is the Spearman correlation between model predictions and experimental $K_D$.

| Split | Model | Test MSE | In Library | | Extended- |
| | | | On-DNA | Off-DNA | DNA |
| --- | --- | --- | --- | --- | --- |
| | Counts | — | 0.717 | −0.001 | — |
| | Poisson | — | 0.737 | 0.166 | — |
| Random | RF | 0.064 ± 0.003 | 0.694 ± 0.030 | 0.370 ± 0.111 | 0.453 ± 0.028 |
| | XGBoost | 0.056 ± 0.002 | 0.477 ± 0.009 | 0.345 ± 0.036 | 0.196 ± 0.074 |
| | kNN | 0.072 ± 0.002 | 0.649 ± 0.041 | 0.466 ± 0.103 | 0.464 ± 0.040 |
| | DNN | 0.139 ± 0.001 | 0.582 ± 0.062 | 0.514 ± 0.071 | 0.351 ± 0.058 |
| | GIN | 0.062 ± 0.004 | 0.511 ± 0.038 | 0.492 ± 0.139 | 0.174 ± 0.067 |
| | DEL-compose(M) | — | 0.448 ± 0.054 | 0.756 ± 0.011 | 0.569 ± 0.048 |
| | DEL-compose(S) | — | 0.420 ± 0.050 | 0.760 ± 0.018 | — |
| Disython | RF | 0.154 ± 0.016 | 0.157 ± 0.138 | 0.505 ± 0.062 | 0.302 ± 0.096 |
| | XGBoost | 0.148 ± 0.015 | 0.377 ± 0.054 | 0.482 ± 0.045 | 0.212 ± 0.126 |
| | kNN | 0.165 ± 0.014 | 0.402 ± 0.074 | 0.266 ± 0.078 | 0.367 ± 0.043 |
| | DNN | 0.160 ± 0.017 | 0.275 ± 0.135 | 0.429 ± 0.118 | 0.184 ± 0.146 |
| | GIN | 0.153 ± 0.011 | 0.090 ± 0.084 | 0.483 ± 0.151 | −0.080 ± 0.071 |
| | DEL-compose(M) | — | 0.120 ± 0.070 | 0.716 ± 0.052 | 0.421 ± 0.054 |
| | DEL-compose(S) | — | 0.128 ± 0.049 | 0.748 ± 0.024 | — |

54

TABLE 3

Model performance evaluation for DDR1. The test loss column ("Test MSE") contains values of the loss function computed on the internal testing set. The performance for the on- and off-DNA compounds is the Spearman correlation between model predictions and experimental $K_D$.

| Split | Model | Test MSE | In Library | | Extended- |
| | | | On-DNA | Off-DNA | DNA |
| --- | --- | --- | --- | --- | --- |
| | Counts | — | 0.673 | 0.271 | — |
| | Poisson | — | 0.779 | 0.441 | — |
| Random | RF | 0.685 ± 0.011 | 0.578 ± 0.034 | 0.267 ± 0.022 | 0.608 ± 0.021 |
| | XGBoost | 0.519 ± 0.011 | 0.553 ± 0.032 | 0.252 ± 0.031 | 0.587 ± 0.025 |
| | kNN | 0.748 ± 0.010 | 0.599 ± 0.025 | 0.316 ± 0.026 | 0.508 ± 0.036 |
| | DNN | 1.261 ± 0.057 | 0.703 ± 0.025 | 0.335 ± 0.009 | 0.668 ± 0.033 |
| | GIN | 0.454 ± 0.012 | 0.572 ± 0.044 | 0.283 ± 0.028 | 0.579 ± 0.037 |
| | DEL-compose(M) | — | 0.731 ± 0.016 | 0.509 ± 0.024 | 0.646 ± 0.024 |
| | DEL-compose(S) | — | 0.689 ± 0.048 | 0.483 ± 0.044 | — |
| Disython | RF | 1.151 ± 0.151 | 0.481 ± 0.120 | 0.330 ± 0.081 | 0.557 ± 0.082 |
| | XGBoost | 0.989 ± 0.131 | 0.523 ± 0.071 | 0.241 ± 0.031 | 0.572 ± 0.046 |
| | kNN | 1.109 ± 0.088 | 0.663 ± 0.043 | 0.363 ± 0.038 | 0.523 ± 0.036 |
| | DNN | 0.977 ± 0.104 | 0.572 ± 0.063 | 0.265 ± 0.051 | 0.598 ± 0.055 |
| | GIN | 0.966 ± 0.090 | 0.410 ± 0.020 | 0.070 ± 0.031 | 0.546 ± 0.023 |
| | DEL-compose(M) | — | 0.663 ± 0.022 | 0.463 ± 0.023 | 0.492 ± 0.049 |
| | DEL-compose(S) | — | 0.563 ± 0.084 | 0.429 ± 0.069 | — |

What is claimed is:

1. A method for performing molecular screening of a compound from a virtual library of compounds for binding to a protein target, the method comprising:
obtaining a plurality of synthons forming the compound;
transforming the plurality of synthons into a plurality of synthon representations comprising one or more monosynthon representations, one or more disynthon representations, and one or more trisynthon representations, wherein the transforming comprises:
transforming the plurality of synthons to generate one or more monosynthon representations;
transforming the one or more monosynthon representations to generate one or more disynthon representations; and
transforming the one or more disynthon representations to generate one or more trisynthon representations;
combining the plurality of synthon representations into a molecular embedding by implementing a multi-head attention mechanism across the plurality of synthon representations, wherein the molecular embedding comprises learned attention weights for the plurality of synthon representations; and
using a multilayer perceptron (MLP) neural network, analyzing the molecular embedding to generate at least a target enrichment prediction representing a measure of binding between the compound and the target.

2. The method of claim 1, further comprising determining a binding affinity value between the compound and the target using the target enrichment prediction.

3. The method of claim 1, wherein implementing the multi-head attention mechanism comprises using one or more learned attention weights to rank the plurality of synthons for their ability to bind to the target.

4. The method of claim 1, further comprising performing probabilistic modeling using at least the target enrichment prediction by applying a probability density function that models experimental target counts.

5. The method of claim 4, wherein the probability density function is represented by any one of a Poisson distribution, Binomial distribution, Gamma distribution, Binomial-Poisson distribution, or negative binomial distribution.

6. A non-transitory computer readable medium for developing a machine learning model for use in ML enabled molecular screening of a compound from a virtual library of compounds for binding to a protein target, the non-transitory computer readable medium comprising instructions that, when executed by a processor, cause the processor to perform steps comprising:

obtain a plurality of synthons forming the compound;

transform the plurality of synthons into a plurality of synthon representations comprising one or more monosynthon representations, one or more disynthon representations, and one or more trisynthon representations, wherein the transform step comprises:

transforming the plurality of synthons to generate one or more monosynthon representations;

transforming the one or more monosynthon representations to generate one or more disynthon representations; and transforming the one or more disynthon representations to generate one or more trisynthon representations;

combine the plurality of synthon representations into a molecular embedding by implementing a multi-head attention mechanism across the plurality of synthon representations, wherein the molecular embedding comprises learned attention weights for the plurality of synthon representations; and use a multilayer perceptron (MLP) neural network, analyzing the molecular embedding to generate at least a target enrichment prediction representing a measure of binding between the compound and the target.

7. The non-transitory computer readable medium of claim 6, wherein instructions for training the MLP further comprises instructions that, when executed by the processor, cause the processor to perform steps comprising: perform probabilistic modeling using at least the target enrichment prediction by applying a probability density function that models experimental target counts.

8. The non-transitory computer readable medium of claim 6, further comprising instructions that, when executed by the processor, cause the processor to determine a binding affinity value between the compound and the target using the target enrichment prediction.

9. The non-transitory computer readable medium of claim 6, wherein the instructions that cause the processor to implement the multi-head attention mechanism further comprises instructions that, when executed by the processor, cause the processor to use one or more learned attention weights to rank the plurality of synthons for their ability to bind to the target.

10. The non-transitory computer readable medium of claim 6, further comprising instructions that, when executed by a processor, cause the processor to: perform probabilistic modeling using at least the target enrichment prediction by applying a probability density function that models experimental target counts.

11. The non-transitory computer readable medium of claim 10, wherein the probability density function is represented by any one of a Poisson distribution, Binomial distribution, Gamma distribution, Binomial-Poisson distribution, or negative binomial distribution.

12. A method for performing molecular screening of a compound from a virtual library of compounds for binding to a protein target, the method comprising:

obtaining a plurality of synthons forming the compound;

transforming the plurality of synthons into a plurality of synthon representations comprising one or more monosynthon representations, one or more disynthon representations, and one or more trisynthon representations, wherein the transforming comprises:

transforming the plurality of synthons using a first learned representation model to generate one or more monosynthon representations;

transforming the one or more monosynthon representations using a second learned representation model to generate one or more disynthon representations; and transforming the one or more disynthon representations using a third learned representation model to generate one or more trisynthon representations;

combining the plurality of synthon representations into a molecular embedding; and using a multilayer perceptron (MLP) neural network, analyzing the molecular embedding to generate at least a target enrichment prediction representing a measure of binding between the compound and the target.

13. The method of claim 12, further comprising determining a binding affinity value between the compound and the target using the target enrichment prediction.

14. The method of claim 12, further comprising performing probabilistic modeling using at least the target enrichment prediction by applying a probability density function that models experimental target counts.

15. The method of claim 14, wherein the probability density function that models the experimental control counts is represented by any one of a Poisson distribution, Binomial distribution, Gamma distribution, Binomial-Poisson distribution, or negative binomial distribution.

* * * * *